(12) United States Patent
Frazier et al.

(10) Patent No.: US 10,478,157 B2
(45) Date of Patent: Nov. 19, 2019

(54) METHODS FOR DRUG DELIVERY

(71) Applicant: Presage Biosciences, Inc., Seattle, WA (US)

(72) Inventors: Jason Frazier, Bothell, WA (US); Richard Klinghoffer, Seattle, WA (US); Marc Grenley, Seattle, WA (US)

(73) Assignee: PRESAGE BIOSCIENCES, INC., Seattle, WA (US)

( * ) Notice: Subject to any disclaimer, the term of this patent is extended or adjusted under 35 U.S.C. 154(b) by 0 days.

(21) Appl. No.: 15/362,627

(22) Filed: Nov. 28, 2016

(65) Prior Publication Data
US 2017/0296154 A1    Oct. 19, 2017

Related U.S. Application Data

(63) Continuation of application No. 14/328,132, filed on Jul. 10, 2014, which is a continuation of application
(Continued)

(51) Int. Cl.
*A61B 10/00* (2006.01)
*A61M 5/145* (2006.01)
(Continued)

(52) U.S. Cl.
CPC .............. *A61B 10/00* (2013.01); *A61B 10/02* (2013.01); *A61K 31/4745* (2013.01);
(Continued)

(58) Field of Classification Search
CPC .... A61B 10/00; A61B 10/02; A61K 31/4745; A61K 49/0017; A61M 5/00;
(Continued)

(56) References Cited

U.S. PATENT DOCUMENTS 4,014,335 A    3/1977    Arnold
4,164,559 A    8/1979    Dunn et al.
(Continued)

FOREIGN PATENT DOCUMENTS

CA    2696209 A1    2/2009
EP    0774464 A2    5/1997
(Continued)

OTHER PUBLICATIONS

Auman, et al. Cancer pharmacogenomics: DNA genotyping and gene expression profiling to identify molecular determinants of chemosensitivity. Drug Metab Rev. 2008;40(2):303-15. doi: 10.1080/03602530801952427.
(Continued)

*Primary Examiner* — Bradley J Osinski
(74) *Attorney, Agent, or Firm* — Wilson Sonsini Goodrich & Rosati

(57) ABSTRACT

Methods and devices for delivering an agent to a solid tissue in vivo for assessment of efficacy are described. One method involves withdrawing of a needle from and injecting of the agent into the solid tissue; another method involves delivering the agent using a plurality of microdialysis probes to a solid tissue.

29 Claims, 18 Drawing Sheets

Related U.S. Application Data

No. 14/127,763, filed as application No. PCT/US2012/062313 on Oct. 26, 2012.

(60) Provisional application No. 61/680,847, filed on Aug. 8, 2012, provisional application No. 61/553,003, filed on Oct. 28, 2011.

(51) Int. Cl.

| | |
|---|---|
| *A61M 5/00* | (2006.01) |
| *A61B 10/02* | (2006.01) |
| *A61K 31/4745* | (2006.01) |
| *A61K 49/00* | (2006.01) |
| *A61M 5/42* | (2006.01) |
| *G01N 33/50* | (2006.01) |
| *A61M 37/00* | (2006.01) |

(52) U.S. Cl.
CPC ........... *A61K 49/0017* (2013.01); *A61M 5/00* (2013.01); *A61M 5/1452* (2013.01); *A61M 5/427* (2013.01); *G01N 33/5011* (2013.01); *A61M 37/0015* (2013.01)

(58) Field of Classification Search
CPC ................ A61M 5/1452; A61M 5/427; A61M 37/0015; G01N 33/5011
See application file for complete search history.

(56) References Cited

U.S. PATENT DOCUMENTS

| | | | |
|---|---|---|---|
| 4,256,153 A | 3/1981 | Lamaziere | |
| 4,673,565 A | 6/1987 | Di Luccio et al. | |
| 4,897,268 A | 1/1990 | Tice et al. | |
| 4,936,835 A | 6/1990 | Haaga | |
| 4,966,159 A | 10/1990 | Maganias | |
| 5,075,109 A | 12/1991 | Tice et al. | |
| 5,104,620 A | 4/1992 | Wiley et al. | |
| 5,154,181 A | 10/1992 | Fishman | |
| 5,250,023 A | 10/1993 | Lee et al. | |
| 5,335,670 A | 8/1994 | Fishman | |
| 5,457,041 A | 10/1995 | Ginaven et al. | |
| 5,474,909 A * | 12/1995 | Connors ............ | G01N 33/5011 435/29 |
| 5,536,267 A | 7/1996 | Edwards et al. | |
| 5,538,134 A | 7/1996 | Pitesky | |
| 5,693,341 A | 12/1997 | Schroeder et al. | |
| 5,735,288 A | 4/1998 | Fishman | |
| 5,751,629 A | 5/1998 | Nova et al. | |
| 5,789,172 A | 8/1998 | Still et al. | |
| 5,797,898 A | 8/1998 | Santini, Jr. et al. | |
| 5,798,035 A | 8/1998 | Kirk et al. | |
| 5,832,878 A | 11/1998 | Bonsall et al. | |
| 5,846,225 A | 12/1998 | Rosengart et al. | |
| 5,865,766 A | 2/1999 | Bonsall et al. | |
| 5,876,380 A | 3/1999 | Manganini et al. | |
| 5,885,769 A | 3/1999 | Kumar | |
| 5,993,434 A | 11/1999 | Dev et al. | |
| 6,146,594 A | 11/2000 | De Graaff et al. | |
| 6,208,893 B1 | 3/2001 | Hofmann | |
| 6,286,455 B1 | 9/2001 | Williams | |
| 6,330,479 B1 | 12/2001 | Stauffer | |
| 6,428,504 B1 | 8/2002 | Riaziat et al. | |
| 6,468,247 B1 | 10/2002 | Zamoyski | |
| 6,482,187 B1 | 11/2002 | Gibbs | |
| 6,558,361 B1 | 5/2003 | Yeshurun | |
| 6,685,913 B1 | 2/2004 | Thakur et al. | |
| 6,706,947 B2 | 3/2004 | Turner | |
| 6,904,309 B2 | 6/2005 | Derendorf et al. | |
| 6,972,013 B1 | 12/2005 | Zhang et al. | |
| 7,030,097 B1 | 4/2006 | Saltzman et al. | |
| 7,141,234 B1 * | 11/2006 | Collins ............... | A61K 51/0417 424/9.2 |
| 7,226,439 B2 | 6/2007 | Prausnitz et al. | |
| 7,563,584 B2 | 7/2009 | Perez et al. | |
| 7,575,868 B2 | 8/2009 | Kornblith et al. | |
| 7,621,895 B2 | 11/2009 | Willis et al. | |
| 7,627,938 B2 | 12/2009 | Kim et al. | |
| 7,691,085 B2 | 4/2010 | Dedig et al. | |
| 7,711,409 B2 | 5/2010 | Keppel et al. | |
| 7,846,488 B2 | 12/2010 | Johnson et al. | |
| 7,905,854 B2 | 3/2011 | Hazut et al. | |
| 7,922,672 B2 | 4/2011 | Hein et al. | |
| 7,935,086 B2 | 5/2011 | Lafferty et al. | |
| 8,349,554 B2 | 1/2013 | Bahrami et al. | |
| 8,475,412 B2 | 7/2013 | Bahrami et al. | |
| 8,475,417 B2 | 7/2013 | Powers et al. | |
| 8,657,786 B2 | 2/2014 | Bahrami et al. | |
| 8,672,887 B2 | 3/2014 | Bahrami et al. | |
| 8,834,428 B2 | 9/2014 | Bahrami et al. | |
| 8,926,567 B2 | 1/2015 | Bahrami et al. | |
| 9,205,201 B2 | 12/2015 | Bahrami et al. | |
| 9,205,202 B2 | 12/2015 | Bahrami et al. | |
| 2001/0053891 A1 | 12/2001 | Ackley | |
| 2002/0010439 A1 | 1/2002 | Miller | |
| 2002/0031473 A1 | 3/2002 | Perez-Soler | |
| 2002/0082546 A1 | 6/2002 | Crank et al. | |
| 2002/0087209 A1 | 7/2002 | Edwin et al. | |
| 2003/0060780 A1 | 3/2003 | Shu | |
| 2003/0069543 A1 | 4/2003 | Carpenter et al. | |
| 2003/0069560 A1 | 4/2003 | Adamis et al. | |
| 2003/0134810 A1 | 7/2003 | Springate et al. | |
| 2003/0162715 A1 | 8/2003 | Duan et al. | |
| 2004/0039429 A1 * | 2/2004 | Daniel ............... | A61B 18/1477 607/100 |
| 2004/0064098 A1 | 4/2004 | Cuschieri et al. | |
| 2004/0138622 A1 | 7/2004 | Palasis | |
| 2004/0265354 A1 | 12/2004 | Ameri et al. | |
| 2005/0000514 A1 | 1/2005 | Sullivan et al. | |
| 2005/0096586 A1 | 5/2005 | Trautman et al. | |
| 2005/0126304 A1 | 6/2005 | Sparks et al. | |
| 2005/0165342 A1 | 7/2005 | Odland | |
| 2005/0177118 A1 | 8/2005 | Hoganson et al. | |
| 2005/0187303 A1 | 8/2005 | Wu et al. | |
| 2005/0203464 A1 | 9/2005 | Haider et al. | |
| 2006/0014157 A1 | 1/2006 | Kawabe et al. | |
| 2006/0015058 A1 | 1/2006 | Kellogg et al. | |
| 2006/0024358 A1 | 2/2006 | Santini, Jr. et al. | |
| 2006/0058966 A1 | 3/2006 | Bruckner | |
| 2006/0079846 A1 | 4/2006 | Williams | |
| 2006/0084943 A1 | 4/2006 | Rosenman et al. | |
| 2006/0094046 A1 | 5/2006 | Abo et al. | |
| 2006/0206950 A1 | 9/2006 | Kaelin, Jr. | |
| 2006/0259006 A1 | 11/2006 | McKay et al. | |
| 2007/0010810 A1 | 1/2007 | Kochamba | |
| 2007/0021717 A1 | 1/2007 | Gabel et al. | |
| 2007/0036855 A1 | 2/2007 | Domb et al. | |
| 2007/0038181 A1 * | 2/2007 | Melamud ........... | A61B 17/3478 604/158 |
| 2007/0093748 A1 | 4/2007 | Nayak et al. | |
| 2007/0142842 A1 | 6/2007 | Krueger et al. | |
| 2007/0162110 A1 | 7/2007 | Dave | |
| 2007/0191490 A1 | 8/2007 | Sebti | |
| 2007/0238985 A1 | 10/2007 | Smith et al. | |
| 2007/0239099 A1 | 10/2007 | Goldfarb et al. | |
| 2007/0254041 A1 | 11/2007 | Drapeau et al. | |
| 2007/0275434 A1 * | 11/2007 | Mor ................... | G01N 33/5011 435/29 |
| 2007/0283453 A1 | 12/2007 | Rodriguez Cimadevilla et al. | |
| 2007/0287952 A1 | 12/2007 | Shah et al. | |
| 2008/0009802 A1 | 1/2008 | Lambino et al. | |
| 2008/0015494 A1 | 1/2008 | Santini, Jr. et al. | |
| 2008/0140026 A1 | 6/2008 | Sliwa et al. | |
| 2008/0167601 A1 | 7/2008 | Laermer et al. | |
| 2008/0214987 A1 | 9/2008 | Xu | |
| 2008/0269666 A1 | 10/2008 | Wang et al. | |
| 2008/0269685 A1 | 10/2008 | Singh et al. | |
| 2009/0012603 A1 | 1/2009 | Xu et al. | |
| 2009/0093871 A1 | 4/2009 | Rea et al. | |
| 2009/0105562 A1 | 4/2009 | Chiou et al. | |
| 2009/0149897 A1 | 6/2009 | Dacey, Jr. et al. | |
| 2009/0234322 A1 | 9/2009 | Fischer | |
| 2009/0270834 A1 | 10/2009 | Nisato et al. | |

(56) References Cited

U.S. PATENT DOCUMENTS

| | | |
|---|---|---|
| 2010/0029763 A1 | 2/2010 | Suarez et al. |
| 2010/0100005 A1 | 4/2010 | Mir et al. |
| 2010/0119580 A1 | 5/2010 | Guo et al. |
| 2010/0196439 A1 | 8/2010 | Beck et al. |
| 2010/0209477 A1 | 8/2010 | Butuner et al. |
| 2010/0262001 A1 | 10/2010 | Morris et al. |
| 2010/0284927 A1 | 11/2010 | Lu et al. |
| 2010/0291592 A1 | 11/2010 | Semba |
| 2010/0330589 A1 | 12/2010 | Bahrami et al. |
| 2011/0027181 A1 | 2/2011 | Amodei et al. |
| 2011/0150919 A1 | 6/2011 | Reed et al. |
| 2011/0230736 A1 | 9/2011 | Tepper et al. |
| 2011/0230839 A1 | 9/2011 | Bahrami et al. |
| 2012/0087866 A1 | 4/2012 | Bahrami et al. |
| 2012/0089095 A1 | 4/2012 | Bahrami et al. |
| 2012/0094866 A1 | 4/2012 | Bahrami et al. |
| 2012/0109104 A1 | 5/2012 | Bahrami et al. |
| 2012/0121514 A1 | 5/2012 | Bahrami et al. |
| 2012/0265064 A1 | 10/2012 | Bahrami et al. |
| 2012/0296206 A1 | 11/2012 | Bahrami et al. |
| 2013/0184593 A1 | 7/2013 | Tepper et al. |
| 2013/0280755 A1 | 10/2013 | Hubert |
| 2014/0114279 A1 | 4/2014 | Klinghoffer |
| 2014/0162360 A1 | 6/2014 | Bahrami et al. |
| 2014/0162901 A1 | 6/2014 | Bahrami et al. |
| 2014/0170072 A1 | 6/2014 | Klinghoffer et al. |
| 2014/0309590 A1 | 10/2014 | Bahrami et al. |
| 2014/0323907 A1 | 10/2014 | Frazier et al. |
| 2014/0378944 A1 | 12/2014 | Frazier et al. |
| 2018/0256754 A1 | 9/2018 | Klinghoffer et al. |
| 2018/0272078 A1 | 9/2018 | Bahrami et al. |

FOREIGN PATENT DOCUMENTS

| | | |
|---|---|---|
| JP | S63315064 A | 12/1988 |
| JP | H01122758 U | 8/1989 |
| JP | H01502718 A | 9/1989 |
| JP | 2632367 B2 | 7/1997 |
| JP | H10503959 A | 4/1998 |
| JP | 2000513725 A | 10/2000 |
| JP | 2001509668 A | 7/2001 |
| JP | 2003290343 A | 10/2003 |
| JP | 2004504120 A | 2/2004 |
| JP | 2005525141 A | 8/2005 |
| JP | 2006239260 A | 9/2006 |
| JP | 2007130028 A | 5/2007 |
| JP | 2009528131 A | 8/2009 |
| JP | 2011506630 A | 3/2011 |
| WO | WO-9200091 A1 | 1/1992 |
| WO | WO-9209300 A1 | 6/1992 |
| WO | WO-9407553 A1 | 4/1994 |
| WO | WO-9516918 A1 | 6/1995 |
| WO | WO-9604860 A1 | 2/1996 |
| WO | WO-9714459 A1 | 4/1997 |
| WO | WO-0005339 A1 | 2/2000 |
| WO | WO-0006670 A1 | 2/2000 |
| WO | WO-0006770 A1 | 2/2000 |
| WO | WO-0056381 A1 | 9/2000 |
| WO | WO-0056395 A1 | 9/2000 |
| WO | WO-0074766 A1 | 12/2000 |
| WO | WO-03075978 A2 | 9/2003 |
| WO | WO-2004012791 A2 | 2/2004 |
| WO | WO-2006128034 A1 | 11/2006 |
| WO | WO-2007016529 A2 | 2/2007 |
| WO | WO-2007030367 A2 | 3/2007 |
| WO | WO-2007016529 A3 | 4/2007 |
| WO | WO-2007103070 A2 | 9/2007 |
| WO | WO-2008008845 A2 | 1/2008 |
| WO | WO-2008008845 A3 | 4/2008 |
| WO | WO-2008072229 A2 | 6/2008 |
| WO | WO-2007103070 A3 | 8/2008 |
| WO | WO-2009023798 A2 | 2/2009 |
| WO | WO-2009023798 A3 | 5/2009 |
| WO | WO-2010022252 A2 | 2/2010 |
| WO | WO-2010064251 A1 | 6/2010 |

OTHER PUBLICATIONS

Cespedes, et al. Mouse models in oncogenesis and cancer therapy. Clin Transl Oncol. May 2006;8(5):318-29.

City of Hope. Brain Tumor Research. Available at http://www.cityofhope.org/PATIENT_CARE/TREATMENTS/BRAIN-TUMORS/Pages/research-and-clinical-trials.aspx. Accessed May 3, 2010.

Durand. Distribution and activity of antineoplastic drugs in a tumor model. J Natl Cancer Inst. Jan. 18, 1989;81(2):146-52.

Durand. Flow cytometry studies of intracellular adriamycin in multicell spheroids in vitro. Cancer Res. Sep. 1981;41(9 Pt 1):3495-8.

European search report and opinion dated Mar. 31, 2015 for EP Application No. 12843523.7.

European Search report and search opinion for European application No. 08797923.3, Search report dated Feb. 1, 2011.

Gavet, et al. The stathmin phosphoprotein family: intracellular localization and effects on the microtubule network. Cell Sci. Nov. 1998;111 ( Pt 22):3333-46.

Hanahan, D, et al, "The hallmarks of cancer", Cell, vol. 100, No. 1, pp. 57-70, (2000).

Ignatiadis, et al. Understanding the molecular basis of histologic grade. Pathobiology. 2008;75(2):104-11. doi: 10.1159/000123848. Epub Jun. 10, 2008.

Inovio. Intramuscular Delivery. Available at http://www.inovio.com/technology/intramusculardelivery.htm. Accessed Mar. 19, 2010.

International search report and written opinion dated Apr. 19, 2013 for PCT/US2012/062313.

International search report dated Apr. 6, 2009 for PCT Application No. US2008/73212.

Kerbel. Human tumor xenografts as predictive preclinical models for anticancer drug activity in humans: better than commonly perceived—but they can be improved. Cancer Biol Ther. Jul.-Aug. 2003;2(4 Suppl 1):S134-9.

Kerr, et al. Aspects of cytotoxic drug penetration, with particular reference to anthracyclines. Cancer Chemother Pharmacol. 1987;19(1):1-5.

Kunz. Genomic signatures for individualized treatment of malignant tumors. r Drug Discov Technol. Mar. 2008;5(1):9-14.

Laske, et al. Efficacy of direct intratumoral therapy with targeted protein toxins for solid human gliomas in nude mice. J Neurosurg. Mar. 1994;80(3):520-6.

Lin, et al. Ablation of liver tumor by injection of hypertonic saline. AJR Am J Roentgenol. Jan. 2005;184(1):212-9.

Man, et al. On the development of models in mice of advanced visceral metastatic disease for anti-cancer drug testing. Cancer Metastasis Rev. Dec. 2007;26(3-4):737-47.

Muller, et al. In vivo drug-response measurements in target tissue by microdialysis. Clin. Pharmcol. Ther. 1997; 62:165-170.

Muller. Microdialysis in clinical drug delivery studies. Advanced Drug Delivery Reviews. 2000; 45:255-269.

Nederman, et al. Penetration of substances into tumor tissue—a methodological study on cellular spheroids. In Vitro. Apr. 1981;17(4):290-8.

Notice of allowance dated Nov. 28, 2012 for U.S. Appl. No. 12/674,146.

Notice of allowance dated Mar. 4, 2013 for U.S. Appl. No. 13/329,701.

Notice of allowance dated Jun. 6, 2014 for U.S. Appl. No. 13/330,044.

"Notice of allowance dated Sep. 8, 2015 for U.S. Appl. No. 14/178,045.".

"Notice of allowance dated Sep. 15, 2015 for U.S. Appl. No. 14/178,060.".

Notice of allowance dated Oct. 8, 2014 for U.S. Appl. No. 13/330,124.

Notice of Allowance dated Oct. 10, 2013 for U.S. Appl. No. 13/330,022.

Notice of allowance dated Oct. 11, 2013 for U.S. Appl. No. 13/330,106.

Office action dated Feb. 27, 2015 for U.S. Appl. No. 14/178,045.

Office action dated Mar. 1, 2013 for U.S. Appl. No. 13/330,124.

Office action dated Mar. 3, 2015 for U.S. Appl. No. 14/178,060.

Office action dated Mar. 4, 2013 for U.S. Appl. No. 13/330,022.

Office action dated Mar. 27, 2014 for U.S. Appl. No. 13/330,044.

Office action dated Apr. 11, 2013 for U.S. Appl. No. 13/330,106.

(56) References Cited

OTHER PUBLICATIONS

Office action dated Jun. 28, 2016 for U.S. Appl. No. 14/328,132.
Office action dated Jul. 1, 2014 for U.S. Appl. No. 13/330,124.
Office action dated Jul. 2, 2015 for U.S. Appl. No. 13/489,594.
"Office action dated Aug. 13, 2015 for U.S. Appl. No. 14/127,763.".
Office action dated Oct. 4, 2013 for U.S. Appl. No. 13/330,044.
Office action dated Oct. 8, 2013 for U.S. Appl. No. 13/330,124.
Office action dated Oct. 8, 2014 for U.S. Appl. No. 14/178,045.
Office action dated Oct. 9, 2014 for U.S. Appl. No. 14/178,060.
Office action dated Oct. 12, 2012 for U.S. Appl. No. 13/048,721.
Office action dated Oct. 17, 2011 for U.S. Appl. No. 13/048,721.
Procter & Gamble. Inexpensive Micro-Needle Array for Drug Delivery, Biological Sensing. Available at http://www.yet2.com/app/insight/techofweek/30761?sid=350. Accessed Mar. 19, 2010.
Ronquist, et al. Treatment of malignant glioma by a new therapeutic principle. Acta Neurochir (wien). 1992; 114:8-11.
Search report dated Nov. 11, 2010 for GB Application No. GB1004138.2.
Sharma, et al. Intra-tumoral injection of CpG results in the inhibition of tumor growth in murine Colon-26 and B-16 tumors. Biotechnol Lett. Jan. 2003;25(2):149-53.
Sheu, et al. Small hepatocellular carcinoma: intratumor ethanol treatment using new needle and guidance systems. Radiology. Apr. 1987;163(1):43-8.
Shibata, et al. In situ hybridization and immunohistochemistry of bone sialoprotein and secreted phosphoprotein 1 (osteopontin) in the developing mouse mandibular condylar cartilage compared with limb bud cartilage. J Anat. Mar. 2002;200(Pt 3):309-20.
Talmadge, et al. Murine models to evaluate novel and conventional therapeutic strategies for cancer. Am J Pathol. Mar. 2007;170(3):793-804.
Third party observations dated Aug. 29, 2014 against EP Application No. 08797923.3.
Tunggal, et al. Penetration of anticancer drugs through solid tissue: a factor that limits the effectiveness of chemotherapy for solid tumors. Clin Cancer Res. Jun. 1999;5(6):1583-6.
Veiseh, et al. Tumor paint: a chlorotoxin:Cy5.5 bioconjugate for intraoperative visualization of cancer foci. Cancer Res. Jul. 15, 2007;67(14):6882-8.
Victor-g.com. Cass needle—Bent/Straight. Available at http://www.victor-g.com/irrigation_needles.htm#Cass. Accessed May 3, 2010.
Victor-g.com. Irrigation/side port needles. Available at http://www.victor-g.com/irrigation_needles.htm. Accessed May 3, 2010.
Weissleder, et al. In vivo imaging of tumors with protease-activated near-infrared fluorescent probes. Nat Biotechnol. Apr. 1999;17(4):375-8.
World Wide Medical Technologies. Our products: Bone marrow systems. Available at http://www.wwmedtech.com/aspircore.php. Accessed May 3, 2010.
Bild, A.H., et al., Oncogenic pathway signatures in human cancers as a guide to targeted therapies. Nature, 2006. 439(7074): p. 353-7.
Blum, R., et al., Gene expression signature of human cancer cell lines treated with the ras inhibitor salirasib (S-farnesylthiosalicylic acid). Cancer Res, 2007. 67(7): p. 3320-8.
Canadian Office Action dated Aug. 24, 2017 for Canadian Patent Application No. 2941187.
Deininger, M., E. Buchdunger, and B.J. Druker, The development of imatinib as a therapeutic agent for chronic myeloid leukemia. Blood, 2005. 105(7): p. 2640-53.
Engelman, J.A. and P.A. Janne, Mechanisms of acquired resistance to epidermal growth factor receptor tyrosine kinase inhibitors in non-small cell lung cancer. Clin Cancer Res, 2008. 14(10): p. 2895-9.
"European search report and opinion dated Dec. 11, 2015 for EP Application No. 11843742.5.".
European search report and search opinion dated Sep. 1, 2014 for European Application No. 14166779.
Guo, W., et al., Beta 4 integrin amplifies ErbB2 signaling to promote mammary tumorigenesis. Cell, 2006. 126(3): p. 489-502.
International search report and written opinion dated Apr. 3, 2012 for PCT Application No. US2011/062046.
International search report and written opinion dated May 30, 2012 for PCT Application No. US2011/062128.
Jones, H.E., et al., Growth factor receptor interplay and resistance in cancer. Endocr Relat Cancer, 2006. 13 Suppl 1: p. S45-51.
Kass, L., et al., Mammary epithelial cell: influence of extracellular matrix composition and organization during development and tumorigenesis. Int J Biochem Cell Biol, 2007. 39(11): p. 1987-94.
Kotin. Prospects for the use of adeno-associated virus as a vector for human gene therapy. Hum Gene Ther. 5(7):793-801 (1994).
Levental, K.R., et al., Matrix crosslinking forces tumor progression by enhancing integrin signaling. Cell, 2009. 139(5): p. 891-906.
McLaughlin et al. Adeno-Associated Virus General Transduction Vectors: Analysis of Proviral Structures. J Virol 62:1963-1973 (1988).
Medico, E., et al., A gene trap vector system for identifying transcriptionally responsive genes. Nat Biotechnol, 2001. 19(6): p. 579-82.
Muzyczka et al. Use of Adeno-Associated Virus as a General Transduction Vector for Mammalian Cells. Curr Top Microbiol Immunol 158:97-129 (1992).
Office action dated Apr. 18, 2016 for U.S. Appl. No. 14/097,629.
Office action dated May 16, 2017 for U.S. Appl. No. 13/637,274.
Office action dated Jun. 3, 2016 for U.S. Appl. No. 13/988,309.
Office action dated Jul. 20, 2016 for U.S. Appl. No. 13/637,274.
"Office action dated Sep. 29, 2015 for U.S. Appl. No. 14/097,629.".
"Office action dated Oct. 9, 2015 for U.S. Appl. No. 13/988,309.".
Pao, W., et al., Acquired resistance of lung adenocarcinomas to gefitinib or erlotinib is associated with a second mutation in the EGFR kinase domain. PLoS Med, 2005. 2(3): p. e73.
Paszek, et al., Tensional homeostasis and the malignant phenotype. Cancer Cell, 2005. 8(3): p. 241-254.
Press, et al. Xenografts of primary human gynecological tumors grown under the renal capsule of NOD/SCID mice show genetic stability during serial transplantation and respond to cytotoxic chemotherapy. Gynecol Oncol. Aug. 2008;110(2):256-64. doi: 10.1016/j.ygyno.2008.03.011. Epub Jun. 10, 2008.
Santos, E.B., et al., Sensitive in vivo imaging of T cells using a membrane-bound Gaussia princeps luciferase. Nat Med, 2009. 15(3): p. 338-44.
Stenzel et al. Collagen as a Biomaterial. Annual Review of Biophysics and Bioengineering. 1974. vol. 3. pp. 231-253.
Sweet-Cordero, A., et al., An oncogenic KRAS2 expression signature identified by cross-species geneexpression analysis. Nat Genet, 2005. 37(1): p. 48-55.
Tang, E.D., et al., Negative regulation of the forkhead transcription factor FKHR by Akt. J Biol Chem, 1999. 274(24): p. 16741-6.
Tannous, B.A., et al., Codon-optimized Gaussia luciferase cDNA for mammalian gene expression in culture and in vivo. Mol Ther, 2005. 11(3): p. 435-43.
Von Hoff, D.D., There are no bad anticancer agents, only bad clinical trial designs—twenty-first Richard and Hinda Rosenthal Foundation Award Lecture. Clin Cancer Res, 1998. 4(5): p. 1079-86.
Weigelt, B. and M.J. Bissell, Unraveling the microenvironmental influences on the normal mammary gland and breast cancer. Semin Cancer Biol, 2008. 18(5): p. 311-21.
Weigelt, B., et al., HER2 signaling pathway activation and response of breast cancer cells to HER2-targeting agents is dependent strongly on the 3D microenvironment. Breast Cancer Res Treat. 2009. 122:35-43.
Yan, et al., Indexing TNF-alpha gene expression using a gene-targeted reporter cell line. BMC Biol, 2009. 7: p. 8.
Office action dated Feb. 24, 2016 for U.S. Appl. No. 14/178,022.
Office action dated Mar. 23, 2016 for U.S. Appl. No. 13/489,324.
Office action dated Apr. 19, 2016 for U.S. Appl. No. 13/489,594.
Office action dated Jun. 17, 2016 for U.S. Appl. No. 14/127,763.

\* cited by examiner

13a

13b

METHODS FOR DRUG DELIVERY

CROSS-REFERENCE

This application is a continuation of U.S. application Ser. No. 14/328,132, filed Jul. 10, 2014, which is a continuation of U.S. application Ser. No. 14/127,763, filed Dec. 19, 2013, which is a national stage application of PCT/US2012/62313, filed Oct. 26, 2012, which claims the benefit of U.S. Provisional Application 61/680,847, filed Aug. 8, 2012, and U.S. Provisional Application 61/553,003, filed Oct. 28, 2011, the contents of which are incorporated by reference in their entirety.

STATEMENT REGARDING FEDERALLY SPONSORED RESEARCH OR DEVELOPMENT

This invention was made with support of the United States government under grant No. 5R42CA144104-03 awarded by the National Institutes of Health. The government has certain rights in the invention.

BACKGROUND OF THE INVENTION

Numerous cancer-related therapeutics are under preclinical, phase I or phase II clinical trial and evaluations at any particular time; however, most of them will fail to advance. In fact, numerous drug candidates fail in the preclinical test, and it is estimated that more than 90% of cancer-related therapeutics will fail phase I or II clinical trial evaluation. The failure rate in phase III trials is almost 50%, and the cost of new drug development from discovery through phase III trials is between $0.8 billion and $1.7 billion and can take between eight and ten years.

In addition, many subjects fail to respond even to standard drugs that have been shown to be efficacious. For reasons that are not currently well understood or easily evaluated, individual subjects may not respond to standard drug therapy. One significant challenge in the field of oncology is to exclude treatment selection for individual subjects having cell autonomous resistance to a candidate drug to reduce the risk of unnecessary side effects. A related problem is that excessive systemic concentrations are required for many oncology drug candidates in efforts to achieve a desired concentration at a tumor site, an issue compounded by poor drug penetration in many under-vascularized tumors (Tunggal et al., 1999 *Clin. Canc. Res.* 5:1583).

The present invention addresses these and similar needs, and offers other related advantages.

SUMMARY OF THE INVENTION

In one aspect, the present disclosure provides a method of delivering a plurality of agents to a solid tissue of a subject, comprising:
(a) inserting a plurality of microdialysis probes to the solid tissue; and
(b) delivering the plurality of agents to said solid tissue through the plurality of microdialysis probes. The method may further comprise evaluating at least one effect of the plurality of agents on the solid tissue.

In another aspect, the present disclosure provides a method of delivering two or more agents to a solid tissue of a subject, comprising: (a) administering at least one of said two or more agents to said subject systemically; and (b) delivering at least one of said two or more agents to said solid tissue with at least one microdialysis probe or at least one needle, wherein said agent(s) administered in (a) is different from said agent(s) delivered in (b). In some case, step (a) is performed prior to step (b). In some other cases, step (a) is performed after step (b). The method may further comprise evaluating at least one effect of the agents on the solid tissue.

In some embodiments, the agent(s) delivered in (a) or (b) is selected from the group consisting of an anti-angiogenic agent, a kinase inhibitor, an inhibitor of metabolic pathway targets that are preferentially expressed in cancer cells, or an epigenetic modifier. In some other embodiments, the agent(s) delivered in (a) or (b) comprises a small molecule anti-cancer agent. In some embodiments, the agent(s) delivered in (a) comprises an antibody or antibody drug conjugate. In some embodiments, the agent(s) delivered in (b) comprises a small interfering RNA, an antisense RNA or a small molecule anti-cancer agent. At least one of the agents delivered in step (b) may be delivered at different concentrations to different regions of the solid tissue. Alternatively, at least one of the agents delivered in step (b) may be delivered in multiple doses to a same region of the solid tissue. The agent(s) administered in step (a) and the agent(s) delivered in step (b) may have a synergistic effect on the solid tissue. The agent(s) may be present at a concentration below the therapeutic effective concentration.

The microdialysis probes may have different shapes. In some embodiments, at least one of the plurality of microdialysis probes is Y-shaped. In a further embodiment, each of the plurality of microdialysis probes is Y-shaped. In some other embodiments, at least one of the plurality of microdialysis probes is linear. In a further embodiment, each of the plurality of microdialysis probes is linear.

The agents may be delivered by diffusing through the microdialysis probes. The diffusion may be driven by concentration gradient (e.g., from a higher concentration to a lower concentration). In some embodiments, the diffusion may be driven by a solubility gradient (e.g., from a less soluble solution to a more soluble solution or from a more soluble solution to a less soluble solution). Alternatively, the diffusion may be driven by active transportation. In some embodiments, the agents are delivered by flowing a solution of the agents through the microdialysis probes. The flow rate may be at least about 0.1 µl/min. In some embodiments, the flow rate is between about 0.1 µl/min and about 10 µl/min. In a further embodiment, the flow rate is between about 1 µl/min and about 2 µl/min. In some other embodiments, the flow rate is about 0.5, 0.8, 1, 1.2, 1.4, 1.6, 1.8, 2.0, 2.2, 2.5 3.0, 3.5, 4.0, 4.5, 5.0, 5.5, 6.0, 6.5, 7.0, 7.5, 8.0, 8.5, 9.0, 9.5, or 10.0 µl/min.

The plurality of agents may flow through the microdialysis probes in a continuous fashion. The flow may be carried out with a peristaltic pump or a syringe pump. The flow may span a pre-determined period of time. The pre-determined period of time may be at least about 1 hour, 2 hours, 3 hours, 4 hours, 6 hours, 12 hours, 18 hours, 24 hours, 36 hours, 48 hours, 72 hours, or 96 hours. The pre-determined period of time may be in a range of about one hour to about one year.

Upon insertion into a solid tissue, at least a portion of the microdialysis probe spanning the solid tissue may comprise a semi-permeable membrane. In some embodiments, the entire section of the microdialysis probe spanning the solid tissue comprises a semi-permeable membrane.

The insertion of microdialysis probes may be directed by an array guide. The insertion of microdialysis probes may be directed by an arthroscopic device. The insertion of microdialysis probes may be carried out with a needle array device. The needle array device may comprise at least two, at least five, or at least ten needles. Each of the needles may be configured to receive one microdialysis probe. The needle array device may further comprise at least one actuator for controlling needle insertion.

In some embodiments, at least three, at least five, or at least ten microdialysis probes are inserted. Each microdialysis probe may contain a different agent. Additionally, at least two microdialysis probes may contain a same agent at a same or different concentrations.

In another aspect, the present disclosure provides a method of delivering one or more agents to a solid tissue, comprising: (a) inserting one or more needles to the solid tissue; and (b) delivering one or more agents to the solid tissue by withdrawing one or more needles from the solid tissue and injecting one or more agents into the solid tissue. The method may further comprise a step of evaluating an effect of one or more agents on the solid tissue.

The needle may be a porous needle or an end port needle. In some embodiments, the needle is a porous needle. In some other embodiments, the needed is an end port needle.

The rate of injecting one or more agents may be at least about 0.1, 0.2, 0.3, 0.4, 0.5, 0.6, 0.8, 1.0, 1.2, 1.5, 1.8, 2.0, 2.5, 3.0, 3.5, 4.0, 4.5, 5.0, 6.0, 7.0, 8.0, 9.0, 10.0, 12.0, 15.0, 20.0 µl/min. In some embodiments, the rate of injecting one or more agents is between about 0.1 µl/min and about 5.0 µl/min. In some other embodiments, the rate of injecting one or more agents is about 0.1, 0.5, 1.0, or 2.0 µl/min.

The rate of withdrawing one or more needles may be at least about 0.1, 0.2, 0.3, 0.4, 0.5, 0.6, 0.7, 0.8, 0.9, 1.0, 1.2, 1.5, 1.8, 2.0, 2.5, 3.0, 3.5, 4.0, 4.5, 5.0, 6.0, 7.0, 8.0, 9.0, 10.0, or 15.0 mm/min. In some embodiments, the rate of withdrawing one or more needles is between about 0.1 mm/min and about 5.0 mm/min. In some other embodiments, the rate of withdrawing one or more needles is about 0.1, about 0.5, about 1.0, or about 2.0 mm/min.

The insertion and withdrawal of needles may be directed by a fixed guide or an arthroscopic device. The fixed guide may comprise a stereotactic device. The withdrawal of needles and injection of agents may be carried out simultaneously or sequentially. In an exemplary embodiment, the withdrawal of needles and injections of agents are carried out simultaneously.

The insertion may be carried out with a needle array device. The needle array device may comprise at least two, at least five, or at least ten needles. The needle array device may comprise a plurality of reservoirs. In some embodiments, the needle array device comprises at least three, at least five, or at least ten reservoirs. Each of the reservoirs may be in a separate fluid communication with a separate needle. Each of the reservoirs may contain a different agent from the agent in any other reservoirs. In some cases, at least two of the reservoirs contain a same agent at different concentrations. The needle array may further comprise an actuator and/or controller. The controller may be operably linked or separated from the actuator. The controller may control the dosage of an agent to be delivered to the solid tissue.

With regard to any one of above mentioned aspects, the agent(s) is either (i) undetectable outside the solid tissue, or (ii) if detectable outside the solid tissue, the agent(s) is present at less than a minimal dose. Alternatively, the agent(s) is introduced in an amount that is less than a minimal dose required to produce a detectable effect in a subject when delivered systemically. Alternatively, the agent(s) is present in the solid tissue at a therapeutically effective concentration. The therapeutically effective concentration in the solid tissue may be achieved by dosing the agent orally.

With regard to any one of above mentioned aspects, the microdialysis probes or the needles may be inserted along an axis. Upon insertion, the agents may be delivered along the axis. The axis may be one of a plurality of parallel axes within the solid tissue. In some embodiments, there are 3, 4, 5, 6, 7, 8, 9, 10, 12, 14, 15, 18, or even 20 parallel axes.

With regard to any one of above mentioned aspects, the solid tissue may comprise a tumor. The tumor may be selected from the group consisting of a benign tumor and a malignant tumor. The tumor may be selected from the group consisting of a primary tumor, an invasive tumor and a metastatic tumor. The tumor may comprise at least one cancer cell selected from the group consisting of a prostate cancer cell, a breast cancer cell, a colon cancer cell, a lung cancer cell, a brain cancer cell, and an ovarian cancer cell. The tumor may comprise a cancer selected from the group consisting of adenoma, adenocarcinoma, squamous cell carcinoma, basal cell carcinoma, small cell carcinoma, large cell undifferentiated carcinoma, chondrosarcoma, and fibrosarcoma. Additionally, the solid tissue may be selected from the group consisting of brain, liver, lung, kidney, prostate, ovary, spleen, lymph node, thyroid, pancreas, heart, skeletal muscle, intestine, larynx, esophagus, and stomach.

With regard to any one of above mentioned aspects, the evaluating may be performed in vitro or in vivo. In some embodiments, the evaluating is selected from the group consisting of histology sectioning; collecting and analyzing at least one biomarker for tumor cell death, cell signal changes, or proliferation/mitotic changes; detecting the effect of said one or more agents on the proliferative gradient or multiple microenvironments of said solid tissue; detecting the activity or toxicity of each of the plurality of agents in separate regions of the solid tissue; detecting the activity or toxicity of one agent at different concentrations on adjacent positions within a solid tissue; and detecting the activity or toxicity of at least two of the plurality of agents in a same region of the solid tissue. When the activity or toxicity of at least two of the plurality of agents in a same region of the solid tissue is detected, the activity or toxicity from different agents may be synergistic or additive. In some other embodiments, the evaluating comprises imaging said solid tissue. The imaging may comprise radiographic imaging, magnetic resonance imaging, positron emission tomography, or biophotonic imaging. The imaging may occur before, during, or after introduction of the agents.

With regard to any one of above mentioned aspects, the plurality of agents may comprise an agent selected from the group consisting of a protein, a peptide, a peptidomimetic, an antibody, a small molecule, a small interfering RNA-encoding polynucleotide, a nanoparticle, a GCMS tag molecule, a gene therapy agent, an antisense RNA-encoding polynucleotide, a fluorescent dye, a positive control, a negative control, a small molecule anti-cancer agent, or a ribozyme-encoding polynucleotide. In some embodiments, the plurality of agents comprise a chemotherapeutic agent. In a further embodiment, the chemotherapeutic agent comprises a small molecule agent. In a still further embodiment, the small molecule agent has a molecular weight of less than $10^3$ daltons. In some other embodiments, the plurality of agents comprise an anti-cancer agent. In some cases, two or more agents are delivered simultaneously to a same region within said solid tissue. In some cases, two or more agents are delivered sequentially through a microdialysis probe to a same region within said solid tissue.

With regard to any one of above mentioned aspects, the method may further comprise marking sites of insertions. In some embodiments, the sites of insertions are marked by residual color markers attached to the probes after delivering the agents. In some other embodiments, the sites of insertions are marked by at least one position marker. In a further embodiment, the at least one position marker comprises a dye. The dye may be a fluorescent dye.

With regard to any one of above mentioned aspects, an agent may be delivered to a same region of the solid tissue in multiple doses. Any two of the multiple doses may be separated by a selected period of time. The selected period of time may be at least about 10 minutes, 20 minutes, 30 minutes, 40 minutes, 60 minutes, 80 minutes, 90 minutes, 120 minutes, 6 hours, 12 hours, 24 hours, 36 hours, 48 hours, 72 hours, or 96 hour. The selected period of time may be in a range of about one hour to about three months.

With regard to any one of above mentioned aspects, the agents may comprise a cancer therapeutic agent and the evaluating may comprise detecting the presence or absence of a drug response and/or at least one biomarkers. Examples of drug response or biomarker may include, but are not limited to, cell apoptosis, downstream protein phosphorylation, gene expression markers, metabolic markers and other IHC markers. Cell apoptosis may be detected in a region of within about 0.001, 0.005, 0.01, 0.05, 0.1, 0.2, 0.5, 1.0, 2.0, 3.0, 4.0 or about 5 mm from the site of delivery. Cell apoptosis may be detected in a region of about 0.001-0.1, 0.1-0.5, 0.5-1.0, or 1.0-5.0 mm from the site of delivery. The threshold for selecting or deselecting of an agent based on cell apoptosis may depend upon the cancer therapeutic agent used and the nature or size of the tumor. In some embodiments, the cancer therapeutic agent is deselected from further evaluation if less than about 1%, about 3%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% cell apoptosis is observed comparing to a control without the cancer therapeutic agent. In some other embodiments, the cancer therapeutic agent is selected for further evaluation if more than about 1%, about 3%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% cell apoptosis is observed comparing to a control without the cancer therapeutic agent.

With regard to any one of above mentioned aspects, the subject may be an animal or a human. Upon evaluating at least one effect of the agent(s) on the solid tissue, the agent(s) may be selected, deselected or prioritized based on the evaluation. In some embodiments, the agent(s) is selected for a clinical trial based on the evaluation. In some other embodiments, the agent(s) is deselected from a clinical trial based on the evaluation. The subject may be one of a plurality of subjects. Upon evaluating at least one effect of the agent(s) on the solid tissue of the plurality of subjects, some subjects may be selected, deselected or prioritized based on the evaluation. In some embodiments, some subjects are selected for a clinical trial of an agent based on the evaluation. In some other embodiments, some subjects are deselected from a clinical trial of an agent based on the evaluation. Non-limiting examples of the effect include the presence or absence of a change of physiological state of the solid tissue and the presence of absence of a biomarker.

In another aspect, the present disclosure provides a device for delivering a plurality of agents to a solid tissue of a subject, comprising a plurality of microdialysis probes. The device may further comprise any one of the followings: (1) a plurality of needles, each configured to receive one of said plurality of microdialysis probes; (2) at least one controller, operatively coupled to said plurality of needles; and (3) a guiding device to guide the insertion of said plurality of needles to said solid tissue. The device may comprise at least 3, 4, 5, 6, or 10 microdialysis probes or needles. In some embodiments, controller is a computer. The computer may be used to control the insertion of microdialysis probe and injection of agents. In some further embodiments, the computer is part of a cloud computing system.

In another aspect, the present invention provides a device, comprising a top block having a first plurality of holes sized to allow a needle to pass through the top block, and a bottom block having a second plurality of holes sized to allow a needle to pass through the bottom block, wherein the top and bottom blocks are in a substantially parallel arrangement and wherein the first and second plurality of holes are positioned so as to allow one or more needles to pass through a hole in the top block and the bottom block in a path substantially vertical to the plane of both blocks. The device may further comprise at least one adjustable leg, wherein the at least one adjustable leg is attached to the bottom block. The number of legs may be at least 1, 2, 3, 4, 5, 6, 7, 8, 9, 10, 12, 14, 16, 18, 20, or even more. In an exemplary embodiment, there are 4 legs. In some embodiments, the legs are vertically and horizontally adjustable. The bottom block and the top block may be independently stationary or movable. In some cases, the bottom block of the device is stationary and the top block can move vertically relative to the bottom block. In some further embodiments, the top block moves along guide rods attached to the bottom block. Movement of any blocks may be controlled. For example, a system may be attached to the device to control vertical movement of the top block.

In some embodiments, the first and second pluralities of holes are arranged in substantially parallel rows. The device may further comprise at least one needle. In some embodiments, a control attachment is attached to the at least one needle. The control attachment may stop the insertion of the at least one needle, thereby controlling depth of needle insertion into the solid tissue. Additionally, the device may further comprise at least one spring, wherein the at least one spring is in substantial contact with an adjustable leg and the bottom block.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

General Overview

Figure 1:
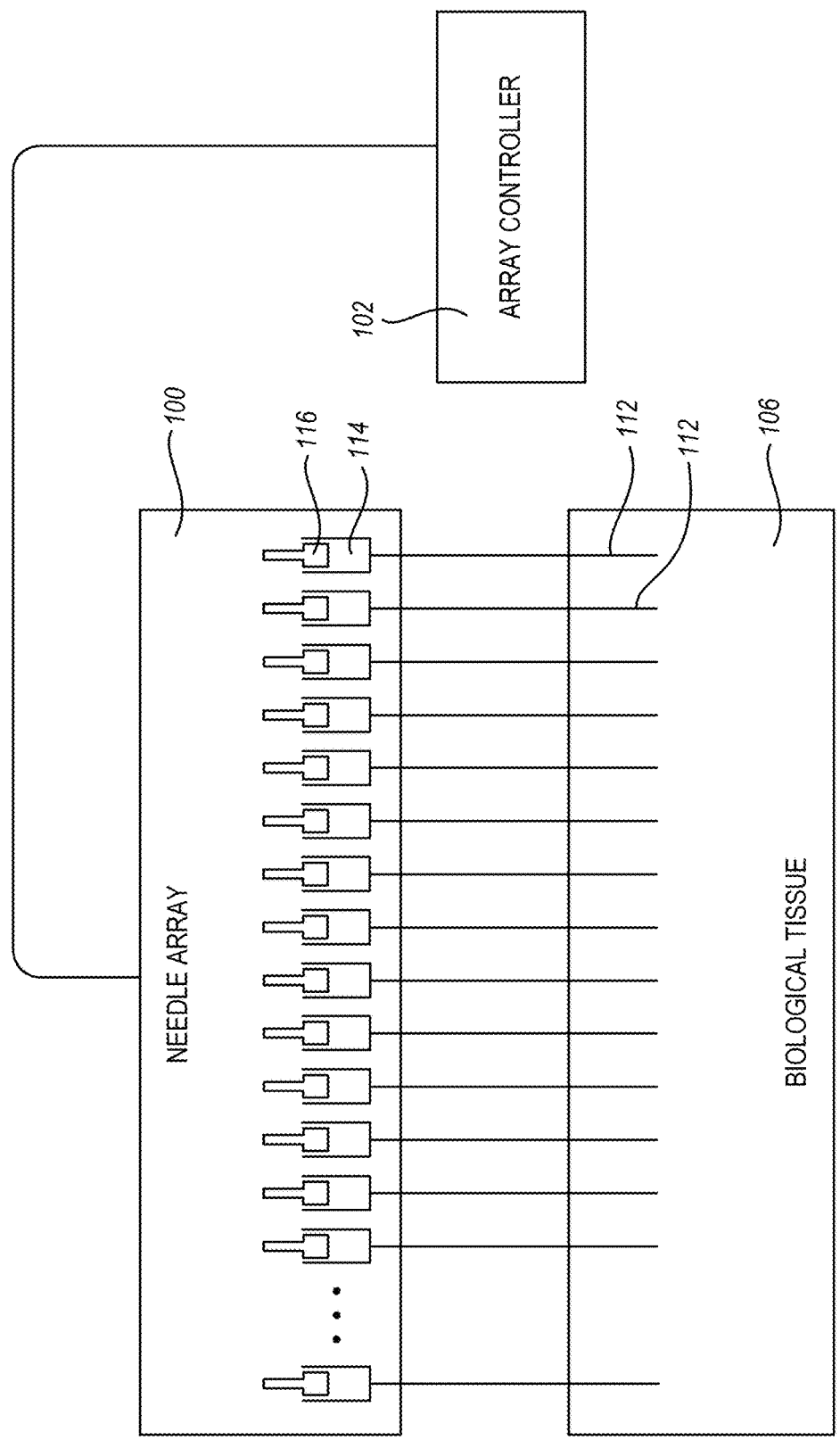
FIG. 1 is a schematic diagram of a needle array assembly for injecting biological tissue with agents according to various embodiments.

Clinical trials for therapeutic agents, including cancer therapeutic agents, are incredibly expensive and time consuming. It is therefore very important to effectively screen for agents that have relatively greater potential as early in the process as possible. Agents subjected to such screening are sometimes referred to as candidate agents. One screening method involves growing tumor cells in an artificial environment on plastic cell culture plates with a growth medium, then placing each candidate agent in a respective cell culture plate or Dish. The cell cultures are later evaluated for indications of cell growth. Agents that appear to have impeded growth of cancer cells and/or engage with a biological target may then be advanced for further study.

However, this method is only marginally effective, for several reasons. First, cell culture poorly mimics tumors growing in a patient. Only the most general information can be gleaned from such studies because the test conditions do not remotely resemble the conditions in which the cancer normally lives and grows, and in which it is treated therapeutically. Screening tests like that described are therefore ineffective with these. Second, the process of immortalizing a tumor for laboratory use can alter the response characteristics of a tumor. The process involves essentially pureeing the tumor, which completely destroys any structural differentiation, and may render the cancer susceptible to some agents that would have no effect on the same strain in vivo, resulting in a false positive, even though such agents might be useless for treating the cancer in patients. Third, the same reduction process can also produce false negatives, in which some agents may fail to inhibit cell growth in vitro, but would be effective in treating the same cancer in vivo. Finally, even where general efficacy of an agent in treating a particular cancer type, subtype, variant, strain or the like has been demonstrated, it is not uncommon for the cancer of a particular patient to be wholly unresponsive to the agent.

The inventors have recognized the need to accurately position an agent and/or control an amount of the agent to be delivered in a solid tissue in vivo and later identify the locations of the agent in the solid tissue. If such accuracy could be achieved, significant benefits in research and therapy could be realized. For example, many tumors are heterogeneous in nature with among other differences, a quiescent inner zone and a proliferative outer zone. It may be important to target the proliferating zone of solid tumors to assess drugs that target mitosis and mitotic checkpoints and/or pathways which are more active in proliferating zones, for example, C-Met and AKT. Therefore, methods allowing evaluation of therapeutic agents across an entire solid tumor may be highly valuable.

The present disclosure provides methods and devices for delivering an agent to a solid tissue, and in particular to a solid tumor in vivo. Often, one or more agents are delivered to a solid tissue with improved accuracy, uniformity and dosage control. Thereafter, the agents remain in the solid tissue for a selected period of time. The effects of the agents on the solid tissue are then monitored in vivo or in vitro. Based on the observed effects, each of the agents is selected or deselected for further studies or consideration of treatment for a patient, on whose solid tissue the candidate drugs have been assessed.

The agents are usually dissolved in solution and delivered to a target site within a solid tissue. The volume of fluid that is delivered can be vanishingly small, much less than would be a minimal dose required to produce a detectable effect in a subject when delivered systemically. Depending on the agent, the effect may nevertheless be detected on the very small region immediately surrounding the delivery site. Accordingly, candidate effective agents can be injected into a tumor, for example, in situ, without danger of harming the subject. Additionally, a significant number of different agents can be simultaneously delivered to respective delivery axes within the tumor.

The procedures described herein can be employed to resolve a number of the problems and difficulties that contribute to the cost and delay of developing effective cancer therapies. For example, because the candidate agents are delivered in vivo, the tumor is not otherwise disturbed and drug concentrations can approximate levels achieved through systemic administration of the drug, and so its reaction to each agent will tend to be indicative of its reaction if exposed to that agent in therapeutically effective quantities. The incidence of false positives and false negatives is significantly reduced. Second, because relatively large numbers of agents can be delivered to a tumor without significant danger to the subject, it is practical to use the procedure to screen large numbers of candidate agents early in the testing process, perhaps eliminating those that show the least promise, flagging the most promising agents for additional study, or prioritizing candidates for further study. Third, again because of the large number of agents that can be delivered to a tumor, potential study subjects can be screened for response to particular agents, reducing or eliminating the number of subjects with idiosyncratic responses. Fourth, because the agents are delivered locally to a solid tissue, systemic exposure of the agent can be avoided.

Accordingly, for example, certain embodiments contemplate direct drug delivery to a solid tissue at low flow rates with low shear forces that eliminate or reduce mechano-chemical damage to tissues while permitting precisely targeted therapeutic agent delivery to defined focal sites. Significantly higher concentrations of the agents may be achieved within the solid tissue than would be the case if the agents were delivered systemically. In other words, the amount of agents required to achieve desired pharmacological effect would be lower, and in some case much lower, than would be the case if the agents were delivered systemically. In some cases, the agents are undetectable outside the solid tissue. In some other cases, less than 10% of the agents are detected outside the solid tissue (e.g., in the systemic circulation). In some other cases, upon delivery, the agents are present in a solid tissue at therapeutically effective concentrations. Therapeutically effective concentrations of the agents in a solid tissue can be achieved by dosing the agents orally. However, systemic exposure of the agents, often at high concentrations, is required. Hence, problems (e.g., toxicity, detrimental side-effects, etc.) associated with administering excessively high systemic concentrations of the agents in order to obtain therapeutically effective concentrations in a desired solid tissue are overcome by the presently disclosed embodiments.

In one aspect, the present disclosure provides methods of delivering and evaluating one or more agents in a solid tissue with one or more microdialysis probes. The number of microdialysis probes inserted may be at least 2, 3, 4, 5, 6, 7, 8, 9, 10, 12, 14, 15, 20, 25 or 30. In some cases, at least some of the microdialysis probes are inserted simultaneously. In some other cases, at least some of the microdialysis probes are inserted sequentially. The microdialysis probes may be inserted along an axis. The axis may be one of a plurality o parallel axis. The number of axes may be at least 3, at least 4, at least 5, at least 6, at least 7, at least 8, at least 9, at least 10, at least 12, or at least 15. The number of axes may be about 3, 4, 5, 6, 7, 8, 9, 10, 12, or 15. After the insertion, the agents may be delivered to the solid tissue by diffusing through the microdialysis probes. The agents may diffuse through the membrane region of the microdialysis probes, thus delivering the agents to a column-shaped region along a delivery axis within the solid tissue.

Each of the microdialysis probes may contain a different agent from any other probes. Alternatively, some of the microdialysis probes may contain a same agent as at least another microdialysis probe. When two or more microdialysis probes contain a same agent in perfusate, concentrations of the agent in different probes may be the same or different.

The agents may be delivered to the solid tissue in a continuous fashion. In some cases, the delivery may last about 10, 20, 30, 40, 50, 60, 70, 80, 90, 100, 110, 120, 130, 140, 150, 160, 170, 180, 200, 220, 240, 260, 280, 300, 320, 340, 360, 400, 450, 500, 550, 600, 650, 700, 750, 800, 850, 900, 1000, 1100, 1200, 1300, 1400, 1500, 1600, 1700, 1800, 2000, 2200, 24000, 2600, 2800, 3000 minutes, 3 days, 4 days, 5 days, 6 days, 1 week, 2 weeks, 3 weeks, 4 weeks, 5 weeks, 6 weeks, 2 months, 3 months, 4 months, 6 months, 8 moths, 9 months, 1 years or 2 years.

The agents may be delivered to the solid tissue in multiple doses. At least two of the multiple doses may be separated by a pre-determined period of time. The pre-detennined period of time may be about 10, 20, 30, 40, 50, 60, 70, 80, 90, 100, 110, 120, 130, 140, 150, 160, 170, 180, 200, 220, 240, 260, 280, 300, 320, 340, 360, 400, 450, 500, 550, 600, 650, 700, 750, 800, 850, 900, 1000, 1100, 1200, 1300, 1400, 1500, 1600, 1700, 1800, 2000, 2200, 24000, 2600, 2800, 3000 minutes, 3 days, 4 days, 5 days, 6 days, 1 week, 2 weeks, 3 weeks, 4 weeks, 5 weeks, 6 weeks, 2 months, 3 months, 4 months, 6 months, 8 moths, 9 months, 1 years or 2 years.

The flow rate of an agent in each microdialysis probe may be independently controlled. The flow rate may be independently at least 0.001 µl/min. In some embodiments, the flow rate is independently in the range of about 0.001 µl/min to about 5 µl/min. In some embodiments, the flow rate is independently about 0.001, 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 µl/min The microdialysis probes may be inserted with a needle array device. The needle array device may contain a plurality of needles. In some cases, the needle array device has 2, 3, 4, 5, 6, 7, 8, 9, 10, 11, 12, 13,14, 15, 16, 17, 18, 19, 20, 21, 22, 23, 24, 25, 26, 27, 28, 29, 30 or even more needles. Each of the needles may be configured to receive at least one microdialysis probe. In some cases, each needle is inserted along one of a plurality of parallel axes. Upon insertion and placement of microdialysis probes in the solid tissue, the needles are then withdrew, leaving behind the microdialysis probes in the solid tissue.

The method may further comprise a step of evaluating an effect of the agents on the solid tissue. In some cases, such evaluation comprises detecting the activity or toxicity of each of the agents in separate regions of the solid tissue. In some other cases, such evaluation comprises detecting the activity or toxicity of two or more of the agents in a same region of the solid tissue. When two or more agents are delivered to a same region, they may be delivered simultaneously or sequentially. In some other cases, such evaluation comprises detecting the activity or toxicity of a same agent with different concentrations in adjacent regions of the solid tissue. In a further embodiment, such evaluation comprises detecting the activity or toxicity of three or more of agents in a same region of the solid tissue.

In another aspect, the present disclosure provides a method of delivering two or more agents to a solid tissue of a subject, comprising: (a) administering at least one of said two or more agents to said subject systemically; and (b) delivering at least one of said two or more agents to said solid tissue with at least one microdialysis probe or at least one needle, wherein said agent(s) administered in (a) is different from said agent(s) delivered in (b). In some case, step (a) is performed prior to steno (b). In some other cases, step (a) is performed after step (b). The method may further comprise a step of evaluating an effect of the agents on the solid tissue. The agent(s) in step (a) may be administered orally or via injection.

In another aspect, the present disclosure provides a method of delivering one or more agents to a solid tissue, comprising: (a) inserting one or more needles to the solid tissue; and (b) delivering the one or more agents to the solid tissue by withdrawing the one or more needles from the solid tissue and injecting the one or more agents into the solid tissue. The method may further comprise evaluating an effect of one or more agents on the solid tissue.

The injection of one or more agents and withdrawal of one or more needles may be carried out sequentially or simultaneously. In some embodiments, the injection of one or more agents and withdrawal of one or more needles are carried out simultaneously. Additionally, since the agents are delivered to an empty space instead of being forced through a solid tissue, the likelihood of agents cross-contamination is much reduced.

The rate of injecting one or more agents and the rate of withdrawal of one or more needles may be separately controlled. The rate of injection may be in a range of 0.1-5.0 μl/min. In some embodiments, the rate of injection is at least about 0.1 μl/min, about 0.2 μl/min, about 0.3 μl/min, about 0.4 μl/min, about 0.5 μl/min, about 0.6 μl/min, about 0.7 μl/min, about 0.8 μl/min, about 0.9 μl/min, about 1.0 μl/min, about 1.1 μl/min, about 1.2 μl/min, about 1.3 μl/min, about 1.4 μl/min, about 1.5 μl/min, about 1.6 μl/min, about 1.7 μl/min, about 1.8 μl/min, about 1.9 μl/min, about 2.0 μl/min, about 2.1 μl/min, about 2.2 μl/min, about 2.3 μl/min, about 2.4 μl/min, about 2.5 μl/min, about 2.6 μl/min, about 2.7 μl/min, about 2.8 μl/min, about 2.9 μl/min, about 3.0 μl/min, about 3.1 μl/min, about 3.2 μl/min, about 3.3 μl/min, about 3.4 μl/min, about 3.5 μl/min, about 3.6 μl/min, about 3.7 μl/min, about 3.8 μl/min, about 3.9 μl/min, about 4.0 μl/min, about 4.1 μl/min, about 4.2 μl/min, about 4.3 μl/min, about 4.4 μl/min, about 4.5 μl/min, about 4.6 μl/min, about 4.7 μl/min, about 4.8 μl/min, about 4.9 μl/min or about 5.0 μl/min. In some other embodiments, the rate of injection is about 0.1 μl/min, about 0.2 μl/min, about 0.3 μl/min, about 0.4 μl/min, about 0.5 μl/min, about 0.6 μl/min, about 0.7 μl/min, about 0.8 μl/min, about 0.9 1 μl/min, about 1.0 μl/min, about 1.1 μl/min, about 1.2 μl/min, about 1.3 μl/min, about 1.4 μl/min, about 1.5 μl/min, about 1.6 μl/min, about 1.7 μl/min, about 1.8 μl/min, about 1.9 μl/min, about 2.0 μl/min, about 2.1 μl/min, about 2.2 μl/min, about 2.3 μl/min, about 2.4 μl/min, about 2.5 μl/min, about 2.6 μl/min, about 2.7 μl/min, about 2.8 μl/min, about 2.9 μl/min, about 3.0 μl/min, about 3.1 μl/min, about 3.2 μl/min, about 3.3 μl/min, about 3.4 μl/min, about 3.5 μl/min, about 3.6 μl/min, about 3.7 μl/min, about 3.8 μl/min, about 3.9 μl/min, about 4.0 μl/min, about 4.1 μl/min, about 4.2 μl/min, about 4.3 μl/min, about 4.4 μl/min, about 4.5 μl/min, about 4.6 μl/min, about 4.7 μl/min, about 4.8 μl/min, about 4.9 μl/min or about 5.0 μl/min. In some other embodiments, the rate of injection is in a range of 0.1-1.0 μl/min, 0.5-1.5 μl/min, 1.0-2.0 μl/min, 2.0-3.0 μl/min, 3.0-4.0 μl/min or 4.0-5.0 μl/min.

The rate of withdrawal of one or more needles may be in a range of 0.1-10 mm/min. In some embodiments, the rate of withdrawal of one or more needles is at least about 0.1 mm/min, about 0.2 mm/min, about 0.3 mm/min, about 0.4 mm/min, about 0.5 mm/min, about 0.6 mm/min, about 0.7 mm/min, about 0.8 mm/min, about 0.9 mm/min, about 1.0 mm/min, about 1.1 mm/min, about 1.2 mm/min, about 1.3 mm/min, about 1.4 mm/min, about 1.5 mm/min, about 1.6 mm/min, about 1.7 mm/min, about 1.8 mm/min, about 1.9 mm/min, about 2.0 mm/min, about 2.1 mm/min, about 2.2 mm/min, about 2.3 mm/min, about 2.4 mm/min, about 2.5 mm/min, about 2.6 mm/min, about 2.7 mm/min, about 2.8 mm/min, about 2.9 mm/min, about 3.0 mm/min, about 3.1 mm/min, about 3.2 mm/min, about 3.3 mm/min, about 3.4 mm/min, about 3.5 mm/min, about 3.6 mm/min, about 3.7 mm/min, about 3.8 mm/min, about 3.9 mm/min, about 4.0 mm/min, about 4.1 mm/min, about 4.2 mm/min, about 4.3 mm/min, about 4.4 mm/min, about 4.5 mm/min, about 4.6 mm/min, about 4.7 mm/min, about 4.8 mm/min, about 4.9 mm/min, about 5.0 mm/min, about 5.1 mm/min, about 5.2 mm/min, about 5.3 mm/min, about 5.4 mm/min, about 5.5 mm/min, about 5.6 mm/min, about 5.7 mm/min, about 5.8 mm/min, about 5.9 mm/min, about 6.0 mm/min, about 6.1 mm/min, about 6.2 mm/min, about 6.3 mm/min, about 6.4 mm/min, about 7.0 mm/min, about 8.0 mm/min, about 9.0 mm/min or 10.0 mm/min. In some other embodiments, the rate of withdrawal of one or more needles is about 0.1 mm/min, about 0.2 mm/min, about 0.3 mm/min, about 0.4 mm/min, about 0.5 mm/min, about 0.6 mm/min, about 0.7 mm/min, about 0.8 mm/min, about 0.9 mm/min, about 1.0 mm/min, about 1.1 mm/min, about 1.2 mm/min, about 1.3 mm/min, about 1.4 mm/min, about 1.5 mm/min, about 1.6 mm/min, about 1.7 mm/min, about 1.8 mm/min, about 1.9 mm/min, about 2.0 mm/min, about 2.1 mm/min, about 2.2 mm/min, about 2.3 mm/min, about 2.4 mm/min, about 2.5 mm/min, about 2.6 mm/min, about 2.7 mm/min, about 2.8 mm/min, about 2.9 mm/min, about 3.0 mm/min, about 3.1 mm/min, about 3.2 mm/min, about 3.3 mm/min, about 3.4 mm/min, about 3.5 mm/min, about 3.6 mm/min, about 3.7 mm/min, about 3.8 mm/min, about 3.9 mm/min, about 4.0 mm/min, about 4.1 mm/min, about 4.2 mm/min, about 4.3 mm/min, about 4.4 mm/min, about 4.5 mm/min, about 4.6 mm/min, about 4.7 mm/min, about 4.8 mm/min, about 4.9 mm/min, about 5.0 mm/min, about 5.1 mm/min, about 5.2 mm/min, about 5.3 mm/min, about 5.4 mm/min, about 5.5 mm/min, about 5.6 mm/min, about 5.7 mm/min, about 5.8 mm/min, about 5.9 mm/min, about 6.0 mm/min, about 6.1 mm/min, about 6.2 mm/min, about 6.3 mm/min, about 6.4 mm/min, about 7.0 mm/min, about 8.0 mm/min, about 9.0 mm/min or 10.0 mm/min. In some other embodiments, the rate of withdrawal of one or more needles is in a range of 0.1-1.0 mm/min, 0.5-1.5 mm/min, 1.0-2.0 mm/min, 1.5-2.5 mm/min, 2.0-3.0 mm/min, 2.5-3.5 mm/min, 3.0-4.0 mm/min, 3.5-4.5 mm/min or 4.0-5.0 mm/min.

In another aspect, the present disclosure provides a device for delivering a plurality of agents to a solid tissue of a subject, comprising a plurality of microdialysis probes. The device may further comprise any one of the followings: (1) a plurality of needles, each configured to receive one of said plurality of microdialysis probes; (2) at least one controller, operatively coupled to said plurality of needles; and (3) a guiding device to guide the insertion of said plurality of needles to said solid tissue. The device may comprise at least 3, 4, 5, 6, or 10 microdialysis probes or needles. In some embodiments, controller is a computer. The computer may be used to control the insertion of microdialysis probe and injection of agents. In some further embodiments, the computer is part of a cloud computing system.

In another aspect, the present invention provides a device for controlling needle insertion into and withdrawal from a solid tissue, comprising: (a) a positioning mechanism; (b) a depth-control mechanism; and (c) a needle withdrawal mechanism.

In yet another aspect, there is provided a device for delivery of at least one agent to a solid tissue, comprising one bottom block and one top block in a substantially parallel arrangement, each having a plurality of holes. The plurality of holes in the bottom and top block may guide the insertion of needles. In some cases, the size of holes may be controlled to allow needles of a certain size to pass through. The device may lead to improved accuracy of needle insertion and exquisite control of delivery of the at least one agent to a solid tissue.

As used herein the term "synergistic activity or toxicity" refers to coordinated activity or toxicity of two or more agents so that the combined action is greater than the sum of each agent acting separately. The coordinated activity or toxicity may be at least about 10%, about 20%, about 30%, about 40%, about 50%, about 60%, about 70%, about 80%, about 90% or even higher than the sum of each agent acting separately.

As used herein the term "additive activity or toxicity" refers to activity or toxicity of two or more agents so that the combined action is about equal to the sum of each agent acting separately.

As used herein the term "about" refers to ±10% and includes ±1% and ±0.1%.

As used herein the term "therapeutically effective concentrations" refers to the concentrations of agents in a solid tissue when a desirable pharmacological effect is observed in the solid tissue. For example, for an anti-cancer drug which is delivered orally, the drug needs to go through an absorption process to get into the systemic circulation. After absorption, the drug then enters or accumulates in the solid tissue. The concentrations of the drug in the solid tissue and in the systemic circulation may be the same or different when a desirable pharmacological effect is observed.

As used herein the term "pre-determined period of time" or "selected period of time" refers to any time within a range of 1 minute to 2 years. In some embodiments, the pre-determined period of time or selected period of time is about 0.1, 0.2, 0.5, 1, 2, 3, 4, 5, 6, 7, 8, 9, 10, 11, 12, 15, 18, 24, 36, 48, 72, 96, 120, 144, 168, or 192 hours. In some other embodiments, the pre-determined period of time or selected period of time is in a range of about 24-72 hours.

Microdialysis Probes

The present invention provides methods for the administration of an agent to a solid tissue through the use of one or more microdialysis probes. In some cases, the microdialysis probe has an inlet-tubing, an outlet-tubing and a membrane region. The solution in the inlet-tubing is termed "perfusate" while the solution in the outlet tubing is termed "dialysate". The inlet- and outlet-tubings may be made of a material suitable for microdialysis application. In some embodiments, the material is fused silica. In some other cases, the microdialysis probe has an inlet-tubing and a membrane region without an outlet-tubing. In this design, an agent may be actively pumped across the membrane region.

The inventors have recognized the advantages of using microdialysis probes as a delivery tool, which include: (1) microdialysis probes are an enclosed system, not dependent upon delivery of a liquid volume, thus eliminating many of the microfluidic engineering hurdles; (2) the semi-permeable membrane surrounding the probe allows liquid to be filled and distributed evenly along probe membrane when injecting into a solid tissue; (3) initial delivery and biodistribution of agents are highly restricted and dependent upon passive diffusion forces, not deposition/delivery of a liquid; (4) true "microdosing" of agents can be achieved by controlling time, flow rate and concentration of perfusate; (5) multiple or timed dosing over an extended periods of time can be achieved by leaving probes in the solid tissue; (6) the amount of agents delivered can be accurately determined by analyzing the amount of agent in perfusate and dialysate; (7) the length of the probe/semi-permeable membrane can be customized to target various size tumors or length of targeting zone within a tumor; (8) an array of linear microdialysis probes can be designed to target the proliferating zone in solid tumor xenografts, as well as avoiding the central regions necrosis; (9) better sampling of multiple zones, including the entire dimension of a solid tumor, to look for efficacy differences using linear probe arrays can be achieved; and (10) collection and analysis of dialysate at various time points following dosing may allow development and analysis of markers of tumor cell death, cell signal changes, or proliferation/mitotic changes. In addition, microdialysis probes can be used to coax contact-inhibited cells into cycling in order to kill them using checkpoint inhibition/DNA damage, or activate cell signal pathways that have been shut down in non-proliferative zones.

A microdialysis probe may be suitable for containing, administering, delivering and transporting contents. The contents may be an aqueous solution comprising a pharmaceutical composition comprising one or more agents. The agents within a single microdialysis probe may be the same or a mixture of different types of agents. Within a plurality of microdialysis probes, each microdialysis probe may contain the same agent as another probe, or different agents as another probe. In some embodiments, every microdialysis probe contains agents that are unique from the agents contained in other microdialysis probes.

A microdialysis probe may have different shapes. In some cases, the microdialysis probe has a "Y" shape. In some other cases, the microdialysis probe has a linear shape. The linear shape may allow the microdialysis probe to penetrate across different sections of a tumor.

The membrane of a microdialysis probe may be semi-permeable. The membrane may permit the transport of some but not all solutes. In some embodiments, the membrane permits the transport of solutes with a molecule weight of less than 1 million Daltons. In a further embodiments, the membrane permits the transport of solutes with a molecule weight in the range of 5,000 Daltons to 1 million Daltons. In another further embodiment, the membrane permits the transport of solutes with a molecule weight of less than 1,000 Daltons.

The movement of a substance or an agent from one side to another side of a membrane may be driven by concentration gradient. In some cases, the movement of a substance or an agent from one side to another side of a membrane is driven only by concentration gradient. A substance or an agent may move from an area of higher concentration to an area of lower concentration through the semi-permeable membrane. In some cases, the agent diffuses from a microdialysis probe into a solid tissue. In some other cases, a solute in a solid tissue diffuses into a microdialysis probe. The solute can be collected and/or analyzed from dialysate. Alternatively, the movement of a substrate or an agent may be driven by active transporter, irrespective of concentration gradient. For example, in nature, some cells use active transporter to accumulate molecules, such as ions, glucose and amino acids. Alternatively, the movement of a substrate or an agent may be driven by solubility difference. The substrate or agent may have a higher solubility on one side of the membrane than the solubility on the other side. In some cases, the substrate or agent moves from a higher concentration side to a lower concentration side. In some embodiments, the substrate or agent moves from a lower concentration side to a higher concentration side. In some cases, the movement of a substance or an agent from one side to another side of a membrane is driven by a combination of any one of concentration gradient, active transportation, and solubility difference.

The membrane may be biocompatible. The membrane may be essentially physiologically inactive or does not trigger physiological events. In some embodiments, the membrane may not cause inflammation, immune response, infection, or any other sort of rejections within a solid tissue.

The membrane may be flexible. The flexibility of the membrane will permit the insertion of the membrane section into the solid tissue with minimal damage to the tissue. Yet, the membrane may have certain strength to maintain its integrity before, during or after the insertion. In some embodiments, the membrane is both flexible and durable.

The membrane material may be polymeric or co-polymeric. The polymeric or co-polymeric material may be linear or cross-linked. Non-limiting examples of membrane materials include PE (polyethylene), Kevlar, cuprophane, polyethersulfone, polyamine, polyamide, polycarbonate, polycarbamate, polyurethane, polyester, polyether, polyolefm, polysilicon oxide, cellulose acetate, and polyaromatic materials.

The membrane material may be porous. In some embodiments, the average pore size is less than about 1, 5, 10, 20, 30, 40, 50, 100, 200, 500, 1000, 2000, 5000, or 10000 nanometers. In some other embodiments, the average pore size is more than about 1, 5, 10, 20, 30, 40, 50, 100, 200, or 500 nanometers. In some other embodiments, the average pore size is in a range of 1-10, 1-40, 1-100, 1-200, or 1-500 nanometers. In some other embodiments, all pores of a membrane has a substantially similar pore size.

The pore size may control the rate of diffusion. The pore size may be modulated to control the rate of diffusion. A membrane may be made with a selected average pore size for the purpose of controlling the rate of diffusion. Different pharmaceutical compositions of agents can diffuse through the membrane at varying rates, controlled in part by the physical and chemical properties of the pharmaceutical compositions, agents, and membrane materials. In some embodiments, the selected pore size permits the transport of solutes with a molecule weight of less than 1 million Daltons. In a further embodiments, the selected pore size permits the transport of solutes with a molecule weight in the range of 5,000 Daltons to 1 million Daltons. In another further embodiment, the selected pore size permits the transport of solutes with a molecule weight of less than 1,000 Daltons. In addition, membranes with varying average pore sizes can be made and tested experimentally to fmd a pore size that provides a desirable diffusion rate for a specific pharmaceutical composition or agent.

A pharmaceutical composition or agent may be delivered to a microdialysis probe by using a pump, such as a peristaltic pump or syringe pump. The use of a pump can lead to controlled delivery. For example, the agent or pharmaceutical composition can be delivered through a microdialysis probe in a continuous fashion. Alternatively, the agent or pharmaceutical composition can be delivered in several doses. The time interval between any two doses can be controlled. Furthermore, the flow rate may be individually controlled for each microdialysis probe. The flow rate may be in a range of about 0.1 to about 5 microliter/min. The flow rate may be about 0.1, 0.2, 0.3, 0.4, 0.5, 0.6, 1.0, 1.5, 2.0, 2.5, 3.0, 3.5, 4.0, 4.5, or about 5 microliter/min.

A microdialysis probe may be inserted into a solid tissue directly or indirectly. The indirectly insertion may comprise the steps of: (1) insertion of a microdialysis probe into a needle; (2) insertion of the needle into a solid tissue; and (3) withdrawal of the needle from the solid tissue, therefore leaving the microdialysis probe in the solid tissue. In some cases, a plurality of microdialysis probes are inserted into a solid tissue with a plurality of needle along a plurality of axes into a solid tissue. Each of the plurality of needles holds one of the plurality of microdialysis probes. In some embodiments, the plurality of axes are a plurality of parallel axes. In some embodiments, the plurality of needles are part of a needle array device. The needle array device may comprise at least 2, 5, 10 or even more needles.

In addition, the present invention provides a microdialysis probe which has an inlet-tubing without an outlet-tubing. In some embodiments, the terminal end of the probe is surrounded by a semi-permeable membrane. In this design, the microdialysis probe may act as a diffuser in which liquid and small molecules are actively pumped across the semi-permeable membrane.

The insertion of a microdialysis probe may be guided. In some embodiments, the insertion of a microdialysis probe is guided by a fixed guide to direct the insertion of a microdialysis probe into a selected region of a solid tissue. In some embodiments, the insertion of a microdialysis probe is guided by an arthroscopic device.

The present invention also provide a method of monitoring drug metabolism and response in a solid tissue. For example, without being limiting, a microdialysis probe may be a part of closed loop. The membrane section of the microdialysis probe may span the solid tissue. By running a continuous flow of a solution of an agent through the microdialysis probe for a selected period of time, the agent may be delivered to the solid tissue. After another selected period of time, another solution (e.g. saline) may be flown through the microdialysis probe. Solutes in the solid tissue, for example without being limiting, may be collected in dialysate and analyzed. Non-limiting examples of solutes include biomarkers, agents delivered to the solid tissue and metabolites of the agents delivered to solid tissue. By analyzing the presence or absence and/or concentration of solutes, the efficacy of the agents on the solid tissue may be determined.

Target Tissues

In some embodiments, the present disclosure exemplifies a method for screening agents in a solid tissue. Solid tissues are well known to the medical arts and may include any cohesive, spatially discrete non-fluid defined anatomic compartment that is substantially the product of multicellular, intercellular, tissue and/or organ architecture, such as a three-dimensionally defined compartment that may comprise or derive its structural integrity from associated connective tissue and may be separated from other body areas by a thin membrane (e.g., meningeal membrane, pericardial membrane, pleural membrane, mucosal membrane, basement membrane, omentum, organ-encapsulating membrane, or the like). Non-limiting exemplary solid tissues may include brain, liver, lung, kidney, prostate, ovary, spleen, lymph node (including tonsil), thyroid, pancreas, heart, skeletal muscle, intestine, larynx, esophagus and stomach. Anatomical locations, morphological properties, histological characterization, and invasive and/or non-invasive access to these and other solid tissues are all well known to those familiar with the relevant arts. In some embodiments, the tissue is, or is suspected of being, cancerous, inflamed, infected, atrophied, numb, in seizure, or coagulated. In some embodiments, the tissue is, or is suspected of being, cancerous. In some embodiments, the tissue is cancerous.

In some embodiments, the present method is directed to cancer, and the target tissue comprises a tumor, which may be benign or malignant, and comprises at least one cancer cell selected from the group consisting of a prostate cancer cell, a breast cancer cell, a colon cancer cell, a lung cancer cell, a brain cancer cell, and an ovarian cancer cell. In certain embodiments, the tumor comprises a cancer selected from adenoma, adenocarcinoma, squamous cell carcinoma, basal cell carcinoma, small cell carcinoma, large cell undifferentiated carcinoma, chondrosarcoma and fibrosarcoma. Art-accepted clinical diagnostic criteria have been established for these and other cancer types, such as those promulgated by the U.S. National Cancer Institute (Bethesda, Md., USA) or as described in DeVita, Hellman, and Rosenberg's Cancer: Principles and Practice of Oncology (2008, Lippincott, Williams and Wilkins, Philadelphia/Ovid, New York); Pizzo and Poplack, Principles and Practice of 25 Pediatric Oncology (Fourth edition, 2001, Lippincott, Williams and Wilkins, Philadelphia/Ovid, New York); and Vogelstein and Kinzler, The Genetic Basis of Human Cancer (Second edition, 2002, McGraw Hill Professional, New York). Other non-limiting examples of typing and characterization of particular cancers are described, e.g., in Ignatiadis et al. (2008 PathobioL 75:104); Curr. Drug Discov. Technol. 5:9); and Auman et al. (2008 Drug Metab. Rev. 40:303). In certain embodiments the selected region of tissue is a portion of a tumor in a subject, and in certain further embodiments the subject is one of a preclinical model OR a human patient.

Certain embodiments contemplate a subject or biological source that is a human subject such as a patient that has been diagnosed as having or being at risk for developing or acquiring cancer according to art-accepted clinical diagnostic criteria, such as those of the U.S. National Cancer Institute (Bethesda, Md., USA) or as described in DeVita, Hellman, and Rosenberg's Cancer: Principles and Practice of Oncology (2008, Lippincott, Williams and Wilkins, Philadelphia/Ovid, New York); Pizzo and Poplack, Principles and Practice of Pediatric Oncology (Fourth edition, 2001, Lippincott, Williams and Wilkins, Philadelphia/Ovid, New York); and Vogelstein and Kinzler, The Genetic Basis of Human Cancer (Second edition, 2002, McGraw Hill Professional, New York); certain embodiments contemplate a human subject that is known to be free of a risk for having, developing or acquiring cancer by such criteria.

Certain other embodiments contemplate a non-human subject or biological source, for example a non-human primate such as a macaque, chimpanzee, gorilla, vervet, orangutan, baboon or other non-human primate, including such non-human subjects that may be known to the art as preclinical models, including preclinical models for solid tumors and/or other cancers. Certain other embodiments contemplate a non-human subject that is a mammal, for example, a mouse, rat, rabbit, pig, sheep, horse, bovine, goat, gerbil, hamster, guinea pig or other mammal; many such mammals may be subjects that are known to the art as preclinical models for certain diseases or disorders, including solid tumors and/or other cancers (e.g., Talmadge et al., 2007 Am. J. Pathol. 170:793; Kerbel, 2003 Canc. Biol. Therap. 2(4 Suppl 1):S134; Man et al., 2007 Canc. Met. Rev. 26:737; Cespedes et al., 2006 Clin. TransL Oncol. 8:318). The range of embodiments is not intended to be so limited, however, such that there are also contemplated other embodiments in which the subject or biological source may be a non-mammalian vertebrate, for example, another higher vertebrate, or an avian, amphibian or reptilian species, or another subject or biological source. A transgenic animal is a non-human animal in which one or more of the cells of the animal includes a nucleic acid that is non-endogenous (i.e., heterologous) and is present as an extrachromosomal element in a portion of its cell or stably integrated into its germ line DNA (i.e., in the genomic sequence of most or all of its cells). In certain embodiments of the present invention, the tissue of a transgenic animal may be targeted.

Methods of the current invention are suitable for administering agents to a variety of animal tissues; thus the methods have medical and veterinary uses. In some embodiments, the animal tissue is soft tissue. Non-limiting examples of soft tissue include muscle, adipose, skin, tendons, ligaments, blood, and nervous tissue. In some embodiments, the animal is a reptile, an amphibian, an ayes, or a mammal In some embodiments, the animal is a mammal. In some embodiments, the animal is a mouse. In some embodiments, the animal is a human. In some embodiments, the animal is a pet, a companion, a guardian, a working animal, a breeding animal, a service animal, a racing animal, a farm animal, a herded animal, or a laboratory animal.

In some embodiments, the target tissue does not exhibit features of a disease, but may be used to assess the response of an individual tissue to one or more compounds. In some cases, one or more agents may be administered to produce an altered physiologic state within a tissue. An altered physiologic state can be any detectable parameter that directly relates to a condition, process, pathway, dynamic structure, state or other activity in a solid tissue (and in some embodiments in a solid tumor) including in a region or a biological sample that permits detection of an altered (e.g., measurably changed in a statistically significant manner relative to an appropriate control) structure or function in a biological sample from a subject or biological source. The methods of the present invention thus pertain in part to such correlation where an indicator of altered physiologic state can be, for example, a cellular or biochemical activity, including as further non-limiting examples, cell viability, cell proliferation, apoptosis, cellular resistance to anti-growth signals, cell motility, cellular expression or elaboration of connective tissue-degrading enzymes, cellular recruitment of angiogenesis, or other criteria as provided herein.

Altered physiologic state can further refer to any condition or function where any structure or activity that is directly or indirectly related to a solid tissue function has been changed in a statistically significant manner relative to a control or standard, and can have its origin in direct or indirect interactions between a solid tissue constituent and an introduced agent, or in structural or functional changes that occur as the result of interactions between intermediates that can be formed as the result of such interactions, including metabolites, catabolites, substrates, precursors, cofactors and the like. Additionally, altered physiologic state can include altered signal transduction, respiratory, metabolic, genetic, biosynthetic or other biochemical or biophysical activity in some or all cells or tissues of a subject or biological source. As non-limiting examples, altered biological signal transduction, cell viability, cell proliferation, apoptosis, cellular resistance to anti-growth signals, cell motility, cellular expression or elaboration of connective tissue-degrading enzymes, cellular recruitment of angiogenesis, or other criteria including induction of apoptotic pathways and formation of atypical chemical and biochemical crosslinked species within a cell, whether by enzymatic or non-enzymatic mechanisms, can all be regarded as indicative of altered physiologic state.

Agents

In some embodiments, the agents comprise an agent that is selected from (a) a gene therapy agent; (b) a chemotherapy agent; (c) a small molecule; (d) an antibody; (e) a protein; (f) one of a small interfering RNA and an encoding polynucleotide; (g) one of an antisense RNA and an encoding polynucleotide; (h) one of a ribozyme and an encoding polynucleotide; (i) a detectable label; (j) one of a therapeutic protein, a peptide, polypeptide, and a peptidomimetic; (k) an anti-angiogenic agent; (l) an epigenetic modifier; (m) an antibody-drug conjugates; (n) a kinase inhibitor; and (o) an inhibitor of metabolic pathway targets that are preferentially expressed in cancer cells. In certain further embodiments, the detectable label is selected from a radiolabel, a radioopaque label, a fluorescent label, a colorimetric label, a dye, an enzymatic label, a GCMS tag, avidin, and biotin. In certain embodiments, the agents are selected from (i) a gene therapy agent that comprises at least one operably linked promoter, (ii) a small interfering RNA-encoding polynucleotide that comprises at least one operably linked promoter; (iii) an antisense RNA encoding polynucleotide that comprises at least one operably linked promoter; and (iv) a ribozyme-encoding polynucleotide that comprises at least one operably linked promoter. In certain further embodiments, the operably linked promoter is selected from a constitutive promoter and a regulatable promoter. In certain still further embodiments, the regulatable promoter is selected from an inducible promoter, a tightly regulated promoter and a tissue-specific promoter. Example of anti-angiogenic agent includes, but is not limited to, bevacizumab and others in development. Example of epigenetic modifier includes, but is not limited to, azacitididne and decitabine and others in development. The small molecule may be an agent with significant cytotoxicity.

Agents may be dissolved or suspended in an aqueous solution as a mixture or colloid that may be delivered to a target tissue. When used to refer to agent delivered through microdialysis probes or needles, the term agent is to be read broadly to read on any substance capable of flowing through such a microdialysis probe or needle, including liquids, gases, colloids, suspended solids, etc.

In some embodiments, the agents are candidate oncology agents. Selection of candidate oncology agents is understood and determinable by one skilled in the relevant arts (see, e.g., Berkowet al., eds., The Merck Manual, 16th edition, Merck and Co., Rahway; N.J., 1992; Goodman et al., eds., Goodman and Gilman's The Pharmacological Basis of Therapeutics, 10th edition, Pergamon Press, Inc., Elmsford, N.Y., (2001); De Vita, Hellman, and Rosenberg's Cancer: Principles and Practice of Oncology (2008, Lippincott, Williams and Wilkins, Philadelphia/Ovid, New York); Pizzo and Poplack, Principles and Practice of Pediatric Oncology (Fourth edition, 2001, Lippincott, Williams and Wilkins, Philadelphia/Ovid, New York); Avery's Drug Treatment: Principles and Practice of Clinical Pharmacology and Therapeutics, 3rd edition, ADIS Press, LTD., Williams and Wilkins, Baltimore, Md. (1987), Ebadi, Pharmacology, Little, Brown and Co., Boston, (1985); Osolci al., eds., Remington's Pharmaceutical Sciences, 18th edition, Mack Publishing Co., Easton, Pa. (1990); Katzung, Basic and Clinical Pharmacology, Appleton and Lange, Norwalk, Conn. (1992)). Therapeutic agents can be selected from resources that disclose listings of investigational therapeutics, for instance, the National Institutes of Health (Bethesda, Md.) which maintains a database of ongoing and planned clinical trials at its "ClinicalTrials.gov" website.

Agents for use in screening methods and in methods of rating for development into therapeutic agents can be provided as "libraries" or collections of compounds, compositions or molecules. Such molecules typically include compounds known in the art as "small molecules" and having molecular weights less than 105 daltons, less than 104 daltons, or less than 103 daltons.

For example, a plurality of members of a library of test compounds can be introduced as therapeutic agents to a region of a solid tumor of known tumor type in each one or a plurality of subjects having a tumor of the known tumor type, by distributing each of the therapeutic agents to a plurality of positions along an axis within the region in each subject, and after a selected period of time (e.g., a range of time, a minimum time period or a specific time period) the region of solid tumor in which the candidate agents have been introduced can be imaged or removed from each subject, and each region compared by detecting an effect (if any) of each agent on the respective position within the region, for instance, by determining whether an altered physiologic state is present as provided herein, relative to positions in the region that are treated with control agents as provided herein, which would either produce no effect (negative control) or a readily detectable effect (positive control).

Agents further can be provided as members of a combinatorial library, which can include synthetic agents prepared according to a plurality of predetermined chemical reactions performed in a plurality of reaction vessels. For example, various starting compounds can be prepared employing one or more of solid-phase synthesis, recorded random mix methodologies and recorded reaction split techniques that permit a given constituent to traceably undergo a plurality of permutations and/or combinations of reaction conditions. The resulting products comprise a library that can be screened followed by iterative selection and synthesis procedures, such as a synthetic combinatorial library of peptides (see e.g., PCT/US91/08694, PCT/US91/04666, which are hereby incorporated by reference in their entireties) or other compositions that can include small molecules as provided herein (see e.g., PCT/US94/08542, EP 0774464, U.S. Pat. Nos. 5,798,035, 5,789,172, 5,751,629, which are hereby incorporated by reference in their entireties). Those having ordinary skill in the art will appreciate that a diverse assortment of such libraries can be prepared according to established procedures, and tested for their influence on an indicator of altered mitochondrial function, according to the present disclosure. Other agents can be proteins (including therapeutic proteins), peptides, peptidomimetics, polypeptides, and gene therapy agents (e.g., plasmids, viral vectors, artificial chromosomes and the like containing therapeutic genes or polynucleotides encoding therapeutic products, including coding sequences for small interfering RNA (siRNA), ribozymes and antisense RNA) which in certain further embodiments can comprise an operably linked promoter such as a constitutive promoter or a regulatable promoter, such as an inducible promoter (e.g., IPTG inducible), a tightly regulated promoter (e.g., a promoter that permits little or no detectable transcription in the absence of its cognate inducer or depressor) or a tissue-specific promoter. Methodologies for preparing, testing and using these and related agents are known in the art. See, e.g., Ausubel (Ed.), Current Protocols in Molecular Biology (2007 John Wiley & Sons, NY); Rosenzweig and Nabel (Eds), Current Protocols in Human Genetics (esp. Ch. 13 therein, "Delivery Systems for Gene Therapy", 2008 John Wiley & Sons, NY); Abell, Advances in Amino Acid Mimetics and Peptidomimetics, 1997 Elsevier, NY.

In some embodiments, the agent is a small molecule agent. As used herein, the term "small molecule agent" means an agent with a molecule weight less than about 1000 daltons, less than about 800 daltons, or less than about 500 daltons. In some further embodiments, the small molecule agent is an anti-cancer agent. The anti-cancer agent may be an approved anti-cancer drug currently on the market, an anti-cancer drug currently in clinical trials, an anti-cancer drug withdrawn from clinical trials or market due to toxicity or lack of efficacy, or an early stage anti-cancer drug in the development.

Other agents can be antibodies, including naturally occurring, immunologically elicited, chimeric, humanized, recombinant, and other engineered antigen-specific immunoglobulins and artificially generated antigen-binding fragments and derivatives thereof, such as single-chain antibodies, minibodies, Fab fragments, bi-specific antibodies and the like. See, e.g., Coligan et al. (Eds.), Current Protocols in Immunology (2007 John Wiley & Sons, NY); Harlow and Lane, Antibodies: A Laboratory Manual (1988 Cold Spring Harbor Press, Cold Spring Harbor, N.Y.); Harlow and Lane, Using Antibodies (1999 Cold Spring Harbor Press, Cold Spring Harbor, N.Y.).

Pharmaceutically acceptable carriers for therapeutic use are well known in the pharmaceutical art, and are described, for example, in Remingtons Pharmaceutical Sciences. Mack Publishing Co. (A. R. Gennaro edit. 1985). For example, sterile saline and phosphate-buffered saline at physiological pH can be used. Preservatives, stabilizers, dyes and other ancillary agents can be provided in the pharmaceutical composition. For example, sodium benzoate, sorbic acid and esters of p-hydroxybenzoic acid can be added as preservatives. In addition, antioxidants and suspending agents can be used. "Pharmaceutically acceptable salt" refers to salts of drug compounds derived from the combination of such compounds and an organic or inorganic acid (acid addition salts) or an organic or inorganic base (base addition salts). The agents, including drugs, contemplated for use herein can be used in either the free base or salt forms, with both forms being considered as being within the scope of the certain present invention embodiments.

The pharmaceutical compositions that contain one or more agents can be in any form which allows for the composition to be administered to a subject. According to some embodiments, the composition will be in liquid form and the route of administration will comprise administration to a solid tissue as described herein. The term parenteral as used herein includes transcutaneous or subcutaneous injections, and intramuscular, intramedullar and intrasternal techniques.

The pharmaceutical composition is formulated so as to allow the active ingredients contained therein to be bioavailable upon administration of the composition to a subject such as a human subject. Compositions that will be administered to a subject can take the form of one or more doses or dosage units, where for example, a pre-measured fluid volume can comprise a single dosage unit, and a container of one or more compositions (e.g., drugs) in liquid form can hold a plurality of dosage units. A dose of an agent includes all or a portion of a therapeutically effective amount of a particular agent that is to be administered in a manner and over a time sufficient to attain or maintain a desired concentration range of the agent, for instance, a desired concentration range of the agent in the immediate vicinity of a delivery microdialysis probe or needle in a solid tissue, and where the absolute amount of the agent that comprises a dose will vary according to the agent, the subject, the solid tissue and other criteria with which the skilled practitioner will be familiar in view of the state of the medical and pharmaceutical and related arts. In certain embodiments, at least two doses of the agent can be administered, and in certain other embodiments 3, 4, 5, 6, 7, 8, 9, 10 or more doses can be administered.

A liquid pharmaceutical composition as used herein, whether in the form of a solution, suspension or other like form, can include one or more of the following adjuvants: sterile diluents such as water for injection, saline solution, physiological saline, Ringer's solution, saline solution (e.g., normal saline, or isotonic, hypotonic or hypertonic sodium chloride), fixed oils such as synthetic mono or digylcerides which can serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. In some embodiments, physiological saline is the adjuvant. An injectable pharmaceutical composition can be sterile. It can also be desirable to include other components in the preparation, such as delivery vehicles including but not limited to aluminum salts, water-in-oil emulsions, biodegradable oil vehicles, oil-in-water emulsions, biodegradable microcapsules, hydrogels, and liposomes.

While any suitable carrier known to those of ordinary skill in the art can be employed in the pharmaceutical compositions of this invention, the type of carrier will vary depending on the mode of administration and whether a conventional sustained drug release is also desired. For parenteral administration, such as supplemental injection of drug, the carrier can comprise water, saline, alcohol, a fat, a wax or a buffer. Biodegradable microspheres (e.g., polylactic galactide) can also be employed as carders for the pharmaceutical compositions of this invention. Suitable biodegradable microspheres are disclosed, for example, in U.S. Pat. Nos. 4,897,268 and 5,075,109. In some embodiments, the microsphere be larger than approximately 25 microns, while other embodiments are not so limited and contemplate other dimensions.

Pharmaceutical compositions can also contain diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. In some embodiments, an agent (e.g., a therapeutic drug or a candidate drug) is formulated as a lyophilizate using appropriate excipient solutions (e.g., sucrose) as diluents.

Position Markers

Certain embodiments contemplate direct delivery of multiple agents, candidate drugs, imaging agents, positional markers, indicators of efficacy and appropriate control compositions to a plurality of spatially defined locations along parallel axes in a solid tissue, such as a solid tumor, followed, after a desired time interval, by excision of the treated tissue and evaluation or analysis of the tissue for effects of the treatments. Indicators of efficacy can be, for example, detectable indicator compounds, nanoparticles, nanostructures or other compositions that comprise a reporter molecule which provides a detectable signal indicating the physiological status of a cell, such as a vital dye (e.g., Trypan blue), a colorimetric pH indicator, a fluorescent compound that can exhibit distinct fluorescence as a function of any of a number of cellular physiological parameters (e.g., pH, intracellular $Ca^{2+}$ or other physiologically relevant ion concentration, mitochondrial membrane potential, plasma membrane potential, etc., see Haugland, The Handbook: A Guide to Fluorescent Probes and Labeling Technologies (10th Ed.) 2005, Invitrogen Corp., Carlsbad, Calif.), an enzyme substrate, a specific oligonucleotide probe, a reporter gene, or the like. Control compositions can be, for example, negative controls that have been previously demonstrated to cause no statistically significant alteration of physiological state, such as sham injection, saline, DMSO or other vehicle or buffer control, inactive enantiomers, scrambled peptides or nucleotides, etc.; and positive controls that have been previously demonstrated to cause a statistically significant alteration of physiological state, such as an FDA-approved therapeutic compound.

In some embodiments, a pharmaceutical formulation further comprises a dye. The dye can be imaged after administration of the pharmaceutical composition to an animal tissue to observe the distribution and activity of a therapeutic agent present in the same pharmaceutical composition. In some embodiments, the dye is a fluorescent dye. In some embodiments, the dye is a radioactive dye.

In some embodiments, the excised tissue can be cut into a plurality of serial histological sections along parallel planes that are substantially normal (e.g., perpendicular or deviating from perpendicular by as much as 1, 2, 3, 4, 5, 6, 7, 8, 9, 10, 11, 12, 13, 14, 15, 20, 25, 30, 35 or more degrees) to the parallel axes, for analysis by any of a number of known histological, histochemical, immunohistological, histopathologic, microscopic (including morphometric analysis and/or three-dimensional reconstruction), cytological, biochemical, pharmacological, molecular biological, immunochemical, imaging or other analytical techniques, which techniques are known to persons skilled in the relevant art. See, e.g., Bancroft and Gamble, Theory and Practice of Histological Techniques (6th Ed.) 2007 Churchill Livingstone, Oxford, UK; Kiernan, Histological and Histochemical Methods: Theory and Practice, 2001 Cold Spring Harbor Laboratory Press, Cold Spring Harbor, N.Y.; and M. A. Hayat (Ed.), Cancer Imaging—Vols. 1 and 2, 2007 Academic Press, NY, each of which is incorporated by reference herein in its entirety. Imaging can be performed before, during or after dispenser needles are inserted into the solid tissue. Positional markers are known and include, as non-limiting examples, metal or plastic clips, fluorescent quantum dots, India ink, metal or plastic beads, dyes, stains, tumor paint (Veiseh et al., 2007 Canc. Res. 67:6882) or other positional markers, and can be introduced at desired positions. Markers can include any subsequently locatable source of a detectable signal, which can be a visible, optical, colorimetric, dye, enzymatic, GCMS tag, avidin, biotin, radiological (including radioactive radiolabel and radio-opaque), fluorescent or other detectable signal.

In some embodiments, microdialysis probes are used as position markers. After delivering an agent to a solid tissue, the solid tissue may be sectioned along parallel planes that are substantially normal to the insertion axes of maicrodialysis probes. The residual microdialysis probe may serve as position markers.

A detectable marker thus comprises a unique and readily identifiable gas chromatography/mass spectrometry (GCMS) tag molecule. Numerous such GCMS tag molecules are known to the art and can be selected for use alone or in combination as detectable identifier moieties. By way of illustration and not limitation, various different combinations of one, two or more such GCMS tags can be added to individual reservoirs of the device described herein in a manner that permits the contents of each reservoir to be identified on the basis of a unique GCMS "signature", thereby permitting any sample that is subsequently recovered from an injection region to be traced back to its needle of origin for identification purposes. Examples of GCMS tags include $\alpha$, $\alpha$, $\alpha$-trifluorotoluene, $\alpha$-methylstyrene, o-anisidine, any of a number of distinct cocaine analogues or other GCMS tag compounds having readily identifiable GCMS signatures under defined conditions, for instance, as are available from SPEX CertiPrep Inc. (Metuchen, N.J.) or from SigmaAldrich (St. Louis, Mo.), including Supelco® products described in the Supelco® 2005 gas chromatography catalog and available from SigmaAldrich.

Certain other embodiments contemplate the use of colored microdialysis probe or needle as position markers. For example, when microdialysis probes are used for delivering agents, colored wax attached to the probes can be pulled through a solid tissue to mark injection zones for the following histology sectioning analysis.

Devices

In one aspect, the present disclosure provides a device for delivering a plurality of agents to a solid tissue of a subject, comprising a plurality of microdialysis probes. The device may further comprise any one of the followings: (1) a plurality of needles, each configured to receive one of said plurality of microdialysis probes; (2) at least one controller, operatively coupled to said plurality of needles; and (3) a guiding device to guide the insertion of said plurality of needles to said solid tissue. The device may comprise at least 3, 4, 5, 6, or 10 microdialysis probes or needles. In some embodiments, controller is a computer. The computer may be used to control the insertion of microdialysis probe and injection of agents. In some further embodiments, the computer is part of a cloud computing system.

In another aspect, the present disclosure provides methods of delivery of one or more agents with a needle array device. In some cases, the needle array device is used for inserting of a plurality of microdialysis probes into a solid tissue. In some other cases, the needle array device is used for delivering a plurality of agent by (1) inserting a plurality of needles into a solid tissue; and (2) withdrawing the one or more needles from and injecting the one or more agents into the solid tissue, such that the one or more agents are delivered to the solid tissue The needle array device may comprise a plurality of needles and a plurality of reservoirs. The needle array device may comprise at least 1, 2, 3, 4, 5, 6, 7, 8, 9, 10, 11, 12, 13, 14, 15, 16, 17, 18, 20, 25, 30 or even more needles. The needle array device may comprise at least 1, 2, 3, 4, 5, 6, 7, 8, 9, 10, 11, 12, 13, 14, 15, 16, 17, 18, 20, 25, 30 or even more reservoirs. In some embodiments, each one of the plurality of reservoirs is in a separate fluid communication with a respective one of a plurality of needles. The needle array device may further comprise one or more actuators. The one or more actuators may be driven to produce negative or positive pressure. The needle array device may further comprise one or more controllers. The controllers may control the depth of needle insertion, and thus the depth of microdialysis probe insertion. One example of needle array devices is described in WO 2009/023798 to Bahrami et al. and is herein incorporated by reference in its entirety.

Referring to FIG. 1, a needle array assembly 100 is shown, including a plurality of needles 112, a plurality of reservoirs 114, a plurality of delivery actuators such as, in the present example, plungers 116, and a controller 102. Each of the plurality of needles 112 is fixed in position relative to the others of the plurality of needles, and the plungers are likewise operatively coupled so as to be fixed in position and simultaneously actuable. Each of the plurality of needles 112 is in fluid communication with a respective one of the plurality of reservoirs 114, and each of the plurality of plungers includes a first end positioned in a respective one of the plurality of reservoirs 114. The controller 102 is operatively coupled to second ends of each of the plurality of plungers 116. The controller is configured to control actuation of the plungers within the reservoir with respect to speed, distance, and direction of movement.

Despite recently progress on the injection of agents with a needle array device, there remains a need to reduce potential platform variability. Platform variability could lead to missing injection, unequal agent deposition, cross-contamination or a combination thereof. Potential sources of platform variability may include: (a) tumor environment; (b) injection system; (c) operator technique. Among those, sources from injection system and operator technique may be fixable and controllable. Improvement on these two aspects could lead to improved methods, for example, improved precision and narrow biodistribution, for delivering an agent.

In one aspect, the present invention provides a device for controlling needle insertion into and withdrawal from a solid tissue, comprising: (a) a positioning mechanism; (b) a depth-control mechanism; and (c) a needle withdrawal mechanism.

A position mechanism is a mechanism to guide the insertion of a needle. The insertion of a needle may be guided by a hole. The hole may guide a needle to a site of insertion. The physical boundary set by the hole may improve the accuracy of needle insertion. In some embodiment, each hole accommodates just one needle.

A depth-control mechanism is a mechanism to control the depth of a needle insertion. The depth-control mechanism may be adjustable to control the depth of a needle insertion. In some embodiments, an attachment is attached to one end of the needle. The position of the attachment along the needle may be adjustable. The attachment may stop the further insertion of the needle upon in contact with a hole.

The needle withdrawal mechanism may comprise a drive mechanism. The drive mechanism may be controllable. It may move at certain controllable speed. The drive mechanism may be operatively connected to the position mechanism and control the speed of needle withdrawal.

In another aspect, there is provided a device for delivery of at least one agent to a solid tissue, comprising one bottom block and one top block in a substantially parallel arrangement, each having a plurality of holes. The plurality of holes in the bottom and top block may guide the insertion of needles. In some cases, the size of holes may be controlled to allow needles of a certain size to pass through. The device may lead to improved accuracy of needle insertion and exquisite control of delivery of the at least one agent to a solid tissue.

The examples and devices described herein are meant to be illustrative and not to limit scope of the present invention.

Figure 2:
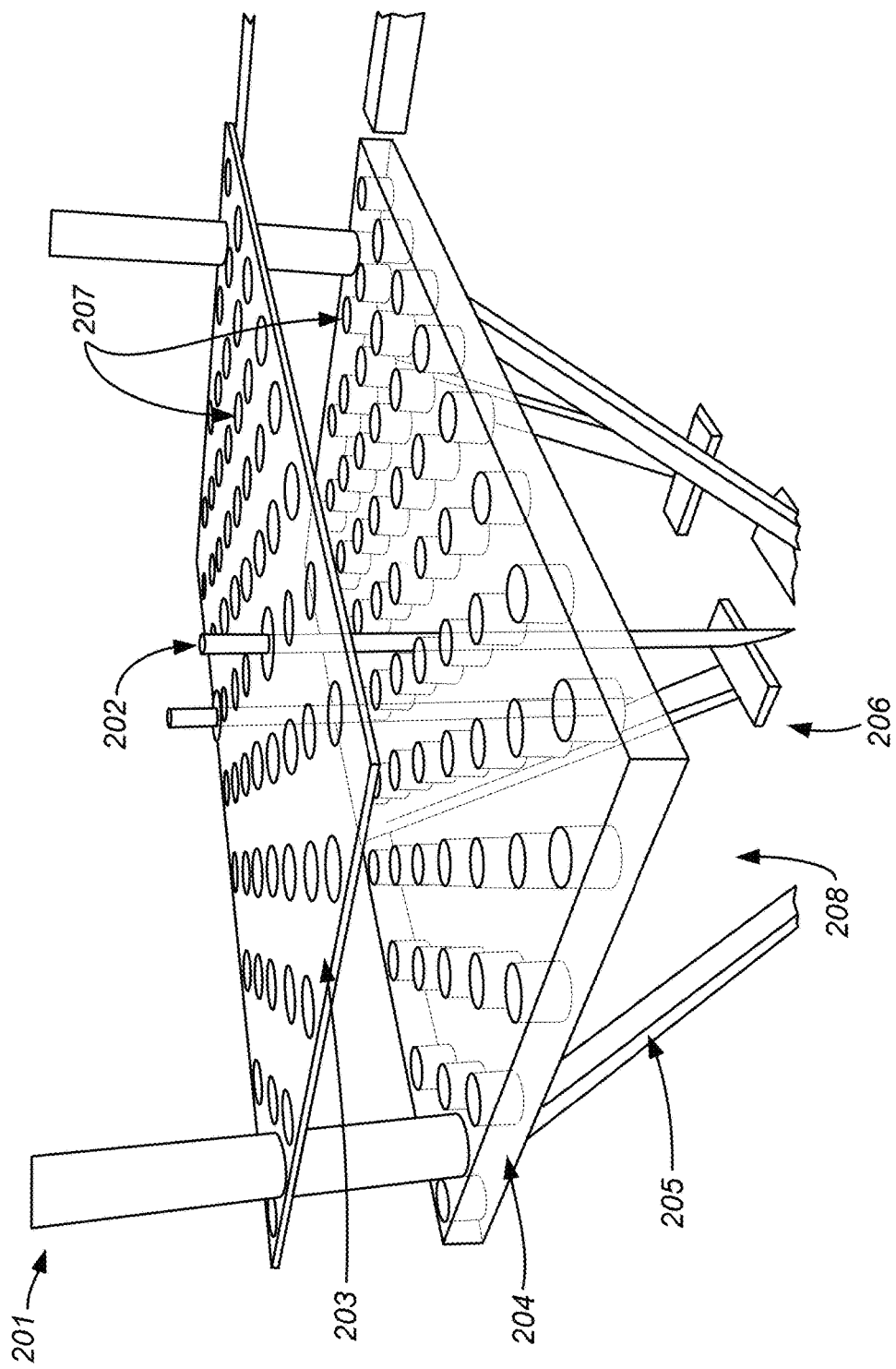
FIG. 2 shows an exemplary device embodying principles of the present invention.

FIG. 2 depicts one type of device embodying principles of the present invention. The device assembly comprises guiding rod 201, needle with control attachment 202, top block 203, bottom block 204, platform 206, leg 205 and holes 207 in the top and the bottom blocks. The top block 203 and the bottom block 204 are in a substantially parallel arrangement. The top block 203 and the bottom block 204 can be made of a variety of materials, including but are not limited to, metals and plastics. They may be transparent and may have a range of thickness. Each block may have multiple holes depicted as 207. The holes in each block may have a variety of arrangement. In a particular embodiment, the holes within each block form substantially parallel rows. The number of holes can be controlled to allow a specific number of needles to be inserted. The number of hole(s) in each block could be 1, 2, 3, 4, 5, 6, 7, 8, 9, 10, 11, 12, 13, 14, 15, 16, 17, 8, 19, 20, 21, 22, 23, 24, 25, 26, 27, 28, 29, 30, 35, 40, 50, 60, 70, 80, 90, 100, 150, 200, 300, 400, and 500. The number of holes may be 1000 or even 2000 if needed.

The present invention is intended to be useful with any and all standard sized needles. The size of holes 207 can be independently controlled to allow needles of specific gauge to pass through them. Generally, holes in the top block and the bottom block are aligned in such a way that the insertion trajectory of needles is substantially perpendicular to their planes. In some cases, two holes, one in the top block and one in the bottom block, defining the insertion trajectory are the same size. In addition, the size of holes within a block could be uniform or different. When the size of the holes is uniform, needles of the same size are used. When the size of the holes is different, needles of different sizes are used.

As depicted in FIG. 2, guiding rods 201 are used to guide the movement of the top block. The number of guiding rods may be any number between 1 and 10, inclusive. In FIG. 2, two guiding rods 201 are permanently attached to the bottom block 204. The guiding rods 201 control the movement trajectory of the top block 203. In some cases, the guiding rods 201 are substantially perpendicular to the bottom block 204 and/or the top block 203. In some cases, guiding rods are substantially parallel to each other. In some cases, the top block 203 moves to and from the bottom block 204 vertically. Besides the permanent attachment option as shown in FIG. 2, a variety of other ways of attaching the rods can be envisioned and is well within the scope of the present invention. For example, without being limiting, the rods can be attached to the bottom block via clamps, which are permanently attached to the side of the bottom block. In this particular configuration, the guiding rod 201 and the top block 203 can be readily disassembled from the device of needed.

Figure 3:
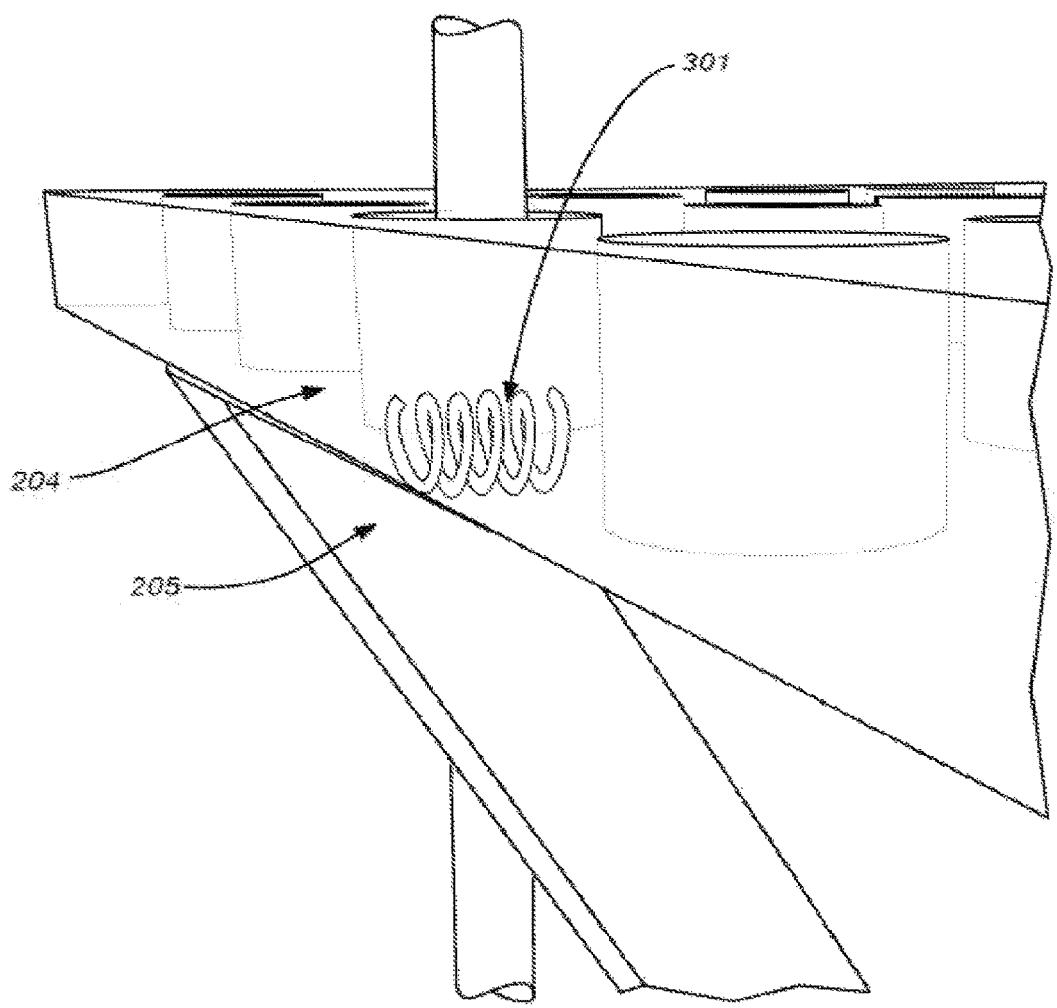
FIG. 3 shows an example of a platform for tumor stabilization using springs embodying principles of the present invention.

Additionally depicted in FIG. 3 is a platfoiin206 underneath the bottom block 204. The platform 206 provides support for the stationary bottom block 204. The platform can have a variety of shape and configurations so long as it provides support for the bottom block. One exemplary example of platform is shown in FIG. 3. The platform is comprised of 4 legs 205, each attached to one side of the bottom block 204. The other end of the leg 205 is attached to a supporting surface 208. The legs can be cylindrical, rectangular or square. The legs can be of any shape so long as they provide support for the bottom block 204. In a particular embodiment, the legs are vertically and horizontally adjustable. After placing a solid tissue or a subject in the device, the adjustable platform allows substantially improved tissue and/or subject stabilization during inserting of needles and injection of at least one agent. This leads to greater insertion precision, narrower biodistribution and less sample cross contamination, among others, compared to injections without the device. The number of legs can be changed. The number of legs may be any number between 1-12, inclusive.

Turing to FIG. 3, it depicts one configuration for achieving solid tissue and/or subject stabilization according to an embodiment. Spring 301 is in substantial contact with leg 205 and one side of the bottom block 204. If the legs are appropriately adjusted, upon placing a solid tissue or a subject in the device, the tension from the spring could firmly hold a solid tissue and/or subject during the needle insertion and agent injection process.

Figure 4:
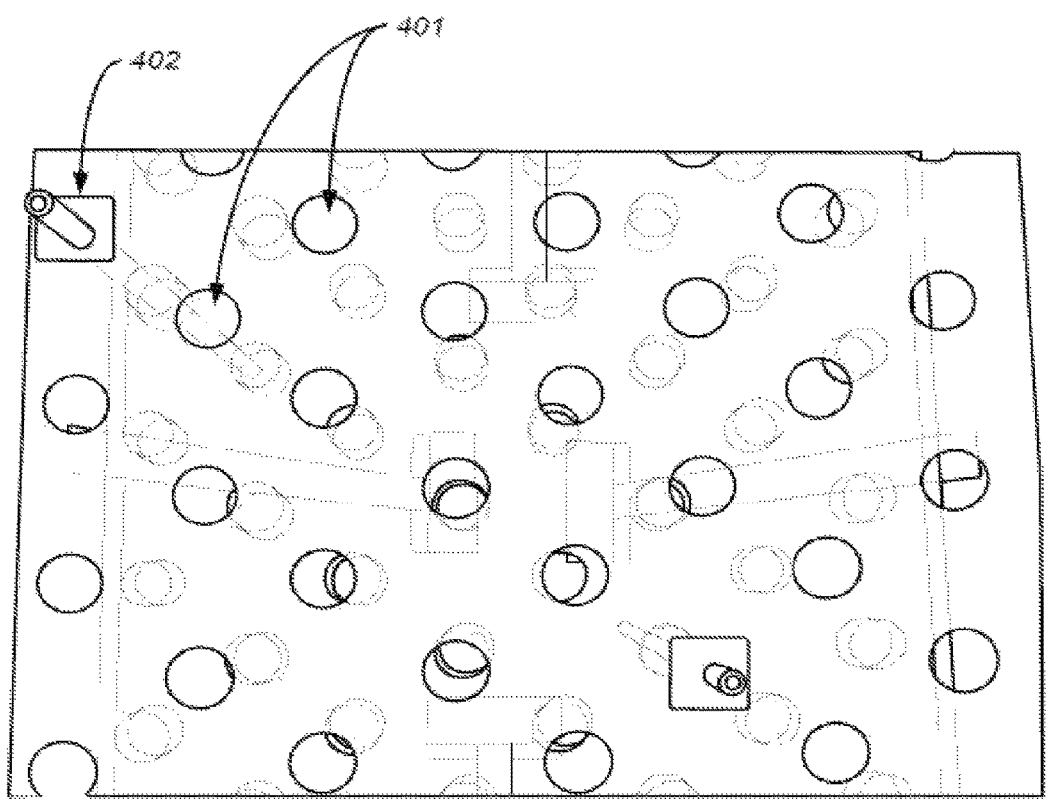
FIG. 4 shows a top view of needles with a control attachment embodying principles of the present invention.

FIG. 4 shows a top view of needles with the control attachment 402. In this figure, the control attachment 402 is substantially square and is attached around the needles. Upon contacting the upper surface of holes in the top block 103, the control attachment 102 stops further insertion of the needles. The position of attachment of control attachment 102 to the needle is one of the key factors for controlling the depth of insertion. Since the function of a control attachment is to stop the insertion of a needle, a control attachment can be of any size, shape, attachment configuration, and material so long as it can stop further insertion of needles.

Figure 5:
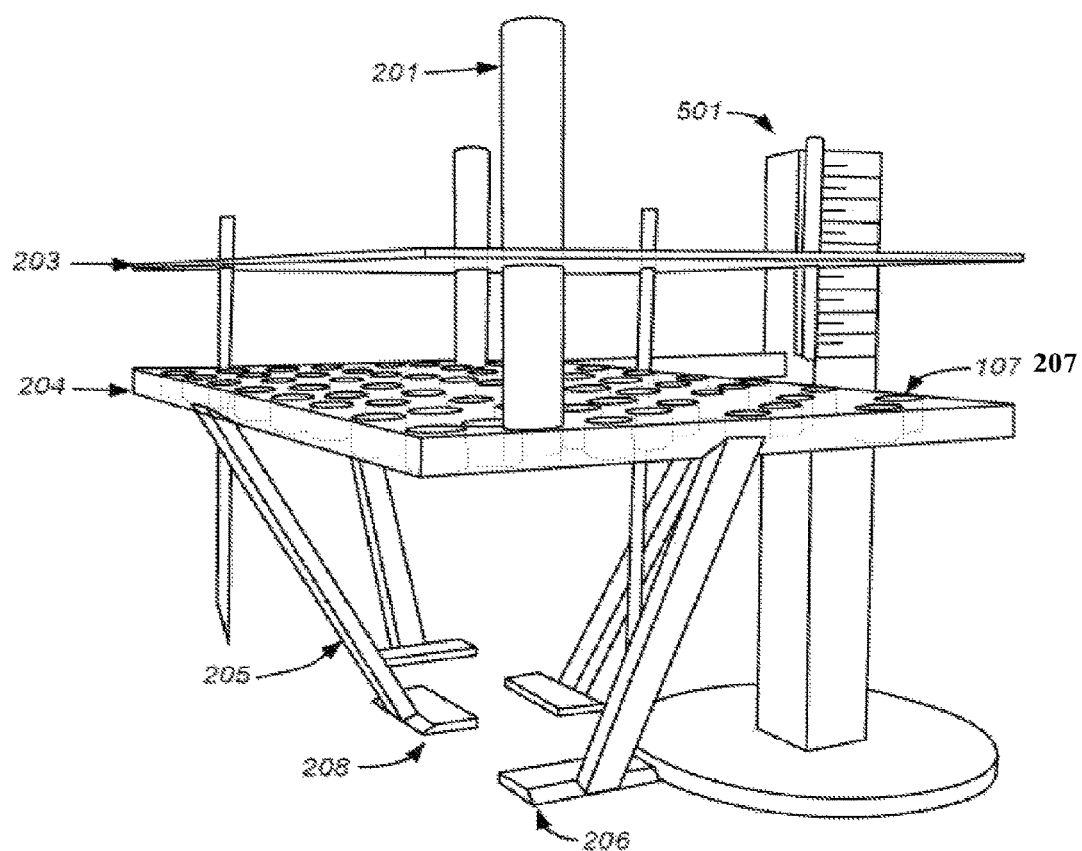
FIG. 5 shows an exemplary device with a drive mechanism for controlling vertical movement of a top block embodying principles of the present invention.

FIG. 5 depicts one particular type of device embodying principles of the present invention. In addition to the components outlined in FIG. 2, a drive mechanism 501 for controlling vertical movement of the top block 203 is shown. The drive mechanism 501 may serve two functions: (1) setting the position of the top block 203 prior to needle insertion; (2) withdrawing the top block 203 and needle with an control attachment away from a solid tissue or subject. The rate of withdrawal may be controlled.

According to one embodiment, there is provided a method of operating a device described herein. The drive mechanism 501 sets the position of the top block 203. A variety of factor, for example, without being limiting, the length of needle, the height of the bottom block 204, the size of a solid tissue and the depth of intended insertion, may be considered to determine a suitable position for the top block 203. The distance between the top block 203 and the bottom block 204 is not particularly limited. The distance may be 0, or at least 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 7.0, 8.0, 9.0, 10.0, 15, or 20 mm. The distance may be less than 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 7.0, 8.0, 9.0, 10.0, 15, or 20 mm. Alternatively, the distance may be about 0, 0.01, 0.02, 0.03. 0.04, 0.05, 0.06, 0.07, 0.08, 0.09, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 7.0, 8.0, 9.0, 10.0, 15, or 20 mm. When the distance between two blocks is zero, the top block lays on the top of the bottom block. After setting the position of the top block, the drive mechanism 501 keeps the top block stationary. A solid tissue or a subject is placed underneath the bottom block. In a particular embodiment, the solid tissue or subject is placed substantially within the boundary set by all legs. For example, one side of the solid tissue or subject is placed against the bottom portion of leg 205 and/or the supporting floor 208. The other side is placed against the bottom block 204 through adjusting legs 205. The placement of a solid tissue or a subject may occur before or after setting a suitable position for the top block 203. The platform 206 is adjusted to provide suitable stabilization for the solid tissue or subject. Needles are inserted through holes in the top block 203 and the bottom block 204. The path of needle insertion is guided by the holes. In some cases, the needles are a part of a needle array device.

The present invention does not limit the type or the shape of needle array so long as the shape of needle array matches the configuration of holes defined by the top block and the bottom block. Furthermore, the present invention does not limit the type of needle to be used as long as a control attachment is attached to the needle. Any of the needles may be independently selected from gauge 14, 16, 18, 20, 21, 22, 23, 24, 25, 26, 27, 28, 29 or 30. The needles may be end-port needles or porous needles. In some cases, the needles are end-port needles. In some cases, the needles are porous needles. In some cases, the needles are a mixture of end-port needles and porous needles. In some cases, all the needles are gauge 26. When a needle array device is used, one end of the needle is attached to the device. The device and its use has been described in US patent applications 2010/0330589A1 by Bahrami et al., published on Dec. 30, 2010; and 2011/0230839A1 by Bahraini et al., published on Sep. 22, 2011.

After insertion of needles, the top block 203 is lifted away from the bottom block 204 at a selected speed controlled by the drive mechanism 501. Simultaneously, at least one agent, typically dissolved and/or admixed with at least one suitable solvent, is injected through needles into respective locations within a solid tissue. The rate of lifting the top block 203 and the rate of injection can be independently controlled. The choice of each rate is likely determined by a variety of factors, such as for example, but is not limited to, the type of solid tissue, the size of needle, the viscosity of the solvent and the permeability of the at least one agent. In some embodiments, the rate of movement of the top block is at least 0.1, 0.15, 0.2, 0.25, 0.3, 0.35, 0.4, 0.45, 0.5, 0.55, 0.6, 0.65, 0.7, 0.75, 0.8, 0.85, 0.9, 1.0, 1.1, 1.2, 1.4, 1.6, 1.8, 2.0, 2.2, 2.4, 2.6, 2.8, 3.0, 4.0, 5.0, 6.0, 7.0, 8.0, 9.0, 10, 11, 12, 13, 14, 15, 18, or 20 mm/min. In some embodiments, the rate of movement of the top block is less than 0.1, 0.15, 0.2, 0.25, 0.3, 0.35, 0.4, 0.45, 0.5, 0.55, 0.6, 0.65, 0.7, 0.75, 0.8, 0.85, 0.9, 1.0, 1.1, 1.2, 1.4, 1.6, 1.8, 2.0, 2.2, 2.4, 2.6, 2.8, 3.0, 4.0, 5.0, 6.0, 7.0, 8.0, 9.0, 10, 11, 12, 13, 14, 15, 18, or 20 mm/min. In some embodiments, the rate of movement of the top block is about 0.1, 0.15, 0.2, 0.25, 0.3, 0.35, 0.4, 0.45, 0.5, 0.55, 0.6, 0.65, 0.7, 0.75, 0.8, 0.85, 0.9, 1.0, 1.1, 1.2, 1.4, 1.6, 1.8, 2.0, 2.2, 2.4, 2.6, 2.8, 3.0, 4.0, 5.0, 6.0, 7.0, 8.0, 9.0, 10, 11, 12, 13, 14, 15, 18, or 20 mm/min. In some cases, the rate of injecting the at least one agent is at least 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.5, 1.8, 2.0, 2.5, 3.0, 3.5, 4.0, 4.5, 5, 6, 7, 8, 9, 10, 15, 20, 25, 30, 40, 50 µl/min or even more. In some other cases, the rate of injecting the at least one agent is less than 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.5, 1.8, 2.0, 2.5, 3.0, 3.5, 4.0, 4.5, 5, 6, 7, 8, 9, 10, 15, 20, 25, 30, 40 or 50 µl/min. In some other cases, the rate of injecting the at least one agent is about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.5, 1.8, 2.0, 2.5, 3.0, 3.5, 4.0, 4.5, 5, 6, 7, 8, 9, 10, 15, 20, 25, 30, 40 or 50 µl/min.

According to various embodiments, a region of tissue is left in place for some period of time before being resected. For example, 48-72 hours following delivery is thought to be generally sufficient for a tumor to exhibit a detectable response. In other cases, the wait period may be minutes, hours, days, or weeks. In addition, the tissue region may be imaged using known methods to precisely locate the target region of tissue prior to insertion of the needles. The region may be imaged repeatedly before and after delivery of the plurality of agents to the region of tissue. The number of repeats may be about 2, 3, 4, 5, 6, 7, 8, 9, 10, 11, 12, 13, 14, 15, 16, 17, 18, 19, 20 or even more.

According to some embodiments, solid tissue into which at least one agent has been delivered is subsequently resected from the subject and evaluated. For example, in a case where the target tissue is a cancerous tumor, the plurality of agents injected therein can include some agents whose efficacy or effect on such tumors is under investigation. By injecting the various agents in vivo then waiting a selected period before removing the tumor, the effect of the agents on the tumor in situ can be investigated. This preserves the tumor microenvironment and distinguishes this method from current ex vivo or in vitro therapeutics evaluation methods. Assuming that the needles used are configured to deliver a substantially equal amount of agents at any given location along their length, the agent delivered by each of the needles is evenly distributed to the surrounding tissue along the delivery axis on which the respective needle was positioned during the delivery of the agent to a solid tissue. Over time, each agent permeates outward from its delivery axis to a greater or lesser degree, depending on factors such as, for example, the density of the surrounding tissue, the viscosity and composition of the agent, the wettability of the tissue by the respective agent, etc. Typically, the portions of the tissue into which the agents spread are approximately column-shaped regions coaxial with the respective delivery axes.

Methods

Through the use of the methods described herein, which includes configuration (e.g., by placing at least one positional marker in one or more known locations of the multiple microdialysis probes or needles in a manner that permits ready identification of the effects at a particular location, if any, of the contents released from a particular needle at the tissue location these and related embodiments thus contemplate methods of simultaneously delivering and comparing the relative therapeutic efficacies and/or toxicities of a large number of candidate therapeutic agents. Such applications can find uses in drug screening and drug discovery, such as in preclinical animal models to identify and functionally characterize potential new therapeutics. For instance, a plurality of siRNAs can be administered intratumorally and their relative abilities to knock down expression of a desired target gene can be compared. Other similar embodiments can find uses in clinical contexts, for example, to "deselect", or eliminate from consideration, known therapeutic agents that have no effect in a particular tumor, thereby advantageously advancing the therapeutic management of a subject by avoiding the loss of time and the undesirable side-effects that can be associated with administering an ineffectual treatment regimen.

In certain other embodiments the evaluating comprises differentiating a degree of the effect of at least one of the plurality of agents on different sections of the solid tissue according to different characteristics of the different sections of the solid tissue. In certain other embodiments the evaluating comprises comparing a first effect of at least a first one of the plurality of agents on the solid tissue with a second effect of at least a second one of the plurality of agents on the solid tissue. In certain other embodiments the evaluating comprises, with respect to at least one of the plurality of agents, assessing at least one of efficacy, activity, and toxicity on the region of solid tissue. In certain other embodiments the method comprises deselecting at least one of the plurality of agents based on the evaluating. In certain other embodiments the method comprises selecting at least one of the agents based on the evaluating. In certain other embodiments the method comprises prioritizing at least two of the plurality of agents based on the evaluating. In certain other embodiments the method comprises distributing the plurality of agents to a plurality of positions, each along a respective one of a plurality of parallel axes within a region of solid tissue within each of a plurality of subjects. In certain further embodiments the method comprises one of (i) selecting at least one of the plurality of agents based on the evaluating, (ii) deselecting at least one of the plurality of agents based on the evaluating, and (iii) prioritizing at least two of the plurality of agents based on the evaluating. In certain other embodiments the method comprises one of (i) selecting at least one of the plurality of subjects based on the evaluating, (ii) deselecting at least one of the plurality of subjects based on the evaluating, and (iii) prioritizing at least two of the plurality of subjects based on the evaluating. In certain other embodiments the evaluating comprises determining a level of altered physiologic state of the solid tissue near at least one of the plurality of parallel axes.

In certain embodiments there is provided a method of screening subjects for eligibility to participate in a clinical trial of one or more agents, comprising (a) introducing one or more agents to a region of solid tissue in one or more subjects in vivo by distributing each of said agents to a plurality of positions along an axis within the region in each subject; (b) removing the region of solid tissue from each of said subjects; and (c) evaluating each region removed in (b) for an effect of each agent on the respective position along the axis within the region, wherein either (i) for any given agent or agents presence of a detectable effect of said agent or agents on the solid tissue region from the subject indicates eligibility of the subject for participation in a clinical trial of the agent or agents, (ii) for any given agent or agents absence of a detectable effect of said agent or agents on the solid tissue region from the subject indicates ineligibility of the subject for participation in a clinical trial of the agent or agents, or (iii) both (i) and (ii).

In certain embodiments there is provided a method of rating a candidate agent for development into a therapeutic agent for treating a solid tumor, comprising (a) introducing one or more agents to a region of a solid tumor of known tumor type in each one or more subjects having a tumor of the known tumor type, by distributing each of said candidate agents to a plurality of positions along an axis within the region in each subject; (b) removing the region of solid tumor from each of said subjects; and (c) comparing each region removed in (b) for an effect of each candidate agent on the respective position along the axis within the region, wherein an agent that results in a greater beneficial effect when introduced to the tumor receives a more favorable rating for development into a therapeutic agent for treating the solid tumor, and an agent that results in a lesser beneficial effect when introduced to the tumor receives a less favorable rating for development into a therapeutic agent for treating the solid tumor.

The present invention provides compositions and methods that are useful for the classification and/or stratification of a subject or subject population, including for use in drug discovery and in pharmacogenomics. In these and related embodiments, correlation of one or more indicia of an altered physiological state with a position at which a given candidate agent has been introduced in a solid tumor can be used to gauge the subject's responsiveness to, or the potential efficacy of, a particular therapeutic treatment; related embodiments contemplate this approach for "deselection", or elimination from consideration as potential therapies, of candidate agents in which no evidence of an altered physiological state is detected at a site of introducing in the tumor.

As described herein, determination of levels of at least one indicator of altered physiologic state can also be used to stratify a subject population for eligibility to participate in a clinical trial. These and related embodiments are contemplated as usefully providing advantages associated with evaluation of candidate therapeutic compounds at an earlier stage of development than is currently the case. For instance, it is not currently standard clinical trial practice to establish biomarker parameters (which can be the basis for exclusion of subjects) prior to Phase III studies, whereas the embodiments described herein can provide useful results even in the absence of established biomarker criteria, for example, at Phase II. Accordingly it is envisioned that through the practice of certain presently disclosed embodiments, relevant information on the properties of a candidate agent can be obtained earlier in a solid tumor oncology drug development program than has previously been the case, including in a manner which can time-efficiently and cost-effectively permit elimination from a clinical trial of subjects for whom no response or benefit can be expected based on a nonresponder result for a particular candidate agent.

For example, stratification of a subject population according to levels of at least one indicator of altered physiologic state, determined as described herein, can provide a useful marker with which to correlate the efficacy of any candidate therapeutic agent being used in cancer subjects, and/or to classify subjects as responders, nonresponders or possible responders.

Data Acquisition and Analysis

In some embodiments it is contemplated that the target region in a solid tissue can be imaged using known techniques to evaluate the effects of the agents. The imaging can be by any suitable process or method, including, for example, radiographic imaging, magnetic resonance imaging, positron emission tomography, biophotonic imaging, etc. In some embodiments, the target region can be imaged repeatedly before, during, and after the delivery process.

Upon imaging, the level of the reporting signal can be quantified by methods known to one of skill in the art. Observation and/or quantification of the reporting signal can be used to make informed research and health care decisions regarding the use and efficacy of a therapeutic agent. Non-limiting examples of decisions that can be made on such observations include fluid volume quality control, positional tracking, and drug biodistribution. Such experiments can be performed on a lower mammal, for example, a mouse, to provide reporting signals that can be used to make informed predictions regarding the activity of a potential therapeutic agent in a human. Animal studies of this type can be used to avoid the inherent uncertainty and inaccuracies that arise by conducting drug efficacy studies in cells in controlled environments instead of in the native environment.

Quantification of fluorescence signals can be accomplished by any method known in the art. Fluorescence signals can be compared with a standard or a control to determine up-regulation or down-regulation of a biological pathway. Such observations can be used to make predictions regarding the therapeutic value of drug candidates.

Certain embodiments described herein relate to introducing an agent into a solid tissue in a subject, and/or excising all or a portion of a solid tissue from a subject, and/or obtaining one or more biological samples from a solid tissue that can be in a subject, and/or screening one or more subjects for clinical trial eligibility, and/or any number of other methods that can involve a subject, which includes a subject or biological source.

The subject or biological source can be a human or non-human animal, a transgenic or cloned or tissue-engineered (including through the use of stem cells) organism, a primary cell culture or culture adapted cell line including but not limited to genetically engineered cell lines that can contain chromosomally integrated or episomal recombinant nucleic acid sequences, immortalized or immortalizable cell lines, somatic cell hybrid cell lines, differentiated or differentiatable cell lines, transformed cell lines and the like. In some embodiments of the invention, the subject or biological source can be suspected of having or being at risk for having a malignant condition, and in some embodiments of the invention the subject or biological source can be known to be free of a risk or presence of such disease.

Some embodiments as disclosed herein relate to a method for selective delivery of a fluid-phase agent to a solid tissue. As also noted above, such selective delivery obviates the need for excessive systemic concentrations of therapeutic or candidate agents in order to achieve therapeutically effective concentrations in the desired solid tissue, thereby avoiding clinically detrimental toxicities to uninvolved tissues and also avoiding undesirable side-effects. Related embodiments contemplate the testing of currently non-approved candidate agents through such selective delivery to a solid tissue. Without wishing to be bound by theory, according to these embodiments, direct effects of the candidate agent on the solid tissue (e.g., solid tumor) can be evaluated by in vivo administration followed by ex vivo analysis of excised tissue, without threatening the health of the subject, because the dose used for direct administration into the solid tissue is far lower than the minimal dose that would otherwise be administered systemically. (The minimal dose is the smallest amount of the agent that will produce a desired physiologic effect in the subject.) Given the minute volumes and low pressures of the present modes of fluid administration, and full or partial patency of the solid tissue as a physical property that promotes retention of the administered fluid (also determinable by existing methodologies, e.g., by imaging and/or by use of a detectable label as a tracer), the agent that is selectively administered to the solid tissue according to the present disclosure is either undetectable outside the solid tissue, or if detectable outside the solid tissue, the agent is present at less (in a statistically significant manner) than the minimal dose.

Such considerations pertain in related embodiments, wherein detection in a solid tissue of an altered physiologic state subsequent to introducing an agent or a plurality of agents includes detecting a degree of permeation of the agent(s) through the solid tissue, detecting a degree of absorption of the agent(s) in the tissue, detecting a physicochemical effect of the agent(s) on the tissue, and/or detecting a pharmacological effect of the agent(s) on the tissue. Assays, including fluorescence assays, of drug permeation or penetration in solid tissues are known in the art and have been described (e.g., Kerr et al., 1987 Canc. Chemother. Pharmacol. 19:1 and references cited therein; Nederman et al., 1981 In Vitro 17:290; Durand, 1981 Canc. Res. 41:3495; Durand, 1989 JNCI 81:146; Tunggal et al., 1999 Clin. Canc. Res. 5:1583) and can be configured further according to the present disclosure, for instance, through the detection in histological serial sections of a detectable label that has been co-administered to the solid tissue, prior to excision and sectioning, with an agent of interest.

In such embodiments, permeation or penetration refers to the area of retention of an agent in the solid tissue in the immediate vicinity of the needle from which the agent was introduced exclusive of perfusion (entry into and dispersion via any blood vessel), and can include retention of the agent in extracellular space or extracellular matrix or in association with a cell membrane or intracellularly. Permeation can be distinct from a physicochemical effect, which refers to microscopically detectable mechanical disruption of tissue that results from the needle insertion or fluid injection itself, or from non-biological mechanical or chemical tissue disruption caused by the agent (e.g., damage to cell membranes or disintegration of cell-cell junctions). Pharmacological effects include statistically significant alterations of a cell or tissue physiological state that are detectable as consequences of the molecular mechanism of action of the agent, for example, cytoskeletal reorganization, extension or withdrawal of cellular processes, or evidence of biological signal transduction as can be detected using any of a number of known cytological, biochemical, molecular biological or other read-outs. Comparison of serial sections can permit distinguishing the nature of the effect that is detected histologically.

Some embodiments include those in which the solid tissue comprises a tumor, wherein agent delivery can be made to, and/or sample retrieval can be made from, the solid tumor. It will be appreciated by persons familiar with the art from the disclosure herein that in the course of practicing certain embodiments described herein, a selected region of a tumor can comprise the site into which the needles of the presently described devices are inserted, introduced or otherwise contacted with the tumor. The region can be selected on any number of bases, including based on imaging that can be conducted before, during or after a step of needle insertion, introduction or contacting, or based on imaging conducted before, during or after excising the solid tissue from a subject, or based on other criteria including but not limited to anatomic location, accessibility in the course of a surgical procedure, degree of vascularization or other criteria.

Solid tumors of any type are contemplated as being suitable for intervention using the devices described herein. In some embodiments, the solid tumor can be a benign tumor or a malignant tumor, which can further be a primary tumor, an invasive tumor or a metastatic tumor. Certain embodiments contemplate a solid tumor that comprise one of a prostate cancer cell, a breast cancer cell, a colon cancer cell, a lung cancer cell, a brain cancer cell and an ovarian cancer cell, but the invention is not intended to be so limited and other solid tumor types and cancer cell types can be used. For example, the tumor can comprise a cancer selected from adenoma, adenocarcinoma, squamous cell carcinoma, basal cell carcinoma, small cell carcinoma, large cell undifferentiated carcinoma, chondrosarcoma and fibrosarcoma, or the like. As also noted elsewhere herein, art-accepted clinical diagnostic criteria have been established for these and other cancer types, such as those promulgated by the U.S. National Cancer Institute (Bethesda, Md., USA) or as described in DeVita, Hellman, and Rosenberg's. Cancer: Principles and Practice of Oncology (2008, Lippincott, Williams and Wilkins, Philadelphia/Ovid, New York); Pizzo and Poplack, Principles and Practice of Pediatric Oncology (Fourth edition, 2001, Lippincott, Williams and Wilkins, Philadelphia/Ovid, New York); and Vogelstein and Kinzler, The Genetic Basis of Human Cancer (Second edition, 2002, McGraw Hill Professional, New York). Other non-limiting examples of typing and characterization of particular cancers are described, e.g., in Ignatiadis et al. (2008 Pathobiol. 75:104); Kunz (2008 Curr. Drug Discov. Technol. 5:9); and Auman et al. (2008 Drug Metab. Rev. 40:303).

According to certain presently contemplated embodiments, the efficacy of a therapeutic agent can be identified by detecting an altered physiologic state as provided herein, including by assessing any of a number of biological parameters characteristic of a cancer cell such as those reviewed by Hanahan and Weinberg (2000 Cell 100:57) and in the references cited therein. There are characteristics of cancer cells that are useful in determining the effect of a candidate agent on one or more traits exhibited by cancer cells, and detectable by any of a variety of techniques known to the art for determining one or more of (i) an ability to evade apoptosis, (ii) acquisition of self-sufficiency in growth signals, (iii) insensitivity to growth-inhibitory signals, (iv) acquisition of tissue invasive and metastatic phenotype, (v) unlimited replicative potential, and (vi) sustained angiogenesis. Persons skilled in the art are familiar with multiple approaches for detecting the presence of these alterations of physiologic state, which can be adapted to a particular excised tumor system. See, e.g., Bonificano et al. (Eds.) Current Protocols in Cell Biology, 2007 John Wiley & Sons, NY; Ausubel et al. (Eds.) Current Protocols in Molecular Biology, 2007 John Wiley & Sons, NY; Coligan et al. (Eds.), Current Protocols in Immunology, 2007 John Wiley & Sons, NY; Robinson et al. (Eds), Current Protocols in Cytometry, 2007 John Wiley & Sons, NY. Non-limiting examples of parameters that can be assayed to identify an altered physiologic state include assays of cell viability, cell division, apoptosis, necrosis, cell surface marker expression, cellular activation state, cellular elaboration of extracellular matrix (ECM) components or of ECM-degrading enzymes, morphometric analysis, extension or retraction of cellular processes, cytoskeletal reorganization, altered gene expression, e.g., by in situ hybridization of immunohistochemistry (e.g., Shibata et al., 2002 J. Anat. 200:309) intracellular phosphoprotein localization (e.g., Gavet et al., 1998 J Cell Sci 111:3333), and the like.

In some cases, the selection/deselection of an agent is based on cell apoptosis. The threshold for selecting or deselecting of an agent based on cell apoptosis may depend upon the cancer therapeutic agent used, and/or the nature or size of the tumor. For example, the experiment may be carried out by simultaneously delivering a fluidic solution containing an agent and a control (the same solution without the agent control) to adjacent positions of a solid tissue. After a selected period of time, the effect of the agent or control on cell apoptosis is then compared. In some embodiments, the cancer therapeutic agent is deselected from further evaluation if less than about 1%, about 3%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% cell apoptosis is observed comparing to the control without the cancer therapeutic agent. In some other embodiments, the cancer therapeutic agent is selected for further evaluation if more than about 1%, about 3%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% cell apoptosis is observed comparing to the control without the cancer therapeutic agent.

The present disclosure provides methods of evaluating an effect of an anti-cancer or an anti-tumor agent on a solid tissue of a subject, in particular solid tumor. In some embodiments, the evaluation is bases on the analysis of an effect of the agents on a region of within about 15, 14, 13, 12, 11, 10, 9, 8, 7, 6, 5, 4, 3, 2.5, 2, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1 or 0.05 mm of the site of agent delivery. The effect may be an altered physiological state, the present or absence of a biomarker or cell apoptosis. Based on the evaluation, the agent and/or the subject may be selected or deselected for further studies.

The present disclosure also relates to methods of distributing at least one agent at different concentrations to adjacent positions within a solid tissue. In some embodiments, one agent is distributed at 2, 3, 4, 5, 6, or even more different concentrations to adjacent positions within the solid tissue. After a selected period of time, the solid tissue is resected and evaluated. The selected period of time may be at least 6, 12, 18, 24, 36, 48, 72, 96 hours or even longer. Based on the evaluation, a minimal concentration of the agent to have an effect on the solid tissue may be determined. For example, in the case of a tumor, a minimal concentration for a potential anti-tumor agent to have an anti-tumor effect may be determined by injecting the agent at different concentrations into the tumor. This information may help physicians to design optimal dosing regimen for a patient.

Figure 6:
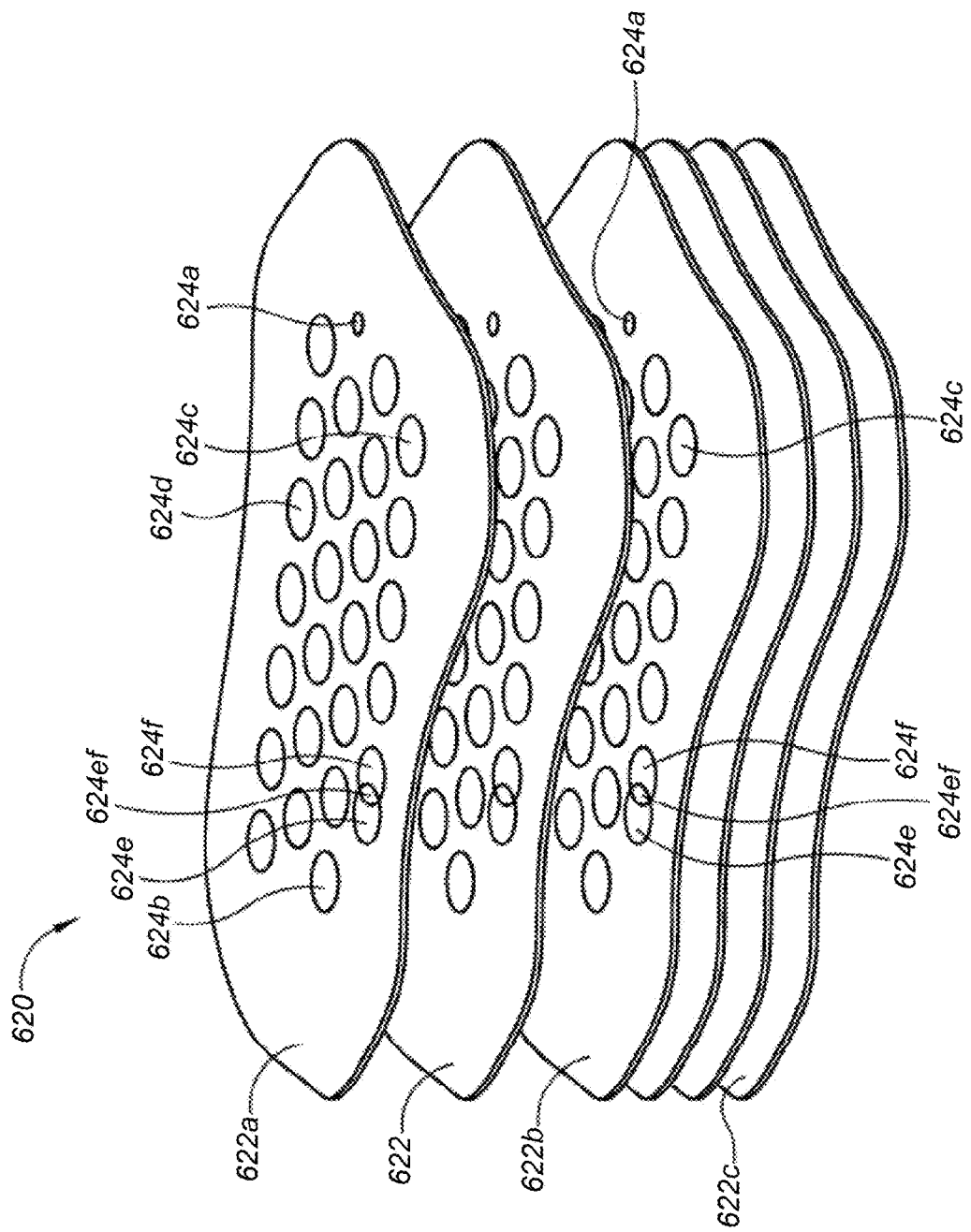
FIG. 6 shows diagrammatically a portion of a tumor illustrating principles of the invention.

FIG. 6 illustrates one embodiment of the present invention. A portion of tumor 620 has been sectioned into a plurality of slices 622 along planes that lie substantially normal to the delivery axes. Column-shaped delivery regions 624 define the regions of permeation of the respective agents, and extend perpendicular to the planes of the sections 622.

Many of the regions 624 may not be easily detectable to a user, so generally at least two readily detectable position markers 624a, 624b are among the agents injected, at widely separated locations. In some cases, the detectable position markers are coinjected with at least one additional agent. The user can then overlay a template on which the locations of each of the delivery axes is marked, aligning the indicated marker positions of the template with the detectable position markers 624a, 624b of a given section 622, thereby locating the remaining delivery regions 624. The position markers 624a, 624b can be any composition that is detectable by a user. Various exemplary position markers are described in detail elsewhere in this disclosure. According to an embodiment, the position markers are selected to resist permeation and diffusion into the surrounding tissue and to remain concentrated in a narrow column, as shown for example at 624a, so as to be detectable for an extended period after the injection procedure, and to provide an accurate guide for positioning the template. Alternatively, the position markers 624a, 624b may be a color stain coated on a needle or a microdialysis probe. The insertion of the needle or microdialysis probe may lead to stain of a solid tissue at the site of insertion. Additionally, in the case of microdialysis probe, a colored string may be attached to a microdialysis probe. After delivering an agent to a solid tissue, the microdialysis probe is pulled through the solid tissue, leading to the staining of the site of injection by the colored wax string.

In addition to position markers, control agents may also be among the agents injected. For example, a negative control can comprise a substance used as a vehicle in others of the agents, and a positive control can comprise a compound of most or all of the agents delivered individually at other delivery axes.

Following sectioning of the tumor 620, a user conducts selected assays on delivery regions 624 of various sections 622 of the tumor 620, as described in more detail later. One benefit of the devices and methods disclosed herein is that, in addition to evaluating the efficacy of a given agent on the tumor, the efficacy of agents at various delivery regions 624 can be evaluated and compared. Additionally, the effect of a given agent on various parts of the tumor can be evaluated, both vertically and horizontally. By comparing the effect of an agent in a delivery region 624c at section 622a, for example, with its effect in the same region 624c at sections 622b and 622c, the effect of that agent on different tissue compositions that may occur vertically can be differentiated. Similarly, the same agent can be delivered at several delivery axes in the array, e.g., 624c and 624d, and the relative effects at those locations in a given section 622 can then be compared, providing horizontal differentiation. As is well known in the art, biological tissue is rarely homogeneous over even relatively small distances. A given agent might have substantially no effect on some tissue structures of a tumor, but might, on the other hand, be extremely effective on others. Such differential effects can be detected and evaluated as described above.

Another valuable aspect that can be evaluated is the effect of multiple agents in regions where they interact within the tissue. Delivery regions 624e and 624f are spaced more closely together than the others, resulting in the respective agents interacting in a region 324ef where the respective delivery regions overlap.

Biomarkers

The present disclosure exemplifies a method for evaluating changes in the physiological status of tumor cells or tumorigenic cells by measuring the biomarkers secreted by the cells. Cells may communicate and respond to physiological cues by secreting the biomarkers that can be soluble factors including autocrines, paracrines, or endocrines. Tumor cells or tumorigenic cells may secrete a plurality of biomarkers that are known in the medical arts before, during or after a change of the physiological status. The biomarkers can be proteins, peptides, amino acids, RNA, DNA, nucleic acids, proteoglycans, lipids, small organic molecules, small inorganic molecules, or ions. In some embodiments, the biomarkers can be measured in transcriptional levels as gene expressions or in protein levels. By measuring and detecting the biomarkers described herein over time, and relating the measurement to the biomarkers known in the medical art, thereby the physiological status or the changes in the physiological status of the tumor cells or tumorigenic cells, such as cell death, cell proliferation, cell signaling process or cellular responses, can be determined.

The death of tumor cells or tumorigenic cells can be via apoptosis or necrosis. Apoptosis is a process of programmed cell death, and may be activated via either the death receptor-mediated extrinsic pathway or the mitochondria-directed intrinsic pathway. Non-limiting examples of biomarkers of apoptosis that can be measured in gene expressions or protein levels include: activated caspase family such as caspases 2, 3, 7, 8, 9 and 10; tumor protein 53 (p53), phosphor-p53, p73, cyclin-dependent kinase inhibitor 1 (p21-waf1), and phosphor-H2AX/Ser 139 (pH2AX); B-cell lymphoma 2 (Bcl-2) family members such as Bcl-2, B-cell lymphoma-extra large (Bcl-XL), Bcl-xs, Bcl-W, and induced myeloid leukemia cell differentiation protein (Mcl-1); pro-apoptotic protein family such as Bcl-2-associated X protein (Bax), and Bcl-2 homologous antagonist/killer (Bak); Bcl-2 homology (BH) domain family such as BH1, BH2, BH3, BH4, Bcl-2-associated death promoter (Bad), p53 upregulated modulator of apoptosis (PUMA), NOXA, Bcl-2 modifying factor (Bmf), Bcl-2 interacting killer (Bik), Bcl-2-related ovarian killer (Bok), Bcl-2 interacting mediator of cell death (Bim), and BH3 interacting-domain death agonist (Bid); modulators of apoptosis proteins such as apoptotic protease activating factor 1 (APAF-1), apoptosis inducing factor (AIF), inhibitors of apoptosis (IAP) such as cIAP1, cIAP2, Cp-IAP, Op-IAP, XIAP, NAIP, survivin, and second mitochondria-derived activator of caspases (SMAC); markers to measure extent of DNA oxidative damage such as 8-hydroxy-2-deoxyguanosine and 3-nitrotyrosine; other biomarkers related to apoptosis such as cytochrome c, N-hydroxy-L-arginine (NOHA), 14-3-3 protein, tumor necrosis factor (TNF)-related apoptosis inducing ligand (TRAIL), reactive oxygen species (ROS), externalized phosphatidylserine, cytokeratins, poly(ADP-ribose) polymerase, nucleosomal DNA, apoptosis antigen 1 (Apo-1), TNF receptor superfamily, member 6 (Fas), Fas ligand (FasL), Fas-associated death domain protein (FADD), phosphorylated-FADD, glutathione-S-transferase-isoenzyme π (Gst-π), β-galactosidase, phosphorylated retinoblastoma suppressor protein and the like.

Necrosis is a premature death of cells or tissues, and may be caused by factors external to the cells or tissues. Other physiological events such as inflammatory responses of the cells may be triggered with necrosis. Non-limiting examples of biomarkers related to necrosis of tumor cells or tumorigenic cells that can be measured in gene expressions or protein levels include tumor necrosis factor (TNF), cachexin, cachectin, lymphotoxin, cyclophilin A, interleukin-1, 2, 3, 4, 5, 6, 7, 8, 9, 10, 11, 12, 13, 14, 15, 16 and 17, alpha1-antitrypsin, copeptin, myeloperoxidase, FLICE-like inhibitory protein (FLIP), transducer and activator of transcription (STAT), tumor necrosis factor receptor superfamily, member 19 (TROY), cyclooxygenase (COX)-1, COX-2, cell death factors, macrophage inflammatory proteins, macrophage activating factors, macrophage migration inhibitory factors, neuroleukin, immunologic suppressor factors, transfer factors, oncostatin, osteopontin, interferon type I, interferon gamma, interleukin 1 receptor antagonist protein, CD70, CD30, CD40, 4-1BB ligand, ectodysplasins, B-cell activating factor, receptor activator of nuclear factor kappa-B ligand (RANKL), lymphotoxin and the like.

In addition to measuring the biomarkers that can be related to cell death, the current disclosure further provides a method to measure biomarkers that can be measured in gene expressions or protein levels to relate to the proliferation/growth or mitotic activities of tumor cells or tumorigenic cells. Non-limiting examples of biomarkers described herein include Akt protein kinase B, Wilms tumor marker, retinoblastoma (Rb), Ki-67, proliferating cell nuclear antigen (PCNA), serine/threonine kinase, mammalian target of rapamycin (mTOR), neurotrophin, protein Mis18 beta, myostatin, cyclin dependent kinases (Cdk) 1, 2, 4, and 6, cyclin dependent kinase comples 2 (Cdc2 p34), cyclin D1, cyclin D2, cyclin D3, cyclin E, cyclin A, growth differentiation factors 1, 2, 3, 5, 6, 9, 10 and 15 and the like.

The physiological status of a cell may be heavily modulated by a plurality of signal transduction pathways. Signal transduction occurs when an extracellular signaling molecule or a ligand binds to and further activates a cell surface receptor, thereby altering intracellular molecules creating a response. In some preferred aspects, the biomarkers related to signal transduction changes of tumor cells or tumorigenic cells can be measured in gene expressions or protein levels. The biomarkers described herein can participate in the signaling pathways as growth factors, enzymes, signaling factors, ligands, intermediate molecules generated in biological pathways, hormones, nutrients, transmembrane proteins, extracellular matrix proteins, intracellular components, downstream factors of protein phosphorylation and the like. Non-limiting examples of signal transduction biomarkers include human epidermal growth factor receptor (HER) family molecules such as HER1, 3, and 4; phosphatidylinositol 3-kinases (PI3K)/protein kinase B (Aid) signaling pathway molecules as PI3K/AKT, microtubule-associated protein kinase (MAPK)/extracellular signal-regulated kinase (ERK) pathway molecules such as MAPK, mitogen-activated protein kinase (MEK), Ras, proto-oncogene serine/threonine-protein kinase (RAF), ERK1 and 2; hedgehog pathway proteins such as sonic hedgehog, desert hedgehog, indian hedgehog, hedgehog-interacting protein, smoothened protein (SMO), Gli-1, Gli-2, Gli-3, and forkhead box O (FoxO)-1; Wnt signal transduction pathway modulators such as Wnt1, 2, 2B, 3, 3A, 4, 5A, 5B, 6, 7A, 7B, 8A, 8B, 9A, 9B, 10A, 10B, 11, 16, Wnt1-inducible-signaling pathway protein 1 (Wisp-1), Wisp-2, and β-catenin; parathyroid hormone-related proteins such as hypercalcemic hormone of malignancy, parathyroid hormone like tumor factor; phosphatase and tensin homolog (PTEN), serine/threonine-protein kinase (SGK3), eukaryotic translation initiation factor 4E-binding protein 1 (4E-BP1), tymidine kinase, growth hormone, pyruvate dehydrogenase lipoamide kinase isozyme 1 (PDK1), citrate, nitride oxide, P70S6 kinase, glycogen synthase kinase 3 (GSK-3), Src homology 2 domain containing (SHC)-transforming protein 1, CD117, platelet-derived growth factor receptor (PDGFR)-α, PDGFR-β, vascular endothelial growth factor receptor-2 (VEGFR-2), epidermal growth factor receptor (EGFR), matrix metalloproteinase (MMP)-1, CD9, keratin 7, p27, parafibromin, BMI1 polycomb ring finger oncogene (Bmi-1), 14-3-3σ, cystatin-SA, epididymal secretory protein E4, whey acidic protein (WAP) four-disulfide core domain protein 2 (WFDC2), adiponectin, leptin, resistin, agouti signaling protein, agouti-related protein, angiopoietins, angiostatic proteins, cysteine-rich protein 61, nephroblastoma overexpressed protein, peptide PHI, peptide YY, insulin, glucose, pituitary hormones, placental hormones, relaxin, secretin, urocortins, urotensins, vasoactive intestinal peptide, autocrine motility factor, beta-thromboglobulin, leukemia inhibitory factor, leukocyte migration-inhibitory factors, lymphotoxin-alpha, endothelin, enphrin, bradykinin, kininogens, tachykinins, chemokines such as chemokine C, CC, CXC, CX3C and the like.

In certain aspects, the biomarkers capable of triggering a signal transduction pathway, in turn altering a cellular response can be a growth factor. Non-limiting examples of growth factors that can be measured in gene expressions or protein levels to relate tumor cells or tumorigenic cells to a physiological status include erythropoietin (EPO), angiopoietin (Ang), stem cell factor (SCF), vascular endothelial growth factor (VEGF), fibroblast growth factor (FGF), nerve growth factor (NGF), hematopoietic cell growth factor, hepatocyte growth factor, hepatoma-derived growth factor, migration-stimulating factor, autocrine motility factor, epidermal growth factor (EGF), insulin-like growth factor 1 (IGF-1), transforming growth factor (TGF), cartilage growth factor (CGF), keratinocyte growth factor (KGF), skeletal growth factor (SGF), osteoblast-derived growth factor (BDGF), cytoline growth factor (CGF), colony stimulating factor (CSF), integrin modulating factor (IMF), platelet-derived growth factor (PDGF), calmodulin, bone morphogenic proteins (BMP), tissue inhibitor matrix metalloproteinase (TIMP), and the like.

In certain embodiments, the biomarkers are immunohistochemistry (IHC) markers. Non-limiting examples of IHC markers that can be measured include hematopoetic markers, breast markers, carcinoma or mesothelial markers, colon markers, central nervous system markers, infectious disease markers, keratin or epithelial markers, lung markers, melanocytic markers, neuroendocrine markers/other hormones, other organ-related markers, prognostic other markers, prostate markers, stromal markers or tumor markers. Hematopoetic markers include, but not limited to: annexin A1, BCL2 follicular lymphoma marker, BCL6 follicle center B cell marker, CD10, CD20, CD23, CD79a, cyclin D1, hairy cell leukemia marker, multiple myeloma oncogene 1, PAX-g B cell transcriptional factor, ZAP 70, CD34, CD68, CD99, CD117, glycophorin-A, myeloperoxidase, terminal deoxynucleotidyl transferase, von willebrand factor VIII, anaplastic lymphoma kinase-1, CD15, CD30, fascin, CD45, CD138, kappa immunoglobulin light chains, lambda immunoglobulin light chains, plasma cell p63, CD1a, CD2, CD3, CD4, CD5, CD7, CD8, CD43, CD56, CD57 and granzyme B. Breast markers include, but not limited to: Akt protein kinase, cytokeratin 5, p63, epithelial antigen, cathepsin D, cytokeratin 8, HMW cytokeratin high molecule weight, cytokeratin 5/6, cytokeratin 7, cytokeratin 19, cytokeratin 20, E-cadherin, estrogen receptor, HER2/neu, Ki67 cell proliferation marker, p53 tumor suppressor gene protein, progesterone receptor and smooth muscle actin. Carcinoma or medothelial markers include, but not limited to: BER-EP4 epithelial antigen, calretinin, ERA epithelial related antigen, cervical or gynecological markers, p16 tumor suppressor gene protein, ProEx C biomarker, TAG72 and wilms tumor marker. Colon markers include, but not limited to: epidermal growth factor receptor, CDX2, microsatellite instability marker such as MLH1, MSH2, MSH6, PMS2 and p53. CNS markers include, but not limited to: human glial fibrillary acidic protein and neurofilament. Infectious disease markers include, but not limited to: cytomegalovirus, herpes simplex virus type I, II, pylori H and *varicella zoster* virus. Keratin and epithelian markers include, but not limited to: cytokeratin 5/6, cytokeratin 7, cytokeratin 8/18, cytokeratin 19, cytokeratin 20, cytokeratin high molecular weight, caldesmon smooth muscle, p63, collagen 9, smooth muscle myosin, cytokeratin cocktail and epithelial membrane antigen. Lung markers include, but not limited to: 34BE12, HMW cytokeratin high molecular weight, excision repair cross complementing polypeptide, synaptophysin and thyroid transcription factor-1. Melanocytic markers include, but not limited to: HMB melanoma associated marker 45, melanoma cocktail, melanoma associated marker 1, s100 protein and tyrosinase. Neuroendocrine markers and other hormones include, but not limited to: androgen receptor, calcitonin, chromogranin A, G cell antral pyloric mucosa, neuron-specific enolase, somatostatin and synaptophysin. Other organ-related markers include, but not limited to: CEA carcinoembryonic antigen, calectin-3, gross cyctic disease fluid protein 15, hepatocyte antigen, adrenal cortical inhibin and renal cell carcinoma marker. Prostate markers include, but not limited to: PIN2 cocktail, PIN4 cocktail, prostate specific antigen, prostatic acid phosphorase and p504s gene product. Stromal markers include, but not limited to: CD31, podoplanin, DOG1 derived from GIST1, desmin filament protein, factor XIIIa fibrohistocytic, human herpesvirus type 8, muscle specific actin, myogenin muscle marker, myoglobin cardiac and skeletal marker, s100 protein, smooth muscle actin, smooth muscle myosin and vimentin. Tumor markers include, but not limited to: alpha detoprotein, Ca 19-9 CI, Ca-125 epitheliod malign marker and survivin.

In some embodiments, the biomarkers that can be measured in gene expressions or protein levels are metabolites or metabolic biomarkers. Non-limiting examples of metabolites or metabolic biomarkers include: adenosine triphosphate (ATP), adenosine diphosphate (ADP), adenosine monophosphate (AMP), cyclic adenosine monophosphate (cAMP), Guanosine-5'-triphosphate (GTP), Guanosine-5'-diphosphate (GDP), Guanosine-5'-monophosphate (GMP), nicotinamide adenine dinucleotide phosphate (NADP), NADPH, nicotinamide adenine dinucleotide (NAD), NADH, proliferating cell nuclear antigen, glucose, glucose-6-phosphate, fructose-6-phosphate, fructose 1,6-b phosphate, ribose-5-phosphate, erythrose-4-phosphate, xylulose 5-phosphate, glyceraldehyde-3-phosphate, sedoheptulose 7-phosphate, 3 ribulose-5-phosphate, 1 ribose-5-phosphate, phosphoenolpyruvate, 2-phosphoglycerate, 3-phosphoglycerate, 1, 3-phosphoglycerate, dihydroxyacetone phosphate, malate, oxaloacetate, ketoglutarate, lactate, glutamine, alanine, glutamate, pyruvate, fatty acids, acetyl-coA, citrate, glycerol, uric acid, cholesterols, eicosanoids, glycolipids, phospholipids, shpingolipids, steoid, triacylglycerols, albumin, insulin, diols, Ros, NO, bilirubin, phosphor-creatine, ketone bodies, L-ornithine, argininosuccinate, fumarate, L-arginine, urea, carbamoyl phosphate, ornithine, citrulline, histidine, isoleucine, leucine, lysine, methionine, phenylanine, threonine, tryptophan, valine, asparagines, aspartic acid, cysteine, glutamic acid, glycine, proline, selenocysteine, serine, taurine, tyrosine, citric acid and the like.

In some embodiments, the biomarkers could be ions. Non-limiting examples include hydrogen, potassium, sodium, calcium, chloride, magnesium, bicarbonate, phosphate, hydroxyl, iodine, copper, iron, zinc, sulfate and the like.

EXAMPLES

Example 1

Figure 7:
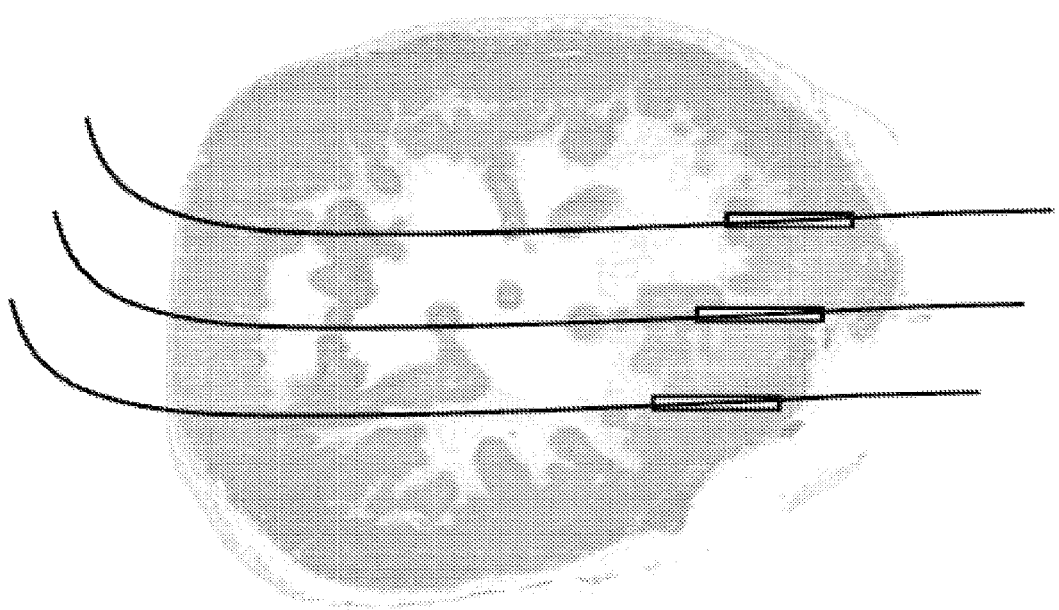
FIG. 7 shows an example of targeting the viable EBC-1 tumor epithelium expressing the target of interest (c-Met) using a linear array of microdialysis probe embodying principles of the present invention.

FIG. 7. shows an example of targeting the viable EBC-1 tumor epithelium expressing the target of interest (c-Met) using a linear array of microdialysis probes. The length of the probe/membrane can be controlled, allowing delivery of the therapeutic agents mainly to the proliferative zone of the tumor. The image is of an H&E stained slice from an EBC-1 cell line xenograft. EBC-1 cells are a lung cancer cell line with a c-Met amplification. These xenografts grow rapidly in nude mice and develop central regions of necrosis and a-cellularity as shown in white. To assess the action of a compound meant to target c-met it is necessary to direct the compound to the actively proliferating zone near the periphery of the tumor. The drawing demonstrates how microdialysis probes can be strung through the tumor and placed in only the peripheral area f the tumor, thus allowing for proper assessment of a compound(s) activity on only the tissue of interest and not regions of the tumor irrelevant to the action of the compound.

Example 2

Figure 8:
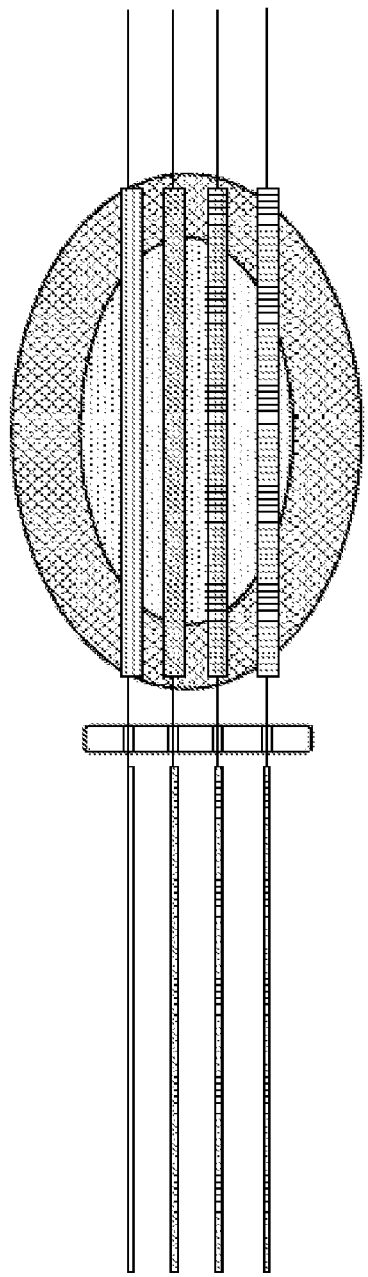
FIG. 8 shows a schematic example of monitoring multiple zones/microenvironments in a solid tumor using long microdialysis membranes in vivo embodying principles of the present invention.

FIG. 8 shows an example of sampling multiple zones/microenvironments in solid xenograft tumors using long microdialysis membranes. Through the use of long microdialysis membranes, the entire dimension of the solid tumor and the proliferative gradient and multiple microenvironments are dosed. This represents a more complete 3-dimensional dosing than current techniques. In this image the outer circle represents the typically more proliferative zone of a tumor and the inner circle represents the often less active and more tightly packed center of a tumor. Here the drawing shows how longer microdialysis probes can be strung through the entire length of the tumor, thus allowing for delivery of compound into each of the various tissues/zones of a single tumor to evaluate differential effects of a compound or multiple compounds given variations in local tumor environment.

Example 3

Figure 9:
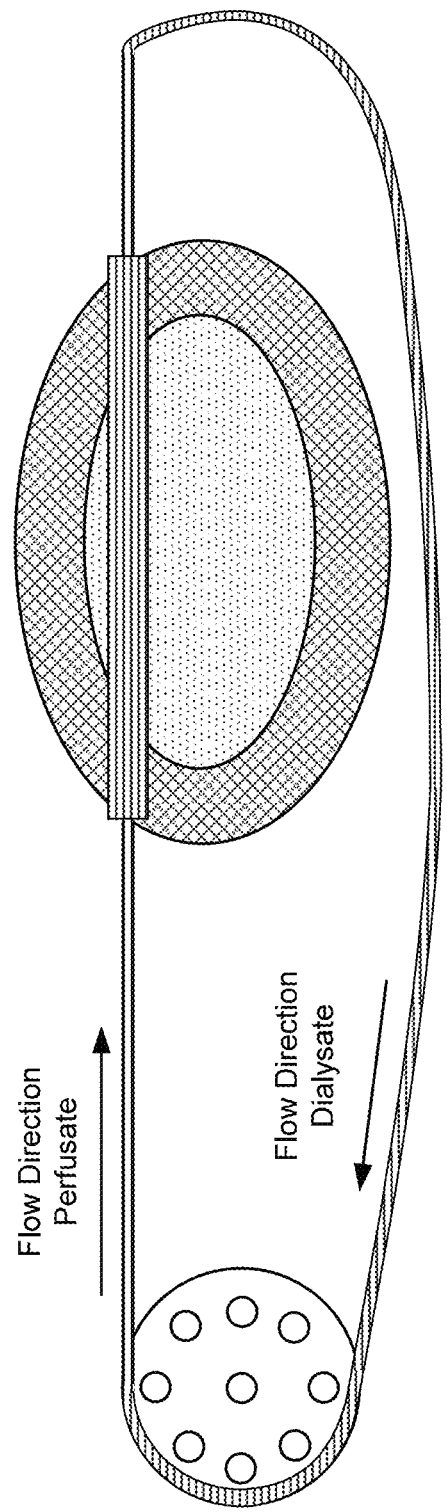
FIG. 9 shows a diagrammatic view of dose determination using microdialysis probes embodying principles of the present invention. By running a continuous loop of drug for a fixed time, the total dialysate from tubing can be collected and analyzed using HPLC, fluorescence/absorbance, etc. to determine the amount of therapeutic agents delivered through passive diffusion.

FIG. 9 shows a diagrammatic view of dose determination using microdialysis probes. By running a continuous loop of drug for a fixed time, the total dialysate from tubing can be collected and analyzed using HPLC, fluorescence/absorbance, etc. to determine the amount of therapeutic agents delivered through passive diffusion. In this drawing the tumor is represented by the two shaded circles, one inside the other. The microdialysis probe is shown as the column strung from one side of the tumor to the other with a closed loop of tubing connected to the microdialysis probe and passing through a peristaltic pump represented by the wheel at the bottom. This set up allows for a known concentration of compound to be introduced into the closed system. In this system one can deliver compound either passively or actively to the tumor as well as collect signaling molecules from the tumor into the closed loop system. Thus after a given amount of time the fluid in the closed system can be collected and analyzed to determine exact amounts of drug delivered to the tumor, by determining the difference in starting concentration and ending concentration, as well as changes over time in molecules extruded from the tumor into the microdialysis probe.

Example 4

Figure 10:
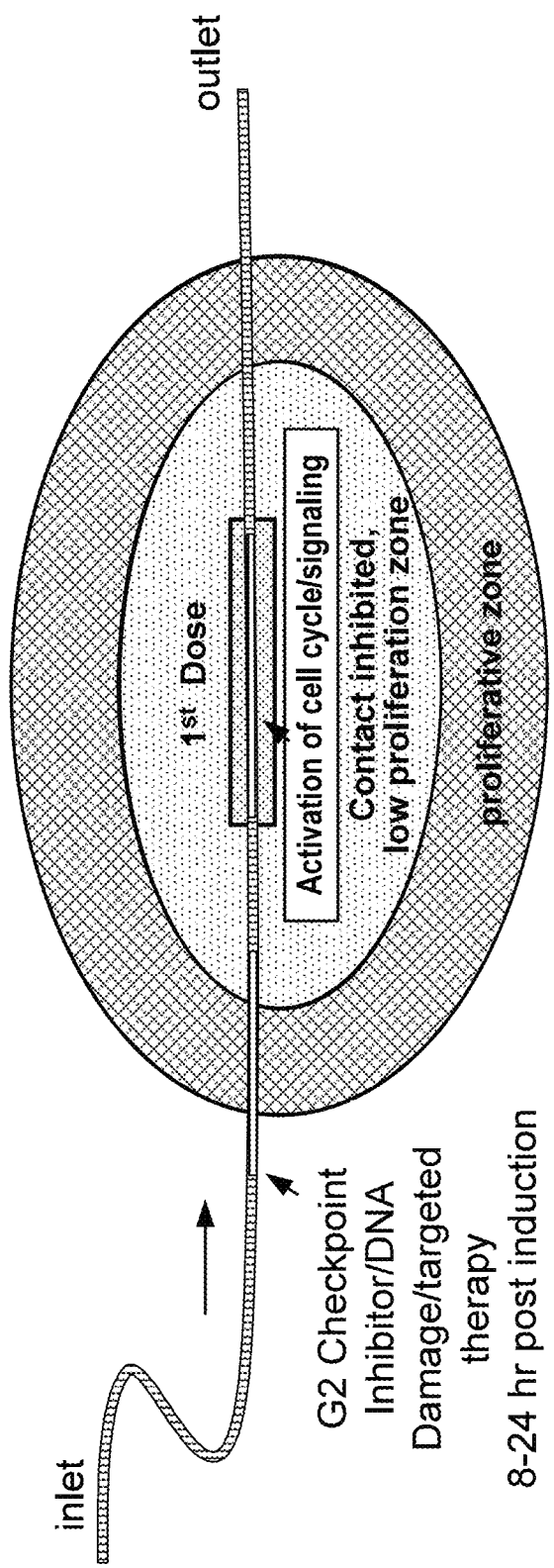
FIG. 10 shows a diagrammatic view of testing the efficacy of anti-cancer drugs given in a particular sequence embodying principles of the present invention. In a first dose, cell cycle/signaling is activated in a contact-inhibited low proliferation zone. After some time and clearing of the first drug from the microdialysis tubing, a second drug that arrests and kills cells that are now actively dividing is administered.

FIG. 10 shows a diagrammatic of a multiple dosing system utilizing microdialysis membranes. In this case the probe is targeted to the interior non-proliferative zone of the tumor. The first dose through the probe would deliver compounds designed to activate cell cycling in these previously arrested cells. The second dose of a different compound would then be delivered at some time in the future to assess the effects on those cells that have reentered the cell cycle. This technique allows for the engineering of new cell states within the tumor that may arise during natural tumor progression, and the subsequent assessment of compound efficacy on those new cell states.

Example 5

Figure 11:
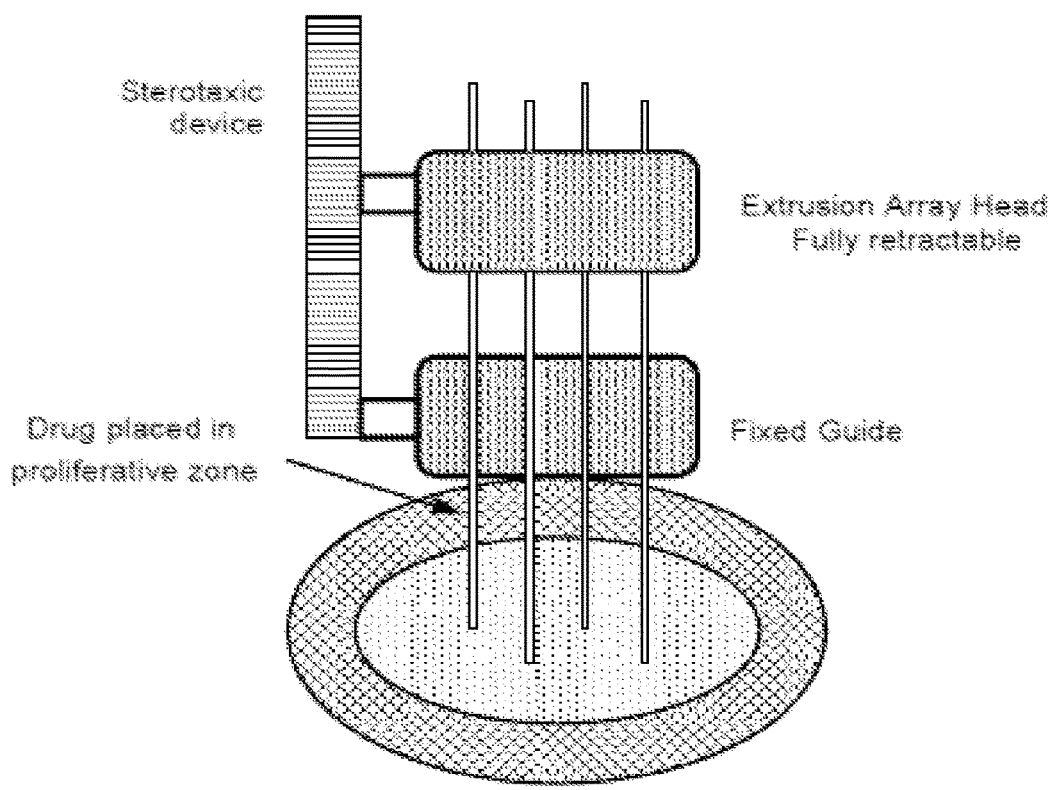
FIG. 11 shows a schematic view of targeting both the proliferative zone and other zones in a solid tumor model using the extrusion/injection technique embodying principles of the present invention.

FIG. 11 shows a diagrammatic view of targeting the proliferative zone in solid tumor models using the extrusion/injection technique. Fixed guide keeps tumor from pulling up with needles during the extrusion injection; depth and length of drug placement are dictated by insertion and extrusion/delivery distances. In this drawing the shaded circles inside each other represent the tumor. Shown here are needles represented by the vertical lines running through the shaded boxes labeled "fixed guide" and "extrusion array head". These needles are attached to the "extrusion array head and are passing through holes in the "fixed guide" in the same orientation as the needles. This setup allows for the parallel placement of multiple needles and multiple columns of drug as well as precise placement of those needles into various zones of the tumor. Placement of the needles is accomplished through the attached sterotacxic device, which is attached to the "extrusion array head", that can be raised/lowered in micrometer increments depending on where in the tumor one desires to place compound. The "fixed guide" which the needles pass through assures that both the needles stay in the same orientation to each other as well as securing the tumor in place as the needles are moved through it.

Example 6

Figure 12:
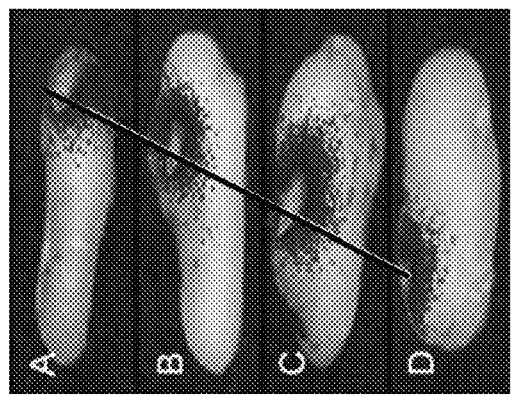
FIG. 12 shows fluorescent imaging of near infrared (NIR) dye delivered in tumor using a microdialysis probe. A, B, C and D designate various cross-sections embodying principles of the present invention.
Figure 12:
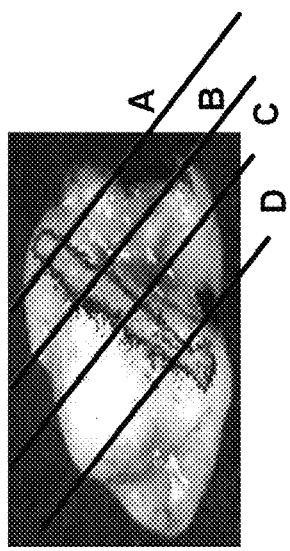
Figure 12:
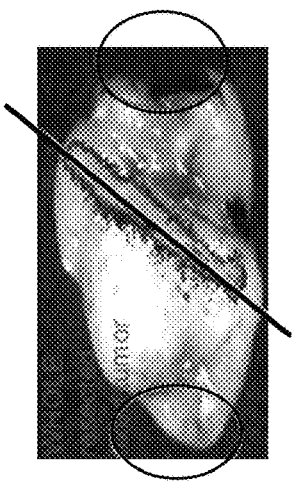

FIG. 12 shows an example of microdialysis probe inserted along a particular axis within the tumor. The entrance points were marked on the outside of solid tumor, and the mass was imaged via IVIS Spectrum for VivoTAG 680-S from Perkin Elmer, 24 hrs post-injection.

Example 7

Figure 13:
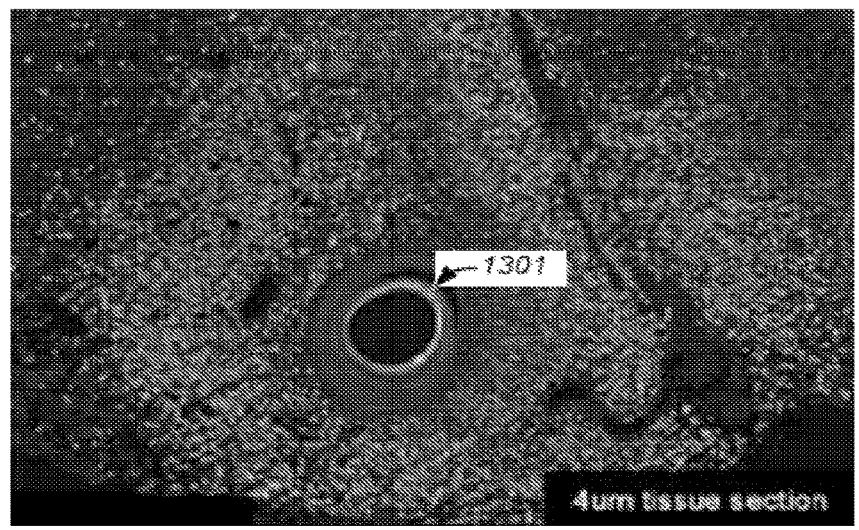
FIGS. 13a and 13b show drug delivered through microdialysis probe induces spatially restricted drug specific tumor cell death embodying principles of the present invention.
Figure 13:
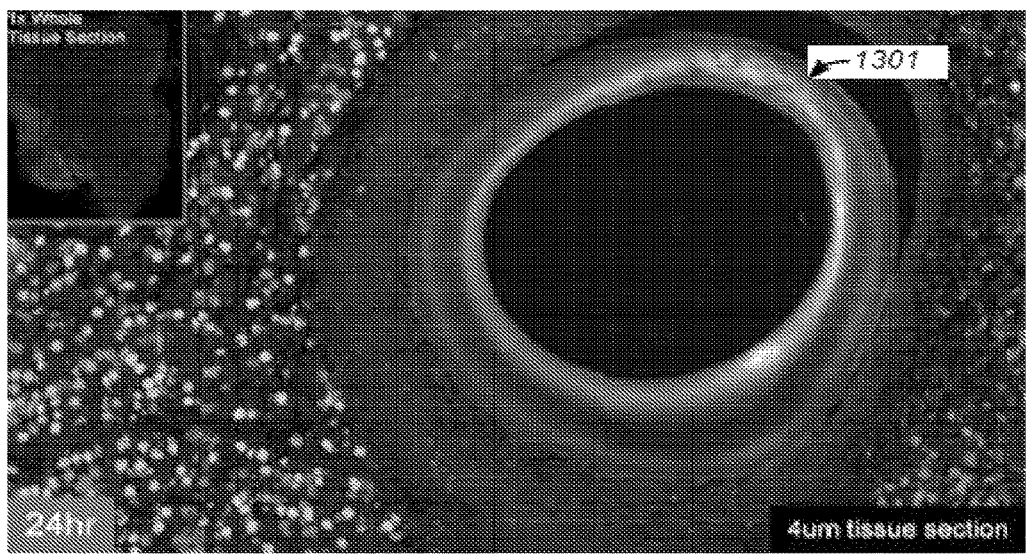

FIG. 13 shows placement of an agent in the solid tissue with clear manifestation of triggered cellular response. There was a even biomarker expression pattern around the delivery axis, demonstrating even agent distribution to the surrounding tissue. Little or no evidence of tissue disruption due to insertion was observed. The membrane maintained its integrity through insertion and tissue processing, including microtome sectioning. The solid tumor is a mouse xenograft of Human Lymphoma Ramos cell line. The biomarkers are DAPI for nuclear stain and Cleaved Caspase 3 Fluorophore 555 for cell death in response to Vincristine as delivery agent.

Example 8

Figure 14:
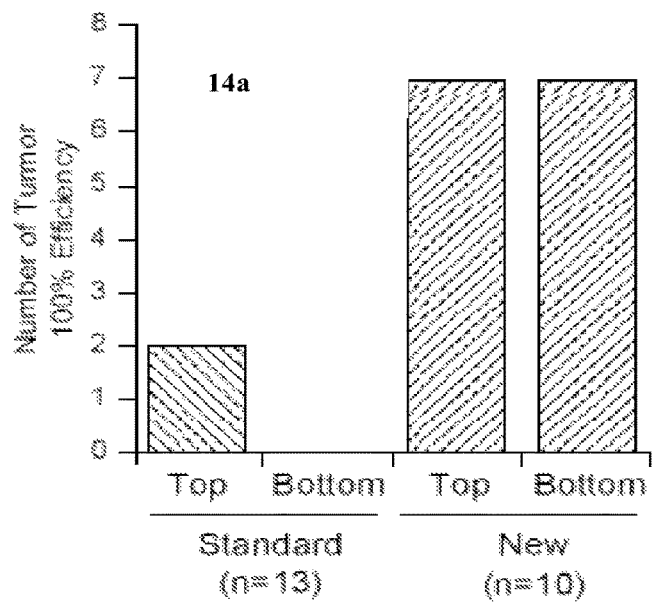
FIG. 14 shows results from two injection methods with respect to efficiency (14a), signal uniformity (14b) and column length (14c) embodying principles of the present invention.
Figure 14:
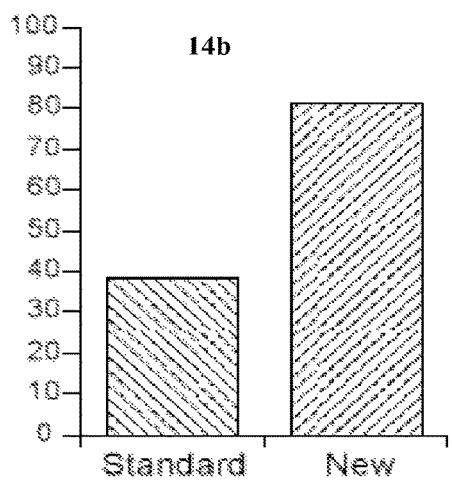
Figure 14:
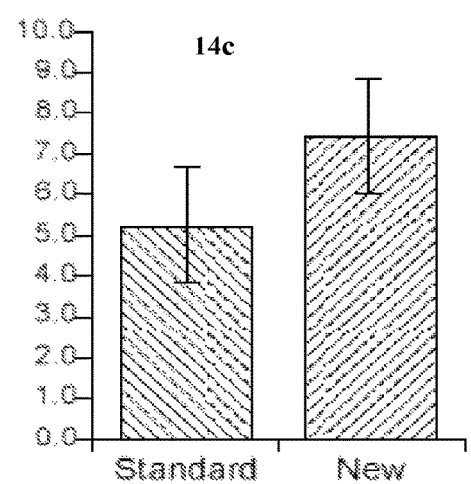

FIG. 14 shows comparison of results from a standard injection method and an exemplary injection method embodying principles of the present invention with respect to efficiency (14a), signal uniformity (14b) and column length (14c). The "new" method referred in the present example is the exemplary injection method embodying principles of the present invention involving withdrawing needles from a solid tissue and injecting an agent simultaneously into the tissue with an end port needle as described in details below. The "standard" method referred in the present example involves inserting a porous needle to a solid tissue and injecting an agent as described in details below. Injected agent is VivoTAG 680-S from Perkin Elmer. Method of detection is via the IVIS Spectrum from Perkin Elmer. Tissues injected are H2122 or RH30 cell line xenographs in nude mice.
Experimental Details for "Standard" method
   26 Gauge porous needle with 5 mm long porous region
   Flow rate of 0.70 µL/min
   No vertical retraction of needles
   5 microliter injection volume
Experimental Details for "new" method
   25 Gauge end port needle from BD Biosciences
   Flow rate of 0.70 µL/min
   Needle withdrawing rate of 1 mm/min
   5 microliter injection volume FIG. 14a. shows the "efficiency" of injection methods as defined by the number of tumors which display each of the 4 points of injection in each 2 mm slice from the "top" or dorsal and "bottom" or ventral halves of the tumor.

FIG. 14b. shows the "intratumoral signal uniformity" as defined by how consistent the signal intensity is between injection points within the same 2 mm tumor section and between different 2 mm sections. In essence it represents the range of signal intensities through the tumor with 100% being all spots show the same intensity and 0% being no 2 spots have the same signal intensity. Measurements were done using Living Image software (Perkin Elmer).

FIG. 14c. shows the vertical length (mm) of the fluorescent column within the tumor as measured by the distance between the first slice of the tumor showing signal at a given point to the last slice of the same tumor showing signal at that same point.

Example 9

Figure 15:
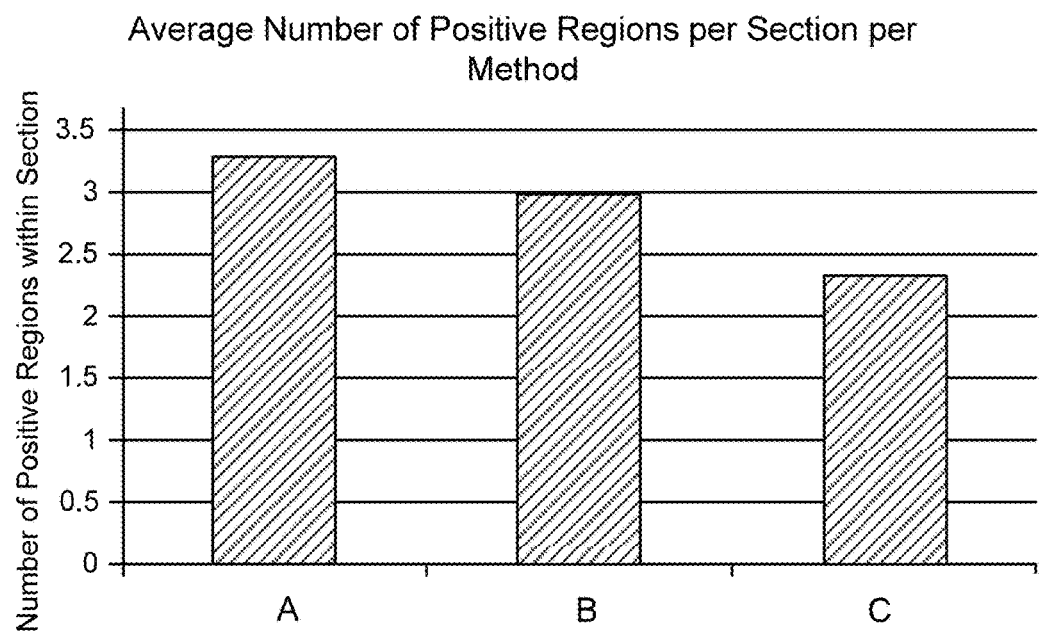
FIG. 15 shows average number of positive regions per section of three different injection methods embodying principles of the present invention.

FIG. 15 shows comparison of average number of visible points of injection out of a maximum of 4 points of injection, for each method listed below. Injected agent is VivoTag 680 S from Perkin Elmer. Method of detection is IVIS Spectrum by Perkin Elmer, Tissue injected is either H2122 or RH30 cell line xenografts in nude mice.

Figure 16:
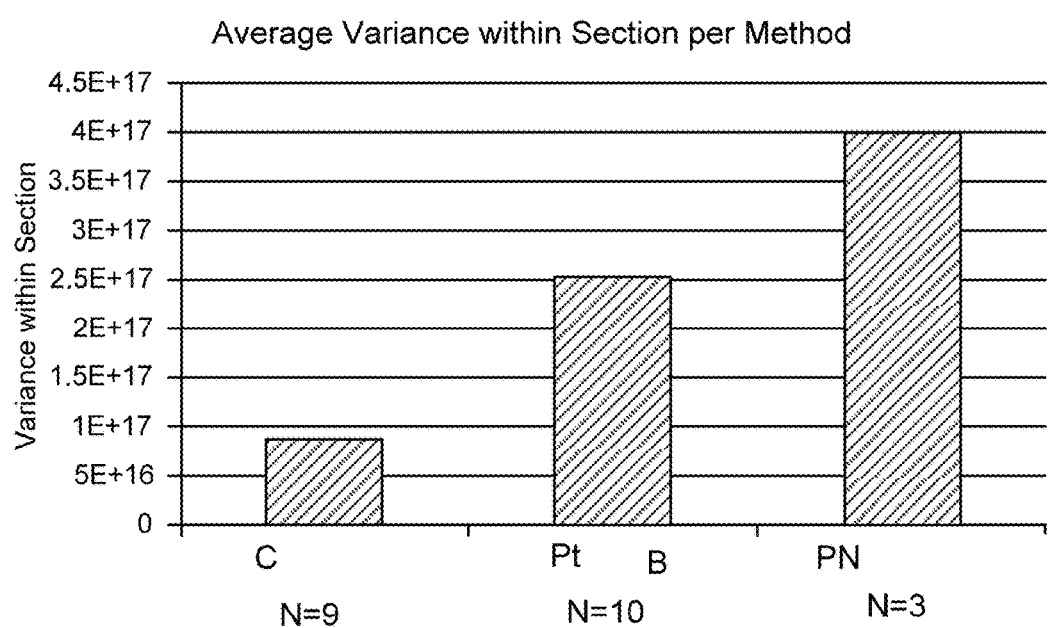
FIG. 16 shows average variance within section of three different injection methods.

FIG. 16 shows comparison average variance of fluorescent signal intensity between different injection points within the same section of a tumor, for each of the injection methods listed below Signal intensity was measured using Living Image software from Perkin Elmer. Tumor sections analyzed were the same as in FIG. 15

Experimental Details
Method A:
  25 Gauge end port needle from BD Biosciences
  Injection rate of 0.70 µL/min
  Needle withdrawing rate of 1 mm/min
Method B:
  26 Gauge porous needle with 3 mm long porous region
  Injection rate of 0.70 µL/min
  Needle withdrawing rates of 1 mm/min
  5 microliter injection volume
Method C:
  26 Gauge porous needle with 5 mm long porous region
  Injection rate of 0.70 µL/min
  No vertical retraction of needles
  5 microliter injection volume Example 10

Figure 17:
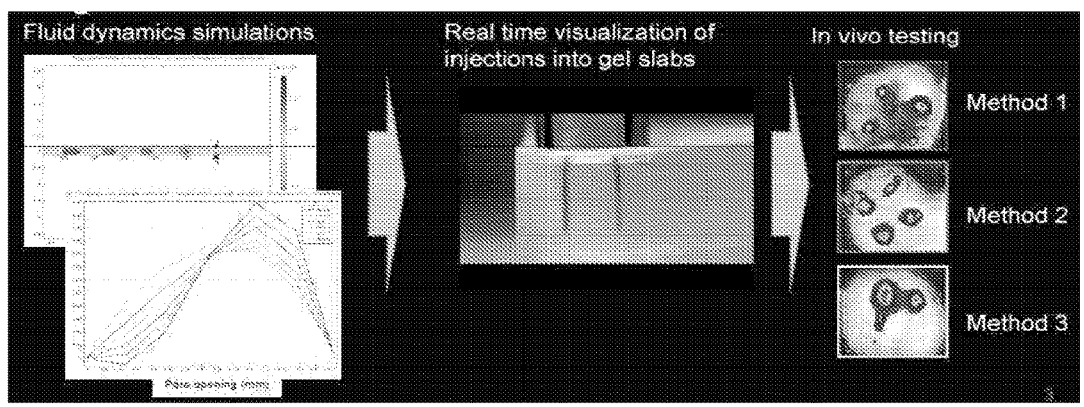
FIG. 17 shows results evaluating different injection methods with simplified experimental systems embodying principles of the present invention.

Experimental Details
FIG. 17 shows results evaluating different injection methods with simplified experimental systems.

Fluid Dynamics Simulations
Comsol multiphysics fluid dynamics software was used for simulation. Variables such as flow rate, pore size, pore number, needle length, fluid viscosity, etc. were manipulated to determine effect on fluid deposition outside the needle. Modeling was similar to what has been shown in: S. Mokhtari, V. Kudriavtsev, M. Danna, "*Flow Uniformity and Pressure Variation in Multi-outlet Flow Distribution Pipes*", ASME Vol. PVP-355, /Ed. by K. K. Panahi, *in Advances in Analytical, Experimental and Computational Technologies in Fluids, Structures, Transients and Natural Hazards, ASME Pressure Vessels and Piping Conference*, July 1997, pp. 113-122.

Real Time Visualization of Injections into Gel Slabs
Injection was done in real time and visualized with a Canon EOS Rebel T3i using a Canon EF-S 60 mm Macro Lens. Dyes injected were all standard off the shelf food coloring.
FD&C Blue No. 1, Brilliant Blue FCF, EU# E133,
FD&C Green No. 3, Fast Green FCF, EU# E143,
FD&C Red No. 3, Erythrosine, EU# E12.7
Gelatin used for injections is commonly known as "ballistics gel" and is designed to simulate animal tissue.

General Injection Conditions
Flow rates between 0.70 µL/min and 250 µL/min,
Needle withdrawing rates between 0.5 mm/min and 1 mm/20 sec, as well as no retraction of needle,
Injection volumes of 3-5 microliters,
Needle designs tested included 25 Gauge end port needle from BD Biosciences, 23 Gauge end port needle from BD Biosciences, 26 Gauge porous needles with 5 mm porous region, 26 Gauge porous needles with 3 mm porous region. Other factors varied/assessed were the amount of pressure applied by the array onto the top of the gel. Injections were repeated at least 5 times each and visually assessed as to consistency and uniform fluid distribution down the vertical column, as well as physical disruption of the gel and outflow/leak from the site of injection.

Method 1 was carried out at a fluid flow rate of 0.70 µL/min, a needle withdrawing rate of 1 mm/min and 5 microliter injection volume with 25 Gauge end port needle from BD Biosciences. Method 2 were carried out at a fluid flow rate of 0.70 µL/min, a needle withdrawing rate of 1 mm/min and 5 microliter injection volume with 26 Gauge porous needle with 3 mm long porous region. Method 3 was carried out at a fluid flow rate of 0.70 µL/min and 5 microliter injection volume without vertical needle retraction with 26 Gauge porous needle with 5 mm long porous region. Images were of either H2122 or RH30 cell line xenografts in nude mice injected with VivoTag 680 S (Perkin Elmer) and visualized using the IVIS Spectrum (Perkin Elmer).

Example 11

Figure 18:
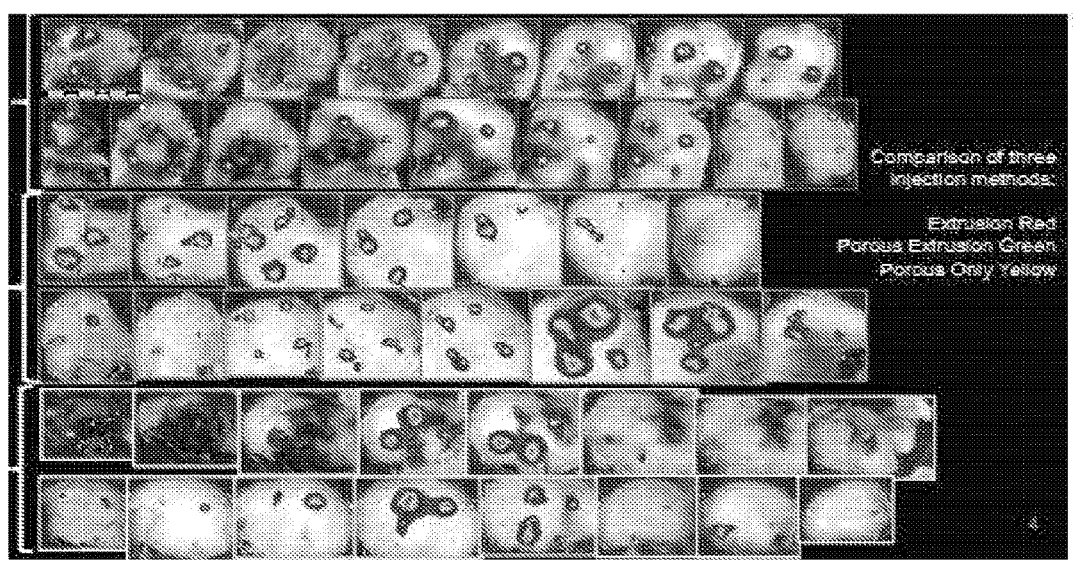
FIG. 18 shows fluorescent microscopy images of three different injection methods embodying principles of the present invention.

FIG. 18 shows fluorescent and bright field images of three different injection methods. Injections were carried out in either H2122 or RH30 cell line xenographs in nude mice. Injected agent is VivoTAG 680-S (Perkin Elmer). Imaging and signal detection was done using the IVIS Spectrum (Perkin Elmer).

The first two rows were images from a method carried out at a fluid flow rate of 0.70 µL/min, a needle withdrawing rate of 1 mm/min and 5 microliter injection volume with 25 Gauge end port needle from BD Biosciences. The third and fourth rows were images from a method carried out at a fluid flow rate of 0.70 µL/min, a needle withdrawing rate of 1 mm/min and 5 microliter injection volume with 26 Gauge porous needle with 3 mm long porous region. The fifth and sixth rows were images from a method carried out at a fluid flow rate of 0.70 µL/min and 5 microliter injection volume without vertical needle retraction with 26 Gauge porous needle with 5 mm long porous region.

Each row is showing sequential 2 mm sections from one tumor injected using a given method described above. From left to right the sections start from the dorsal side of the tumor (i.e. the face of the tumor which the needles first puncture) and move to the ventral side of the tumor.

Example 12

The insertion of microdialysis probe/s was directed by a needle guide. The needle was configured to receive one microdialysis probe. Needle gage was selected according to probe design (linear or Y-shaped as described above). To place a microdialysis probe along the desired axis the following steps was followed: 1) insertion of a microdialysis probe into the needle without the hub as to load the needle, with all of the probe front components (outlet tubing in linear probe) concealed inside the needle; 2) insertion of the guide needle into the solid tumor by penetrating the skin and tissue with a sharp end of the needle (for some organisms it may be necessary to guide the needle into the tumor subcutaneously so that none of the inlet tubing is left exposed. The needle may perforate all the way through the solid tumor if the linear probe is to be placed with out-let tubing for perfusate collection; or for general linear probe placement, the needle may create a tunnel through which the probe can be moved through until desired placement is achieved); 3) withdrawal of the needle from the solid tissue, therefore leaving the microdialysis probe in the solid tissue (in case of the linear probe placement, the outlet tubing is held in place during the needle retrieval so that the probe may remain in place; the in-let tubing is secured in place on terminal probes (no out-let tubing) during the needle removal; the needle slides all the way off the in-let tubing); 4) attachment of tubing adaptor/s onto the in-let tubing of the probe; 5) performing active pumping across the semi-permeable membrane with a peristaltic pump at the flow rates described above; 6) disconnection of the pump tubing and adjustment of the length of the in-let and out-let probe tubing by cutting, so it is suitable to remain on the organism; 7) for additional dosing, the tubing adaptor may be reattached to the in-let tubing and connected again to the pump. The probe may remain in the solid tumor for histological processing or be pulled out of the tumor.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of delivering one or more agents to a solid tumor of a subject, comprising:
   (a) inserting one or more needles of a needle array device into said solid tumor, said needle array device comprising five or more needles and one or more agents; and
   (b) injecting said one or more agents into said solid tumor via said one or more needles of said needle array device while simultaneously withdrawing said one or more needles from said solid tumor.

2. The method of claim 1, further comprising evaluating an effect of said one or more agents on said solid tumor to determine if said one or more agents is suitable for use as a therapeutic agent for said subject.

3. The method of claim 2, wherein said evaluating is performed in vitro.

4. The method of claim 2, wherein said evaluating is performed in vivo.

5. The method of claim 2, wherein said evaluating comprises detecting activity or toxicity or a lack of activity and/or toxicity of at least one of said one or more agents in separate regions of said solid tumor.

6. The method of claim 2, wherein said evaluating comprises imaging said solid tumor.

7. The method of claim 6, wherein said imaging occurs during, or after introduction of said one or more agents.

8. The method of claim 2, wherein said evaluating comprises detecting cell apoptosis after delivering a cancer therapeutic agent.

9. The method of claim 2, wherein said evaluating comprises an evaluation method selected from the group consisting of: selecting at least one of said one or more agents based on said evaluating, deselecting at least one of said one or more agents based on said evaluating, and prioritizing at least two of said agents based on said evaluating.

10. The method of claim 1, wherein said one or more agents comprises a chemotherapeutic agent.

11. The method of claim 1, wherein said one or more agents comprises an agent selected from the group consisting of a protein, a peptide, a peptidomimetic, an antibody, a small molecule, a small interfering RNA-encoding polynucleotide, an antisense RNA-encoding polynucleotide, and a ribozyme-encoding polynucleotide.

12. The method of claim 1, wherein said one or more agents comprises a fluorescent dye.

13. The method of claim 1, wherein two or more of said one or more agents are delivered simultaneously to a same region within said solid tumor.

14. The method of claim 1, wherein two or more of said one or more agents are delivered sequentially to a same region within said solid tumor.

15. The method of claim 1, wherein two or more of said one or more agents are injected at different concentrations.

16. The method of claim 1, wherein said solid tumor is selected from the group consisting of a primary tumor, an invasive tumor and a metastatic tumor.

17. The method of claim 1, further comprising marking sites of insertions.

18. The method of claim 17, wherein said one or more agents comprises a position marker.

19. The method of claim 18, wherein said position marker comprises a dye.

20. The method of claim 1, wherein each of said five or more needles comprises a different agent.

21. The method of claim 1, wherein at least two of said five or more needles each comprises a same agent at different concentrations.

22. The method of claim 1, wherein at least one of said one or more agents is a cancer therapeutic agent.

23. The method of claim 1, wherein a rate of injecting said one or more agents is at least about 0.1 µl/min.

24. The method of claim 1, wherein a rate of injecting said one or more agents is between about 0.1 µl/min and about 10 µl/min.

25. The method of claim 1, wherein a rate of withdrawing said needles is at least about 0.1 mm/min.

26. The method of claim 1, wherein outside said solid tumor said one or more agents are undetectable.

27. The method of claim 1, wherein said one or more agents is introduced in an amount that is less than a minimal dose required to produce a detectable effect in said solid tumor.

28. The method of claim 1, wherein said one or more agents is present in said solid tumor at a therapeutically effective concentration.

29. The method of claim 1, wherein outside said solid tumor said one or more agents is present at less than a minimal effective dose.

* * * * *